(12) United States Patent
Branch et al.

(10) Patent No.: US 11,826,274 B1
(45) Date of Patent: Nov. 28, 2023

(54) DEVICES AND METHODS FOR ASSISTING EXTENSION AND/OR FLEXION

(71) Applicant: ERMI, Inc., Atlanta, GA (US)

(72) Inventors: Thomas P. Branch, Atlanta, GA (US); Shaun Kevin Stinton, Chamblee, GA (US); Edward Dittmar, Marietta, GA (US); Nathaniel Kinsey DeJarnette, Atlanta, GA (US)

(73) Assignee: ERMI LLC, Atlanta, GA (US)

( * ) Notice: Subject to any disclaimer, the term of this patent is extended or adjusted under 35 U.S.C. 154(b) by 230 days.

(21) Appl. No.: 14/569,628

(22) Filed: Dec. 13, 2014

Related U.S. Application Data

(60) Provisional application No. 61/915,264, filed on Dec. 12, 2013.

(51) Int. Cl.
*A61F 5/00* (2006.01)
*A61F 5/01* (2006.01)

(52) U.S. Cl.
CPC ...... *A61F 5/013* (2013.01); *A61F 2005/0146* (2013.01)

(58) Field of Classification Search
CPC ........ A61F 5/01; A61F 5/0132; A61F 5/0125; A61F 5/013; A61F 2005/0146; A61F 2005/0148; A61F 2005/0151; A61F 2005/0153; A61F 2005/0155; A61F 2005/0165; A61F 2005/0169; A61H 1/0277; A61H 1/0274
USPC ............... 602/5, 12, 16, 20, 21, 23
See application file for complete search history.

(56) References Cited

U.S. PATENT DOCUMENTS

| | | | |
|---|---|---|---|
| 2,587,166 A * | 2/1952 | Jovick | A61F 5/0125 602/26 |
| 3,762,405 A * | 10/1973 | De George | A61F 5/0585 602/23 |
| 4,606,542 A * | 8/1986 | Segal | A61F 5/0125 482/105 |
| 4,624,246 A * | 11/1986 | Ajemian | A61F 5/0125 601/34 |
| 4,772,012 A | 9/1988 | Chesher | |
| 4,790,301 A * | 12/1988 | Silfverskiold | A61F 5/0118 602/22 |
| 4,809,688 A | 3/1989 | Aymerica del Valle et al. | |
| 5,013,037 A * | 5/1991 | Stermer | A63B 21/023 482/122 |
| 5,020,790 A * | 6/1991 | Beard | A61F 5/0102 482/4 |
| 5,103,811 A | 4/1992 | Crupi, Jr. | |

(Continued)

FOREIGN PATENT DOCUMENTS

| | | | |
|---|---|---|---|
| DE | 405327 | * | 10/1924 |
| WO | 9504507 A1 | | 2/1995 |

(Continued)

*Primary Examiner* — Adam Baker
(74) *Attorney, Agent, or Firm* — Shumaker, Loop & Kendrick, LLP; Patrick B. Horne

(57) ABSTRACT

Embodiments of the invention are directed to devices and methods for providing extension and flexion assistance about a joint of a user. In some cases, a device may manipulate an arm of a user, thereby providing extension or flexion assistance to the arm about an elbow. In other cases, a device may manipulate a hand of a user to provide palmar flexion or dorsiflexion assistance about a wrist of the user.

17 Claims, 44 Drawing Sheets

(56) References Cited

U.S. PATENT DOCUMENTS

| | | | |
|---|---|---|---|
| 5,213,094 A * | 5/1993 | Bonutti | A61F 5/0123 601/33 |
| 5,328,448 A | 7/1994 | Gray, Sr. | |
| 5,337,737 A * | 8/1994 | Rubin | A63B 23/1281 128/898 |
| 5,364,323 A | 11/1994 | Liu | |
| 5,476,439 A | 12/1995 | Robinson | |
| 5,571,206 A * | 11/1996 | Varn | A61F 5/0125 602/23 |
| 5,658,241 A | 8/1997 | Deharde et al. | |
| 5,662,594 A | 9/1997 | Rosenblatt | |
| 5,681,269 A | 10/1997 | Basaj et al. | |
| 5,683,353 A * | 11/1997 | Hamersly | A61F 5/0125 601/33 |
| 5,697,892 A | 12/1997 | Torgerson | |
| 5,738,636 A | 4/1998 | Saringer et al. | |
| 5,817,040 A | 10/1998 | Hess et al. | |
| 5,820,577 A | 10/1998 | Taylor | |
| 5,823,886 A | 10/1998 | Murray | |
| 5,848,979 A | 12/1998 | Bonutti et al. | |
| 5,865,714 A * | 2/1999 | Marlowe | A63B 21/153 482/112 |
| 5,891,061 A | 4/1999 | Kaiser | |
| 5,891,079 A | 4/1999 | Barnes | |
| 5,899,870 A | 5/1999 | Deirmendjian et al. | |
| 5,951,499 A | 9/1999 | Saringer et al. | |
| 5,957,813 A | 9/1999 | Macdonald | |
| 5,976,058 A | 11/1999 | Gustafson | |
| 6,001,075 A | 12/1999 | Clemens et al. | |
| 6,063,087 A | 5/2000 | Agee et al. | |
| 6,080,122 A | 6/2000 | Gulledge | |
| 6,117,097 A | 9/2000 | Ruiz | |
| 6,142,964 A | 11/2000 | Gilmour | |
| 6,179,799 B1 | 1/2001 | Doran | |
| 6,196,985 B1 | 3/2001 | Slautterback | |
| 6,293,918 B1 | 9/2001 | Wang | |
| 6,506,172 B1 | 1/2003 | Hepburn et al. | |
| 6,537,237 B1 | 3/2003 | Hopkins et al. | |
| 6,565,563 B1 | 5/2003 | Agee et al. | |
| 6,689,080 B2 | 2/2004 | Castillo | |
| 6,740,051 B2 | 5/2004 | Hepburn et al. | |
| 6,793,641 B2 | 9/2004 | Freeman et al. | |
| 6,921,377 B2 | 7/2005 | Bonutti | |
| 6,969,365 B2 | 11/2005 | Scorvo | |
| 7,001,352 B2 | 2/2006 | Farrell et al. | |
| 7,083,583 B2 | 8/2006 | Opahle et al. | |
| 7,090,650 B2 | 8/2006 | Ou et al. | |
| 7,101,347 B2 | 9/2006 | Culhane et al. | |
| 7,112,179 B2 | 9/2006 | Bonutti et al. | |
| 7,156,818 B2 | 1/2007 | Salmon et al. | |
| 7,156,819 B2 | 1/2007 | Sieller et al. | |
| 7,404,804 B2 | 7/2008 | Bonutti | |
| 7,404,805 B2 | 7/2008 | Weiss | |
| 7,452,342 B2 | 11/2008 | Bonutti et al. | |
| 7,491,186 B2 | 2/2009 | Zeide et al. | |
| 7,517,329 B2 | 4/2009 | Salmon et al. | |
| 7,534,219 B2 | 5/2009 | Stearns | |
| 7,537,547 B1 | 5/2009 | Hosick et al. | |
| 7,537,577 B2 | 5/2009 | Phelan et al. | |
| 7,601,130 B2 | 10/2009 | Farrell et al. | |
| 7,621,883 B2 | 11/2009 | Duren et al. | |
| 7,699,797 B2 | 4/2010 | Nordt, III et al. | |
| 7,704,219 B2 | 4/2010 | Nordt, III et al. | |
| 7,833,183 B2 | 11/2010 | Padova | |
| 7,878,998 B2 | 2/2011 | Nordt, III et al. | |
| 7,892,194 B2 | 2/2011 | Farrell et al. | |
| 7,914,475 B2 | 3/2011 | Wyatt et al. | |
| 7,922,680 B2 | 4/2011 | Nordt, III et al. | |
| 7,955,286 B2 | 6/2011 | Bonutti et al. | |
| 7,967,765 B2 | 6/2011 | Nathanson | |
| 7,981,067 B2 | 7/2011 | Bonutti et al. | |
| 7,993,294 B2 | 8/2011 | Hassler et al. | |
| 8,012,108 B2 | 9/2011 | Bonutti et al. | |
| 8,016,781 B2 | 9/2011 | Ingimundarson et al. | |
| 8,038,637 B2 | 10/2011 | Bonutti | |
| 8,070,702 B2 | 12/2011 | Farrell et al. | |
| 8,147,438 B2 | 4/2012 | Livolsi et al. | |
| 8,172,781 B2 | 5/2012 | Oddou et al. | |
| 8,206,329 B2 | 6/2012 | Bonutti et al. | |
| 8,216,168 B2 | 6/2012 | Farrell et al. | |
| 8,231,560 B2 | 7/2012 | Ingimundarson et al. | |
| 8,235,928 B2 | 8/2012 | Padova | |
| 8,246,559 B2 | 8/2012 | Hoffman et al. | |
| 8,246,560 B2 | 8/2012 | Gaylord et al. | |
| 8,257,283 B2 | 9/2012 | Kaiser | |
| 8,273,043 B2 | 9/2012 | Bonutti et al. | |
| 8,328,743 B2 | 12/2012 | Farrell et al. | |
| 8,328,744 B2 | 12/2012 | Farrell et al. | |
| 8,348,810 B2 | 1/2013 | Land et al. | |
| 8,419,670 B2 | 4/2013 | Downing | |
| 8,425,440 B2 | 4/2013 | DeToro et al. | |
| 8,460,222 B2 | 6/2013 | Garrec | |
| 8,517,965 B2 | 8/2013 | Doty et al. | |
| 8,574,137 B2 | 11/2013 | Chen et al. | |
| 8,591,443 B2 | 11/2013 | Bonutti et al. | |
| 8,622,939 B2 | 1/2014 | Nguyen | |
| 8,622,945 B2 | 1/2014 | Meals | |
| 8,652,076 B2 | 2/2014 | Land et al. | |
| 8,678,980 B2 | 3/2014 | Land et al. | |
| 8,679,043 B2 | 3/2014 | Bonutti | |
| 8,679,045 B2 | 3/2014 | Dao | |
| 8,702,634 B2 | 4/2014 | Crompton | |
| 8,708,939 B2 | 4/2014 | Bonutti et al. | |
| 8,740,829 B2 | 6/2014 | Lee et al. | |
| 8,753,301 B2 | 6/2014 | Tran | |
| 8,771,212 B1 | 7/2014 | Garris et al. | |
| 8,784,343 B2 | 7/2014 | Bonutti et al. | |
| 8,784,348 B2 | 7/2014 | Farrell et al. | |
| 8,814,816 B2 | 8/2014 | Bonutti et al. | |
| 8,821,420 B1 | 9/2014 | Callahan | |
| 8,827,873 B2 | 9/2014 | Arnstein | |
| 8,864,692 B2 | 10/2014 | Ingimundarson et al. | |
| 8,864,695 B2 | 10/2014 | Thornton | |
| 8,882,688 B1 | 11/2014 | Ancinec | |
| 2002/0151832 A1 | 10/2002 | Wedge, Jr. | |
| 2006/0264792 A1 | 11/2006 | Bonn | |
| 2007/0038161 A1 * | 2/2007 | Bonutti | A61F 5/0102 601/5 |
| 2010/0049110 A1 * | 2/2010 | Blanchard | A61F 5/05841 602/20 |
| 2011/0152736 A1 | 6/2011 | Ng | |
| 2012/0059298 A1 | 3/2012 | Hoffman et al. | |
| 2012/0215145 A1 | 8/2012 | Ingimundarson et al. | |
| 2012/0316475 A1 * | 12/2012 | Bhugra | A61F 2/68 601/33 |
| 2012/0323148 A1 | 12/2012 | Kaiser | |
| 2013/0072829 A1 | 3/2013 | Fausti et al. | |
| 2013/0110020 A1 | 5/2013 | Ingimundarson et al. | |
| 2013/0144195 A1 | 6/2013 | Cehic | |
| 2013/0317395 A1 | 11/2013 | Laflin | |
| 2013/0338547 A1 | 12/2013 | Shimizuhira et al. | |
| 2013/0338548 A1 | 12/2013 | Nakamura | |
| 2014/0194799 A1 | 7/2014 | Bonutti et al. | |
| 2014/0303527 A1 | 10/2014 | Bonutti et al. | |

FOREIGN PATENT DOCUMENTS

| | | |
|---|---|---|
| WO | 9945864 A1 | 9/1999 |
| WO | 2004041485 A1 | 5/2004 |
| WO | 2006058442 A8 | 8/2006 |
| WO | 2006138142 A2 | 12/2006 |
| WO | 2006138142 A3 | 12/2006 |
| WO | 2009015364 A1 | 1/2009 |
| WO | 2011156773 A1 | 12/2011 |
| WO | 2013163733 A1 | 11/2013 |
| WO | 2014033613 A3 | 3/2014 |
| WO | 2014146766 A1 | 9/2014 |

* cited by examiner

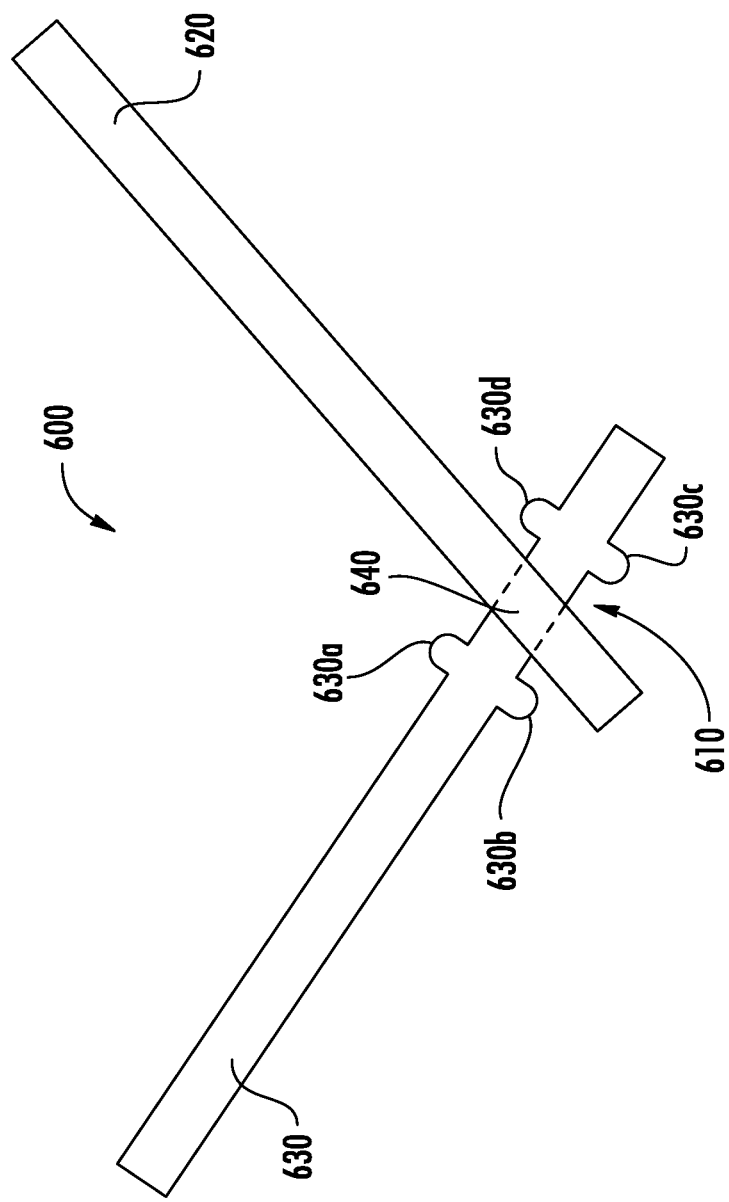

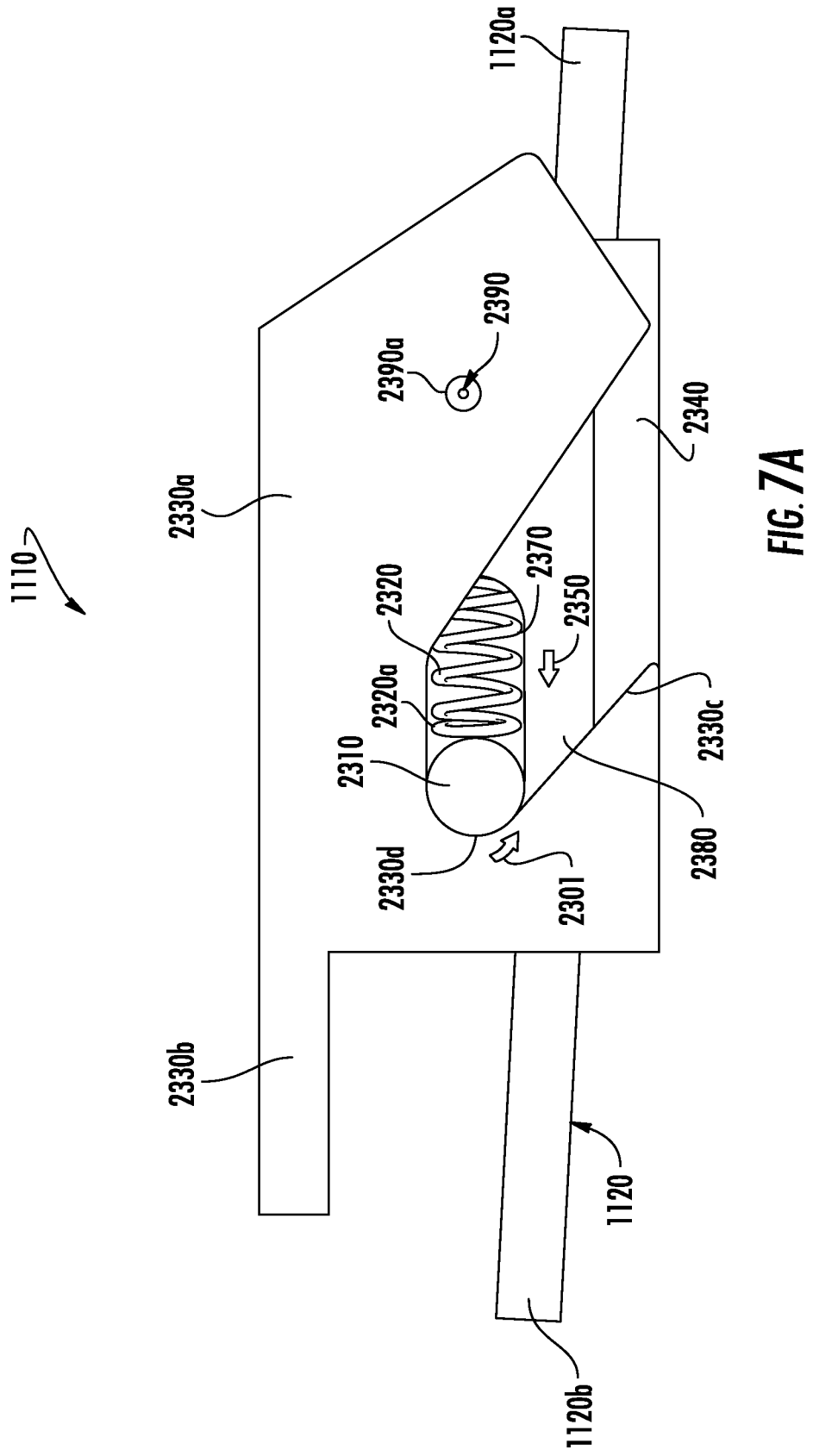

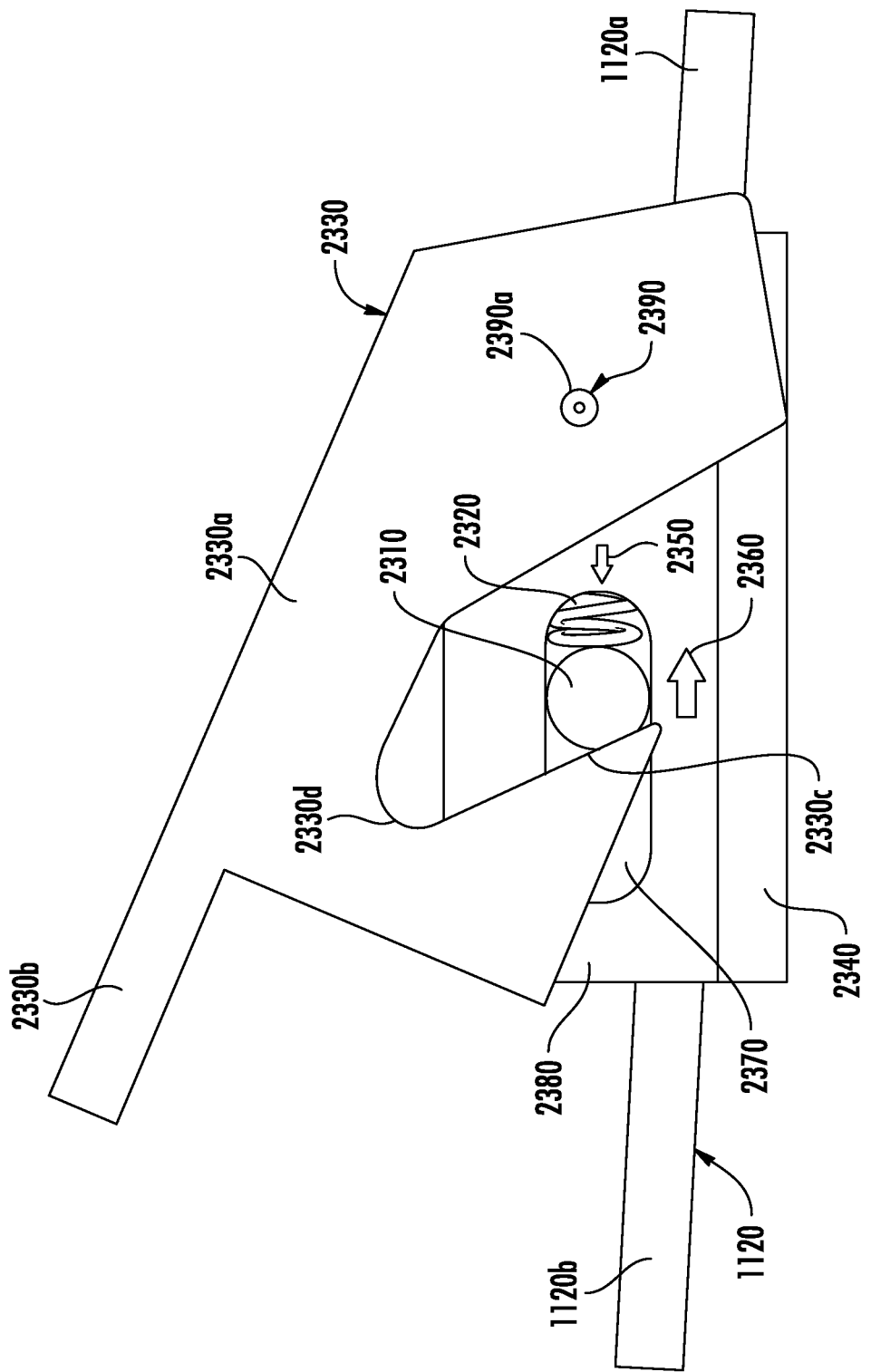

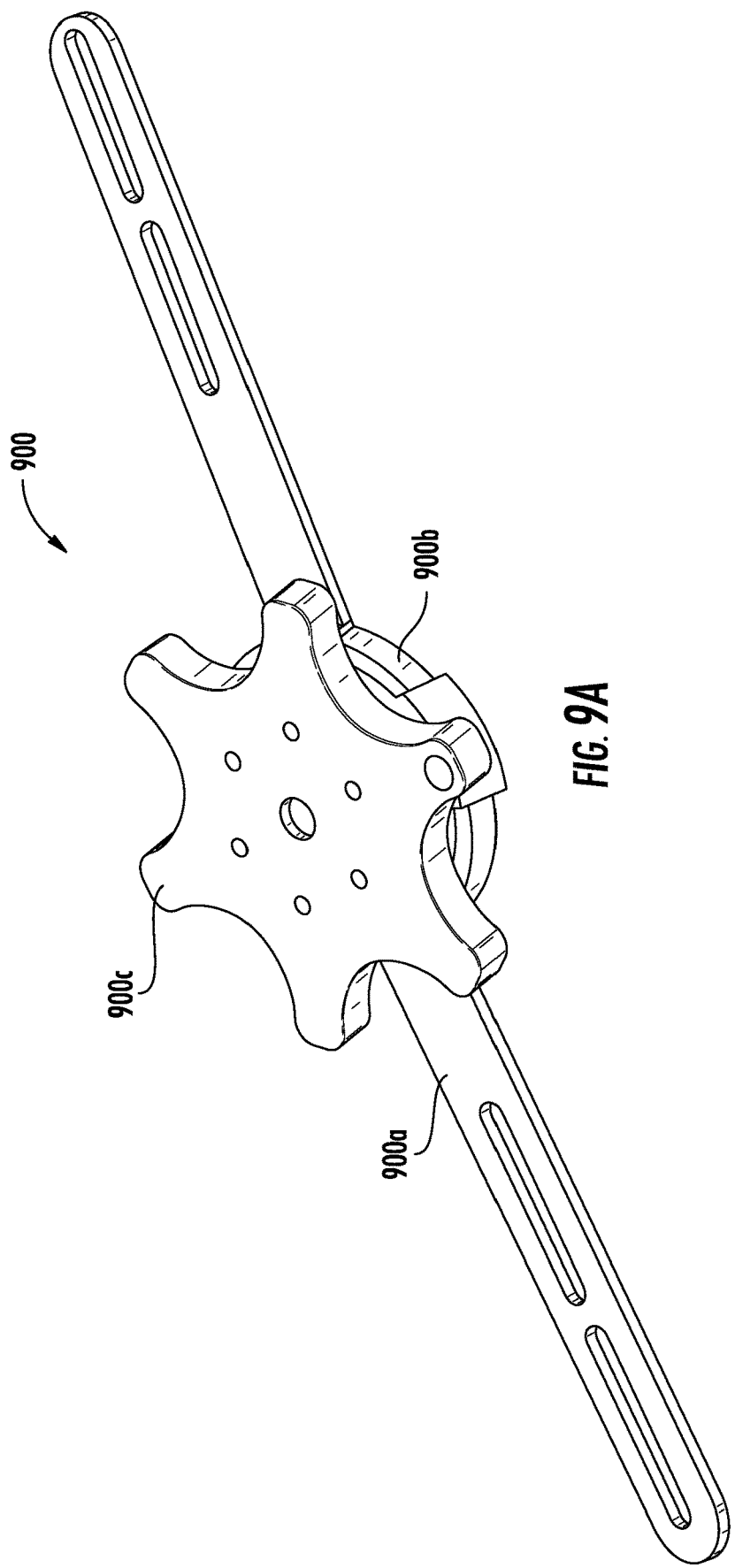

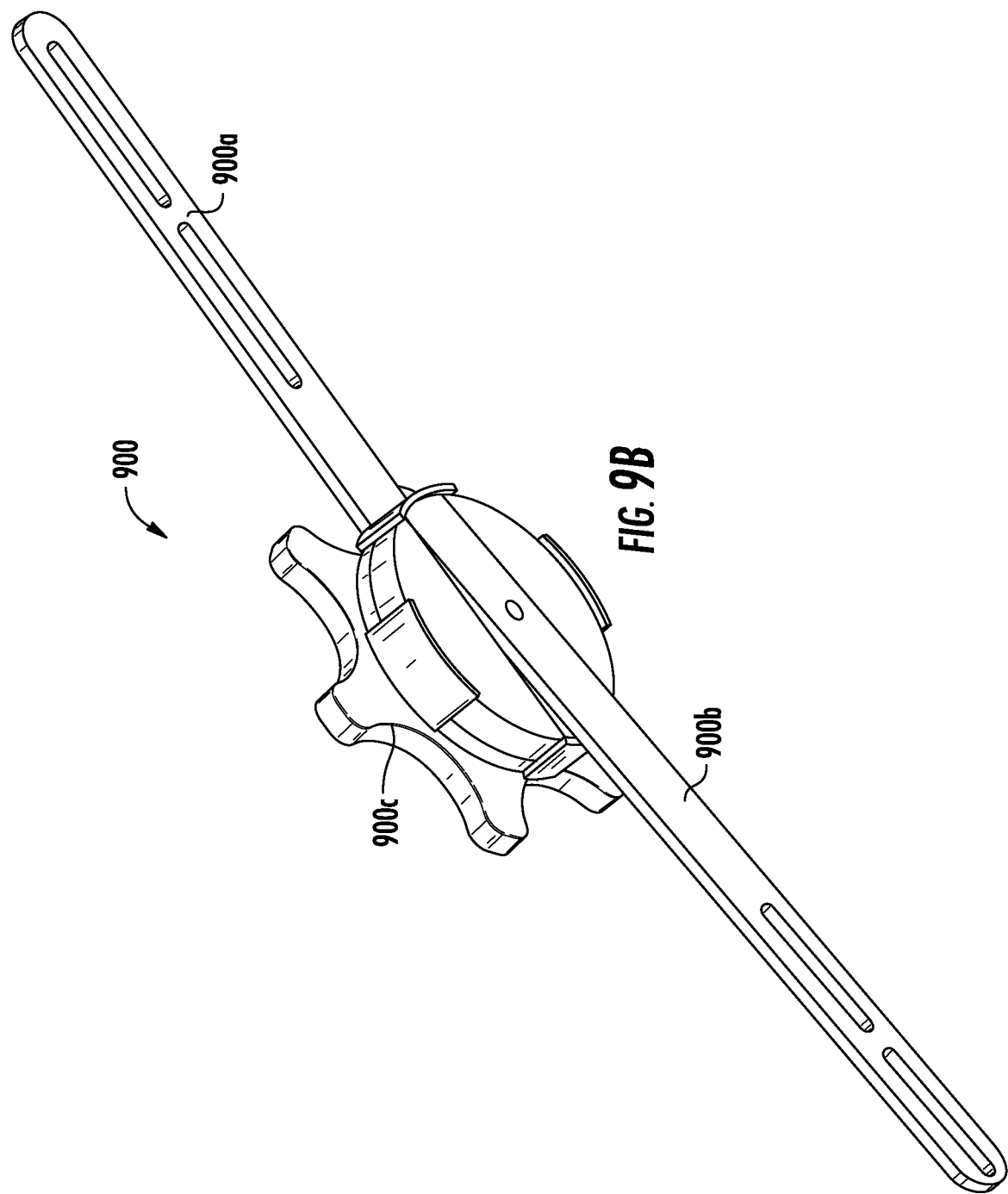

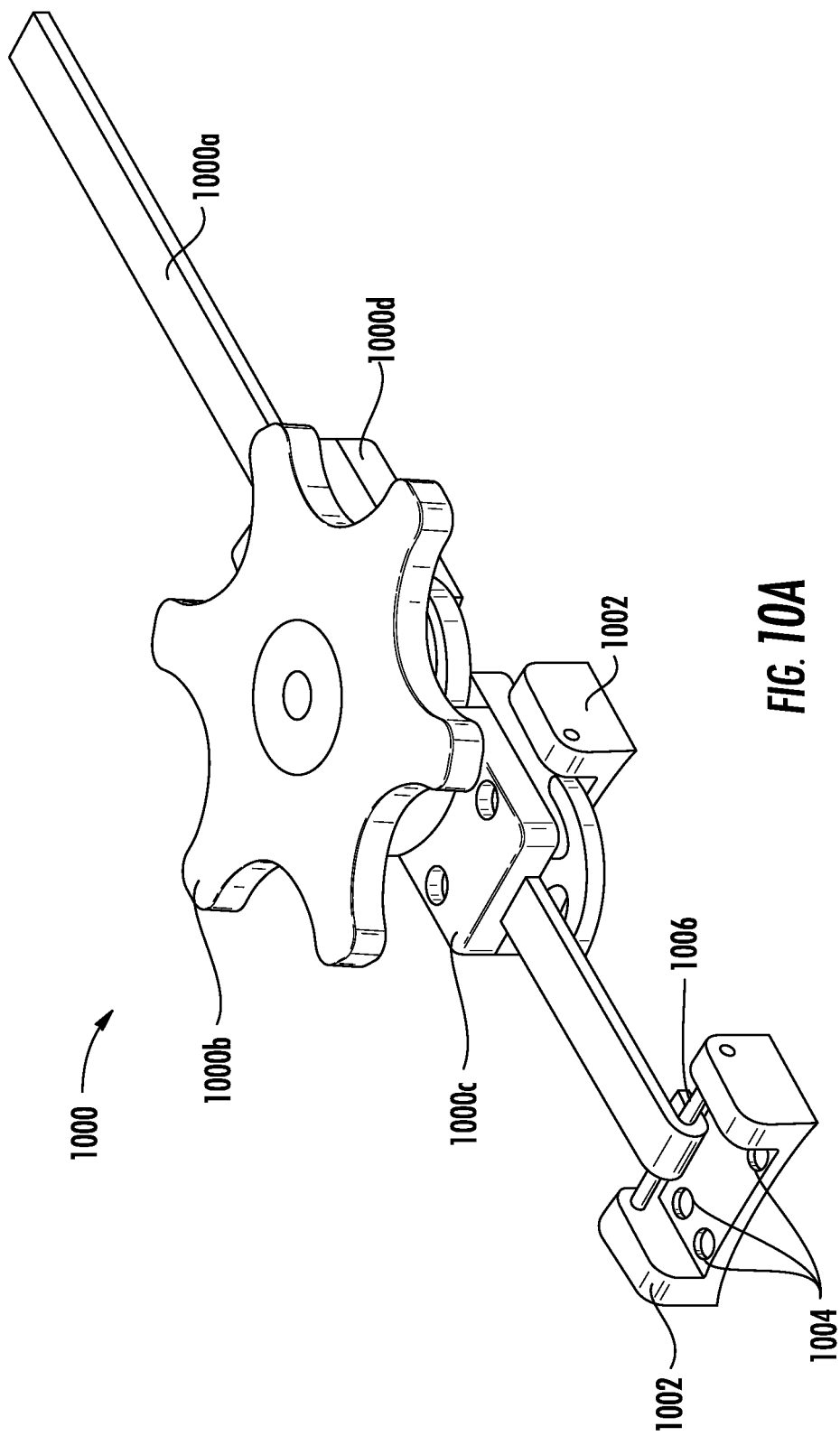

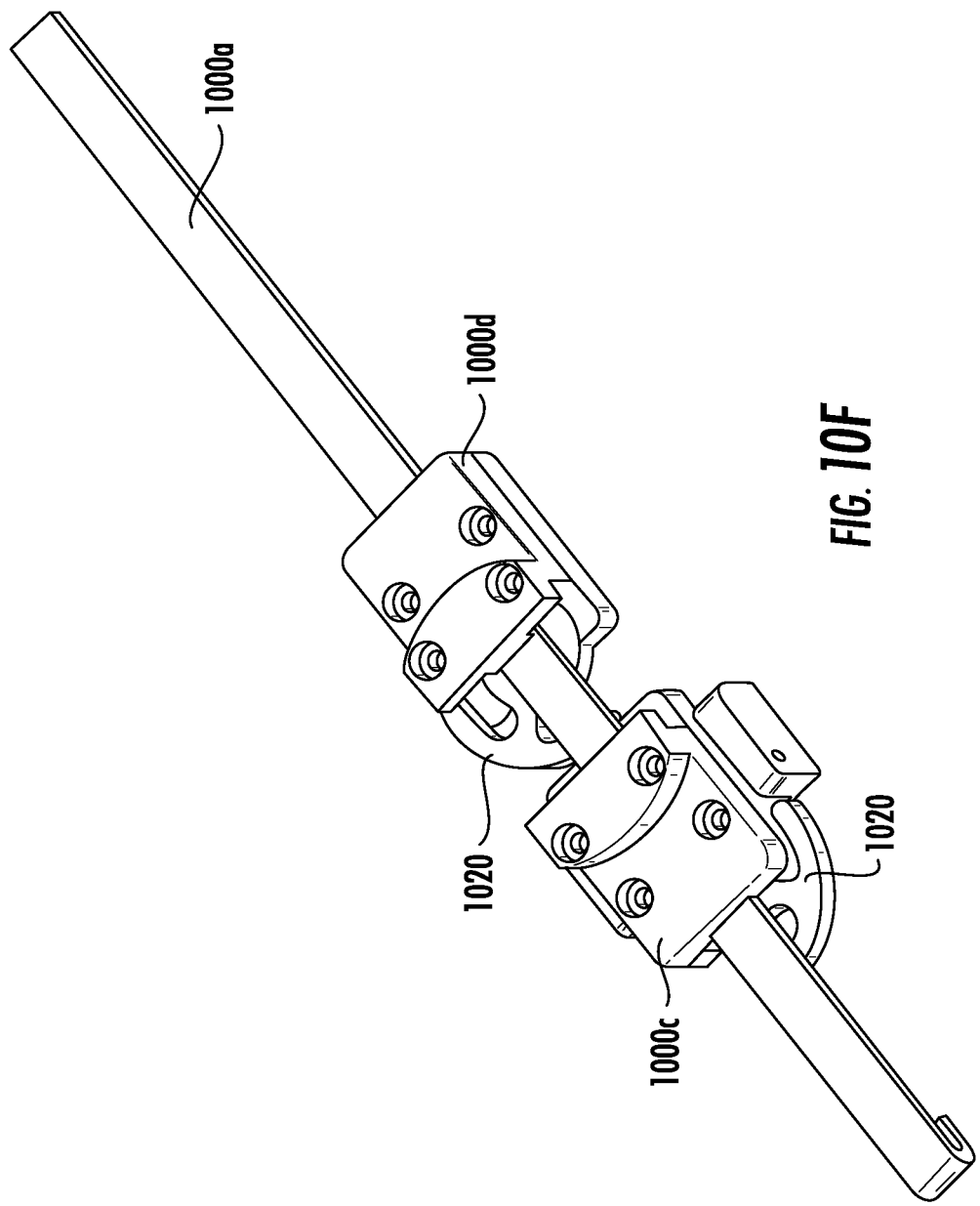

DEVICES AND METHODS FOR ASSISTING EXTENSION AND/OR FLEXION

CLAIM OF PRIORITY UNDER 35 U.S.C. § 119

The present Application for Patent claims priority to Provisional Application No. 61/915,264 entitled "Upper Extremity Support and Range of Motion Device and Methods for Using Same" filed Dec. 12, 2013 and assigned to the assignee hereof and hereby expressly incorporated by reference herein.

TECHNICAL FIELD

This invention relates generally to orthotic devices and more particularly to orthotic devices designed to improve and promote gains in range of motion in a joint by use of mechanical lever systems and/or pneumatic systems.

BACKGROUND

When a joint is damaged either from an injury event or through surgical intervention, scar tissue may form and limit the motion of the joint. This loss of motion can greatly affect a person's quality of life by limiting their ability to accomplish their normal activities of daily living. Traditionally, orthotics are separated into two categories: those that support and protect limbs and those that attempt to return range of motion to the joint by application of force.

Different joints are capable of moving in different directions, and the full range of motion of a joint depends upon the anatomy of that joint and on the particular genetics of each individual. Joint motion can generally be classified as linear or rotational. For example, linear joint motions include flexion and extension where flexion is defined as a bending of the joint and extension is often defined as a straightening of the joint. Rotational motions include pronation and supination, which is where the hand rotates around the longitudinal axis of the forearm placing the palm up or the palm down.

Conventional orthotic devices have attempted to provide support across a joint, traditionally utilizing a rigid member or hinged joint. Orthotics aim to protect the joint by supporting the joint.

Some devices use a hinge system to apply a low load force on the joint by tightening a spring and thus stretching accumulated scar tissue over a long period of time. Some use a cuff for each limb segment and are uncomfortable and must be worn for hours at a time to be effective.

BRIEF SUMMARY

Embodiments of the invention are directed to a device for manipulating an arm of a user, thereby providing extension or flexion assistance to the arm about an elbow, the device comprising an arm engagement system comprising an upper arm member configured to engage an upper arm of the user; and a forearm member configured to engage a forearm of the user, the forearm member operatively coupled to the upper arm member at a joint, wherein the upper arm member and forearm member are configured to pivot about an axis defined by the joint as the user extends or flexes the arm about the elbow; and a force application system comprising a first elongate member operatively coupled to the arm engagement system; a force applicator operatively coupled to the first elongate member or the arm engagement system; and a force application mechanism operatively coupled to the first elongate member when the force applicator is operatively coupled to the arm engagement system, or operatively coupled to the arm engagement system when the force applicator is operatively coupled to the first elongate member, and the force application mechanism is configured to apply a force to the force applicator, thereby providing the extension or flexion assistance to the arm about the elbow.

In some embodiments, the first elongate member is operatively coupled to the upper arm member. In some embodiments, the force application mechanism is operatively coupled to the first elongate member. In some such embodiments, the first elongate member comprises a distal portion and a member portion opposite the distal portion; and the force application mechanism is operatively coupled to the first elongate member proximate the distal portion of the first elongate member. In some embodiments, the force applicator is operatively coupled to the forearm member.

In some embodiments, the force application mechanism is operatively coupled to the forearm member.

In some embodiments, the first elongate member comprises a distal portion and a member portion opposite the distal portion; and the force applicator is operatively coupled to the first elongate member proximate the distal portion of the first elongate member. In some embodiments, the force application mechanism applies the force applicator causing the upper arm member and the forearm member to pivot about the axis toward one another, thereby providing flexion assistance to the arm about the elbow.

In some embodiments, the first elongate member is operatively coupled to the forearm member.

In some embodiments, the force application mechanism is operatively coupled to the first elongate member.

In some embodiments, the first elongate member comprises a distal portion and a member portion opposite the distal portion; and the force application mechanism is operatively coupled to the first elongate member proximate the distal portion of the first elongate member.

In some embodiments, the force applicator is operatively coupled to the upper arm member.

In some embodiments, the force application mechanism is operatively coupled to the upper arm member.

In some embodiments, the first elongate member comprises a distal portion and a member portion opposite the distal portion; and the force applicator is operatively coupled to the first elongate member proximate the distal portion of the first elongate member.

In some embodiments, the force application mechanism applies the force to the force applicator causing the upper arm member and the forearm member to pivot about the axis toward one another, thereby providing flexion assistance to the arm about the elbow.

In some embodiments, the first elongate member is operatively coupled to the upper arm member; the force application system further comprises a second elongate member operatively coupled to the forearm member; and the force applicator is operatively coupled to the first elongate member and the second elongate member.

In some embodiments, the force applicator mechanism is operatively coupled to the first elongate member.

In some embodiments, the first elongate member comprises a distal portion and a member portion opposite the distal portion; the force application mechanism is operatively coupled to the first elongate member proximate the distal portion of the first elongate member.

In some embodiments, the second elongate member comprises a distal portion and a member portion opposite the distal portion; and the force applicator is operatively coupled to the first elongate member proximate the distal portion of the first elongate member and operatively coupled to the second elongate member proximate the distal portion of the second elongate member. In some such embodiments, the force applicator mechanism is operatively coupled to the second elongate member. In some such embodiments, the second elongate member comprises a distal portion and a member portion opposite the distal portion; and the force application mechanism is operatively coupled to the second elongate member proximate the distal portion of the second elongate member. In some such embodiments, the first elongate member comprises a distal portion and a member portion opposite the distal portion; and the force applicator is operatively coupled to the second elongate member proximate the distal portion of the second elongate member and operatively coupled to the first elongate member proximate the distal portion of the first elongate member.

In some embodiments, the force application mechanism causes the force to be applied to the force applicator causing the upper arm member and the forearm member to pivot about the axis toward one another, thereby providing flexion assistance to the arm about the elbow.

In some embodiments, the force application mechanism causes the force to be applied to the force applicator causing the upper arm member and the forearm member to pivot about the axis away from one another, thereby providing extension assistance to the arm about the elbow. In some such embodiments, the first elongate member comprises a distal portion and a member portion opposite the distal portion and the first elongate member is fixedly coupled to the upper arm member proximate the member portion of the first elongate member at a first coupling; the second elongate member comprises a distal portion and a member portion opposite the distal portion and the second elongate member is fixedly coupled to the forearm member proximate the member portion of the second elongate member at a second coupling; and as the force is caused by the force application mechanism, a distance between the distal portion of the first elongate member and the distal portion of the second elongate member decreases, thereby creating a first torque at the first coupling and about the joint and a second torque at the second coupling and about the joint, the first torque and the second torque urging the upper arm member and the forearm member away from one another to provide extension assistance to the arm about the elbow. In some such embodiments, the first elongate member forms a first acute angle with the upper arm member, wherein the first acute angle faces the joint; and the second elongate member forms a second acute angle with the forearm member, wherein the second acute angle faces the joint.

In some embodiments, the force application mechanism, when the force is applied, urges the arm engagement system from a first position to a second position to provide extension or flexion assistance.

In some embodiments, the force application mechanism comprises a rotary mechanism. In some such embodiments, the rotary mechanism causes a non-incremental or continuous force to be applied when the rotary mechanism is activated by the user.

In some embodiments, the force application mechanism, when the force is applied, urges the arm engagement system from a first position to a second position to achieve extension or flexion assistance. In some such embodiments, the rotary mechanism is configured to restrict, at least partially, movement of the arm engagement system from the second position to the first position.

According to embodiments of the invention, a device for manipulating an arm of a user, thereby providing extension or flexion assistance to the arm about an elbow, comprises an arm engagement system comprising an upper arm member configured to engage an upper arm of the user; and a forearm member configured to engage a forearm of the user, the forearm member operatively coupled to the upper arm member at a joint, wherein the upper arm member and forearm member are configured to pivot about an axis defined by the joint as the user extends or flexes the arm about the elbow. The device also has a force application system comprising a force applicator operatively coupled to the arm engagement system; and a force application mechanism operatively coupled to the arm engagement system, the force application mechanism comprising a rotary mechanism that causes a non-incremental or continuous force to be applied when the rotary mechanism is activated by the user.

In some embodiments, the force application mechanism, when the force is applied, urges the arm engagement system from a first position to a second position to achieve extension or flexion assistance.

In some embodiments, the rotary mechanism is configured to restrict, at least partially, movement of the arm engagement system from the second position to the first position.

According to embodiments of the invention, a device for manipulating body parts of a user, thereby providing extension or flexion assistance to the body parts about a joint, the device includes a body part engagement system comprising a first member configured to engage a first body part of the user; and a second member configured to engage a second body part of the user, the second member operatively coupled to the first member at a device joint, wherein the first member and second member are configured to pivot about an axis defined by the device joint as the user extends or flexes the first body part and/or second body part about the joint. The device also has a force application system comprising a first elongate member operatively coupled to the body part engagement system; a force applicator operatively coupled to the first elongate member or the body part engagement system; and a force application mechanism operatively coupled to the first elongate member when the force applicator is operatively coupled to the body part engagement system, or operatively to the body part engagement system when the force applicator is operatively coupled to first elongate member, and the force application mechanism is configured to apply a force to the force applicator, thereby providing the extension or flexion assistance to the first body part and/or second body part about the joint. According to embodiments of the invention, a device for manipulating body parts of a user, thereby providing extension or flexion assistance to the body parts about a joint comprises a body part engagement system comprising a first member configured to engage first body part of the user; and a second member configured to engage a second body part of the user, the second member operatively coupled to the first member at a device joint, wherein the first member and second member are configured to pivot about an axis defined by the device joint as the user extends or flexes the first and/or second body parts about the joint; and a force application system comprising a force applicator operatively coupled to the body part engagement system; and a force application mechanism operatively coupled to the body part engagement system, the force application mechanism comprising a rotary mechanism that applies a non-incremental or continuous force when the rotary mechanism is activated by the user, thereby providing the extension or flexion assistance to the first body part and/or second body part about the joint.

According to embodiments of the invention, a device for manipulating a hand of a user to provide palmar flexion or dorsiflexion assistance about a wrist of the user comprises a hand interface configured to engage the hand of the user; a forearm member configured to engage a forearm of the user, the forearm member operatively coupled to the hand interface at a joint, wherein the hand interface and the forearm member are configured to pivot about an axis defined by the joint as the user's wrist moves into palmar flexion or moves into dorsiflexion; a force applicator operatively coupled to the hand interface and the forearm member; a force application mechanism operatively coupled to the force applicator and configured to apply a force to the force applicator, thereby providing palmar or dorsiflexion assistance to the wrist.

In some embodiments, the force application mechanism is operatively coupled to the forearm member or the hand interface. In some such embodiments, the force application mechanism comprises a rotary mechanism and the force applicator comprises a cable, wherein the rotary mechanism is configured to wind the cable as the rotary mechanism is activated by the user, thereby applying the force to the hand interface. In some such embodiments, the rotary mechanism, when turned, applies the force in a continuous or non-incremental fashion. In some such embodiments, the hand interface is configured to move from a first position to a second position when the force is applied by the force application mechanism. In some such embodiments, the first position provides a lower degree of palmar flexion or dorsiflexion to the wrist of the user than the second position.

In some embodiments, the hand interface is configured to be changed from a first interface position wherein the force applicator applies the force to assist palmar flexion to a second interface position wherein the force applicator applies the force to assist dorsiflexion.

In some embodiments, the hand interface is configured to be changed from a first interface position wherein the force applicator applies the force to assist dorsiflexion to a second interface position wherein the force applicator applies the force to assist palmar flexion.

In some embodiments, the device also includes a force amplifier configured to redirect an original force originating from the force application mechanism and apply it to the hand interface. In some such embodiments, the force amplifier comprises a peg operatively coupled to the forearm member, the peg configured to receive and retain the cable.

In some embodiments, the hand interface comprises an L-shaped platform configured to receive and engage at least a portion of a palmar side of the hand and an ulnar side of the hand.

In some embodiments, the hand interface comprises an L-shaped platform configured to receive and engage at least a portion of a dorsal side of the hand and at least a portion of an ulnar side of the hand.

In some embodiments, the hand interface comprises an ulnar portion configured to receive and engage at least a portion of an ulnar side of the hand; an elongate member extending outward from the ulnar portion; wherein the force applicator is operatively coupled to the elongate member, the elongate member configured to cause a torque about the joint in the direction of the force when the force is applied by the force application member.

In some embodiments, the device also includes a second force application mechanism configured to cause a second force to be applied to the hand of the user, thereby providing a second palmar or dorsiflexion assistance to the wrist. In some such embodiments, the second force application mechanism comprises a bladder configured to fill with a fluid; and the second force is configured to further urge the hand in the direction of the force applied by the force application mechanism. In some such embodiments, the force applied by the force application mechanism is relatively course in relation to the second force applied by the second force application mechanism.

According to embodiments of the invention, a device for manipulating a hand of a user to provide palmar flexion or dorsiflexion assistance about a wrist of the user comprises a hand interface configured to engage the hand of the user; a forearm member configured to engage a forearm of the user, the forearm member operatively coupled to the hand interface at a joint, wherein the hand interface and the forearm member are configured to pivot about an axis defined by the joint as the user's wrist moves into palmar flexion or moves into dorsiflexion; a force applicator operatively coupled to the hand interface; a force application mechanism configured to cause a force to be applied to the hand interface in a first direction, thereby providing palmar or dorsiflexion assistance to the wrist; and a restriction mechanism configured to restrict movement of the hand interface in a second direction substantially opposite the first direction. In some such embodiments, the force application mechanism comprises a pump and the force applicator comprises a bladder configured to fill with a fluid when the pump is activated. In other such embodiments, the restriction mechanism comprises a friction bar mechanism. In some such embodiments, the restriction mechanism further comprises a rotary mechanism operably coupled with the friction bar mechanism and configured to apply a second force to the hand interface as the rotary mechanism is activated, the second force urging the hand interface substantially in the first direction, thereby further providing palmar or dorsiflexion assistance to the wrist.

In some embodiments, the friction bar mechanism is operatively coupled with the forearm member and the hand interface. In some such embodiments, the friction bar mechanism comprises a bar and a friction lock operatively coupled with the bar; wherein the bar is operatively coupled to the hand interface and the friction lock is operatively coupled to the forearm member; wherein the friction lock is configured to allow movement of the bar with respect to the friction lock in a forearm direction and restricts movement of the bar with respect to the friction lock in a hand direction opposite the forearm direction when the friction lock is in a locked configuration. In some such embodiments, the friction lock is further configured to allow movement of the bar with respect to the friction lock in the hand direction when the friction lock is in an unlocked configuration.

In some embodiments, the force applicator engages at least a portion of the dorsal side of the hand and applies the force to the hand in the first direction.

According to embodiments of the invention, a device for manipulating a hand of a user to provide palmar flexion or dorsiflexion assistance about a wrist of the user comprises a hand interface configured to engage the hand of the user; a forearm member configured to engage a forearm of the user, the forearm member operatively coupled to the hand interface at a joint, wherein the hand interface and the forearm member are configured to pivot about an axis defined by the joint as the user's wrist moves into palmar flexion or moves into dorsiflexion; and a restriction mechanism configured to restrict movement of the hand interface in a first direction corresponding to palmar flexion of the hand or a second direction opposite the first direction and corresponding to dorsiflexion of the hand.

In some embodiments, the restriction mechanism comprises a friction bar mechanism. In some such embodiments, the restriction mechanism further comprises a rotary mechanism operably coupled with the friction bar mechanism and configured to apply a second force to the hand interface as the rotary mechanism is activated, the second force urging the hand interface substantially in the first direction, thereby further providing palmar or dorsiflexion assistance to the wrist.

In other such embodiments, the friction bar mechanism is operatively coupled with the forearm member and the hand interface. In some such embodiments, the friction bar mechanism comprises a bar and a friction lock operatively coupled with the bar; the bar is operatively coupled to the hand interface and the friction lock is operatively coupled to the forearm member; and the friction lock is configured to allow movement of the bar with respect to the friction lock in a forearm direction and restricts movement of the bar with respect to the friction lock in a hand direction opposite the forearm direction when the friction lock is in a locked configuration. In some such embodiments, the friction lock is further configured to allow movement of the bar with respect to the friction lock in the hand direction when the friction lock is in an unlocked configuration.

According to embodiments of the invention, a method for manipulating body parts of a user, thereby providing extension or flexion assistance to the body parts about a joint includes engaging a first body part of the user using a first member of a body part engagement system; engaging a second body part of the user using a second member of the body part engagement system, wherein the second member is operatively coupled to the first member at a device joint and wherein the first member and second member are configured to pivot about an axis defined by the device joint as the user extends or flexes the first body part and/or second body part about the joint; and applying a force to a force applicator operatively coupled to the body part engagement system to rotate the first member with respect to the second member or to rotate the second member with respect to the first member and changing an angle formed therebetween, thereby providing the extension or flexion assistance to the first body part and/or second body part about the body.

In some embodiments, prior to applying the force, the first member and second member are configured in a first position relative to one another and wherein once the force has been applied, the first member and second member are in a second position relative to one another. In some such embodiments, the method also includes restricting movement of the first member and/or second member from the second position toward the first position.

In some embodiments, the method also includes restricting movement of the first body part from the first member. In some such embodiments, the method also includes restricting movement of the second body part from the second member.

In some embodiments, the body part engagement system moves from a first position to a second position when the force is applied. In some such embodiments, applying the force comprises applying a continuous or non-incremental force as the body part engagement system moves from the first position to the second position.

BRIEF DESCRIPTION OF THE DRAWINGS

Figure 1:
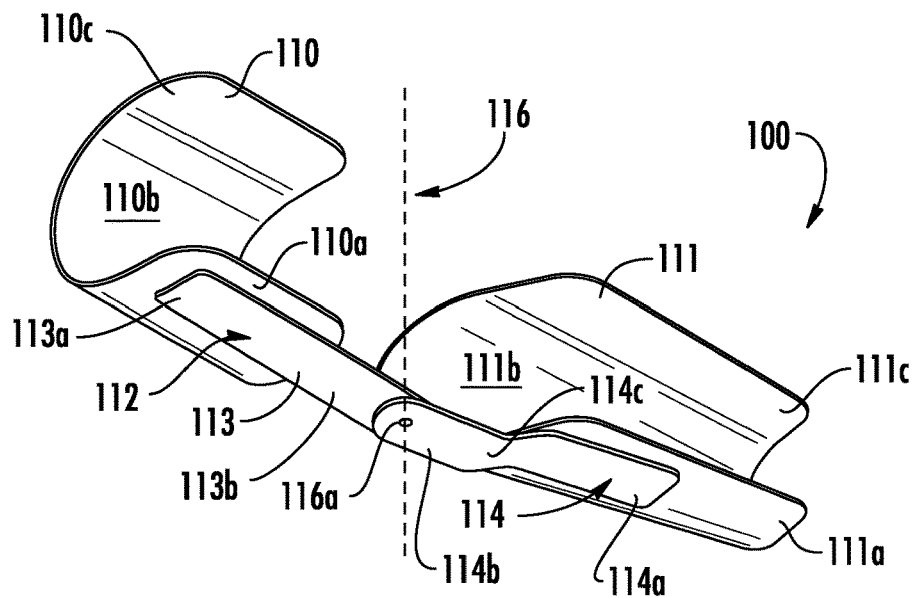
Figure 2:
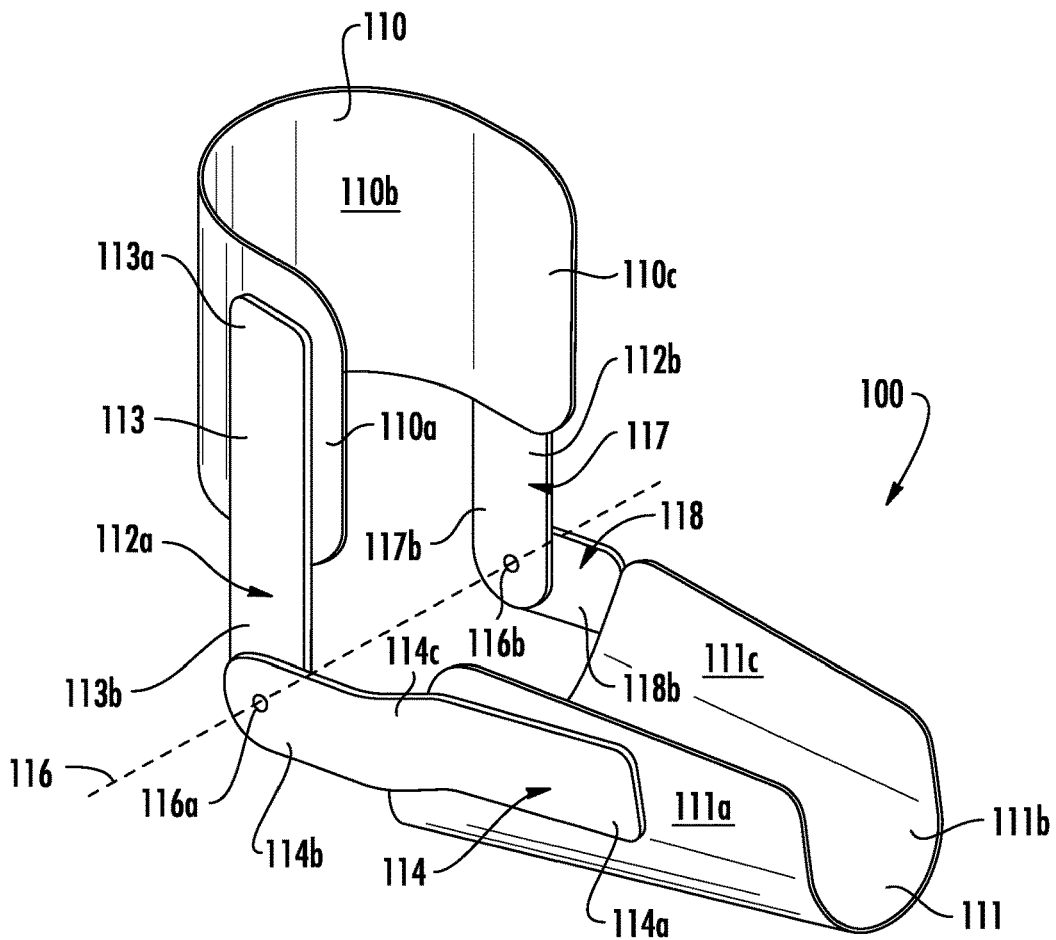
Figure 3:
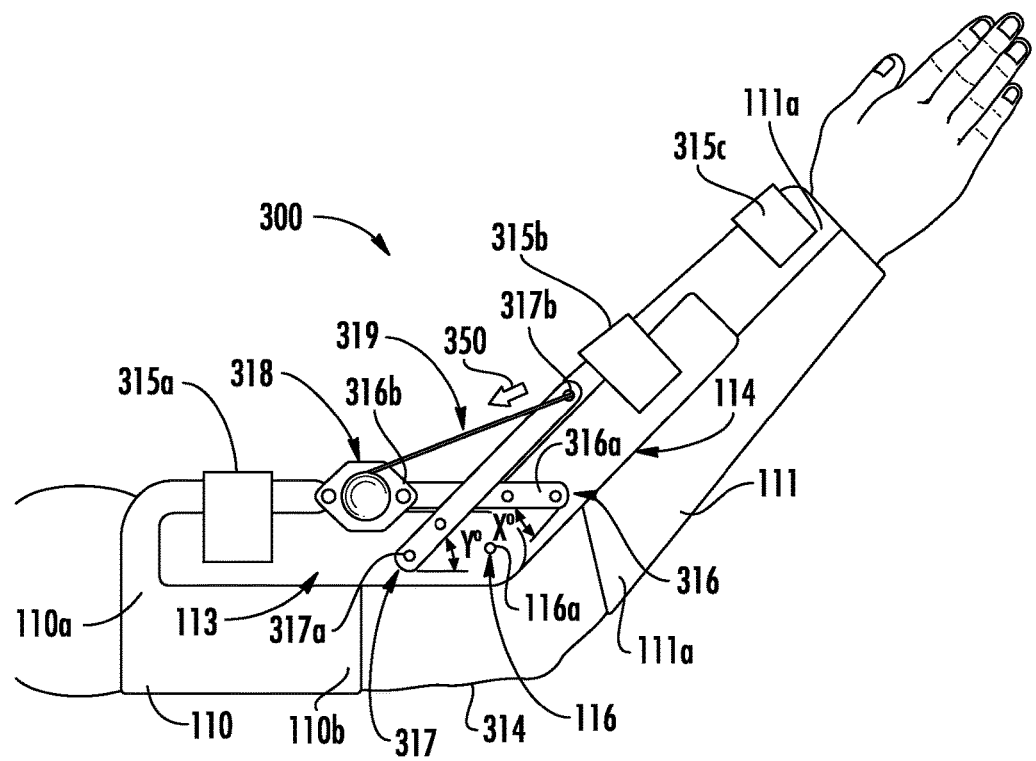
Figure 4:
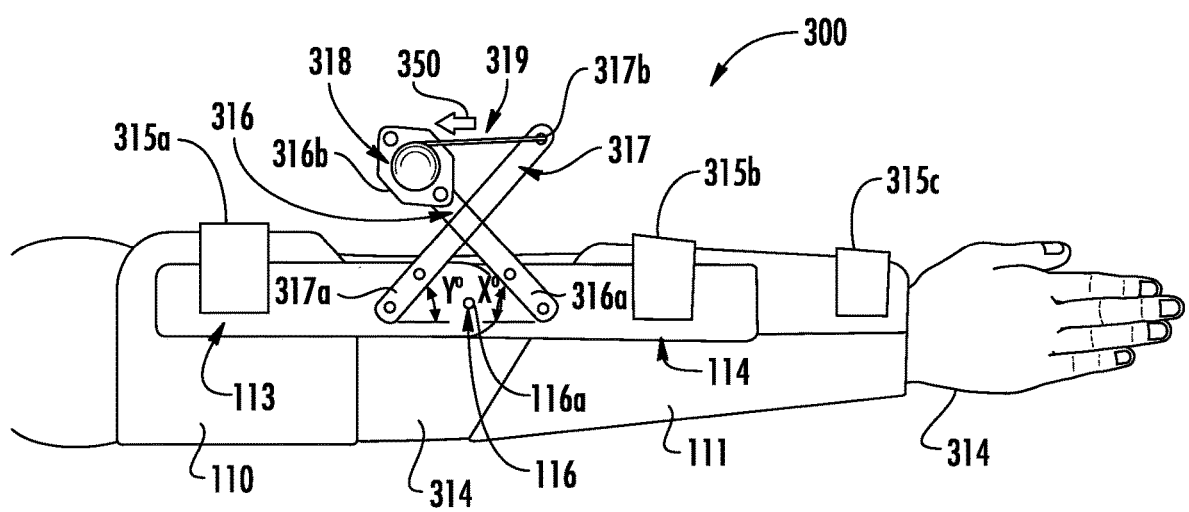
Figure 5A:
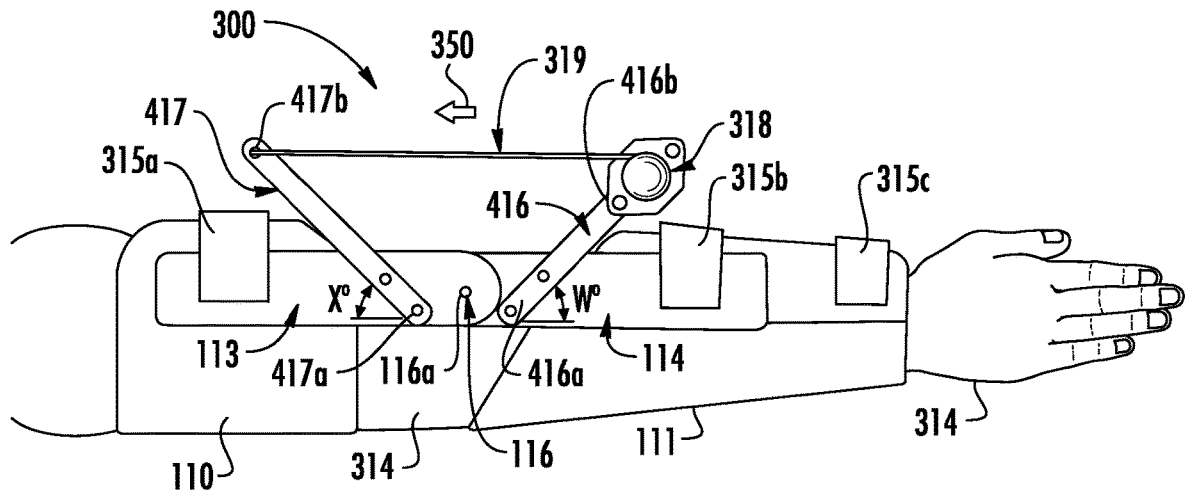
Figure 5B:
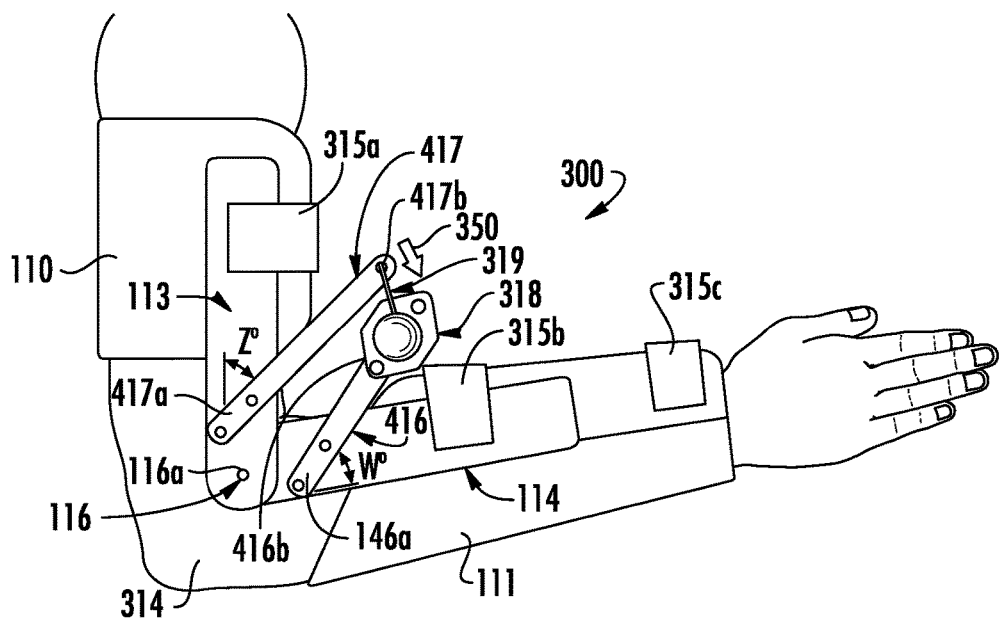
Figure 11A:
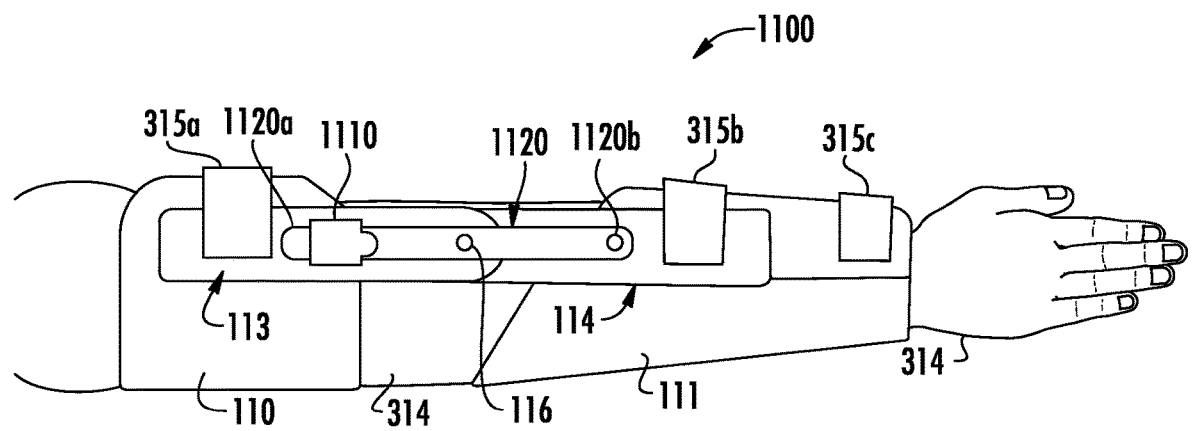
Figure 11B:
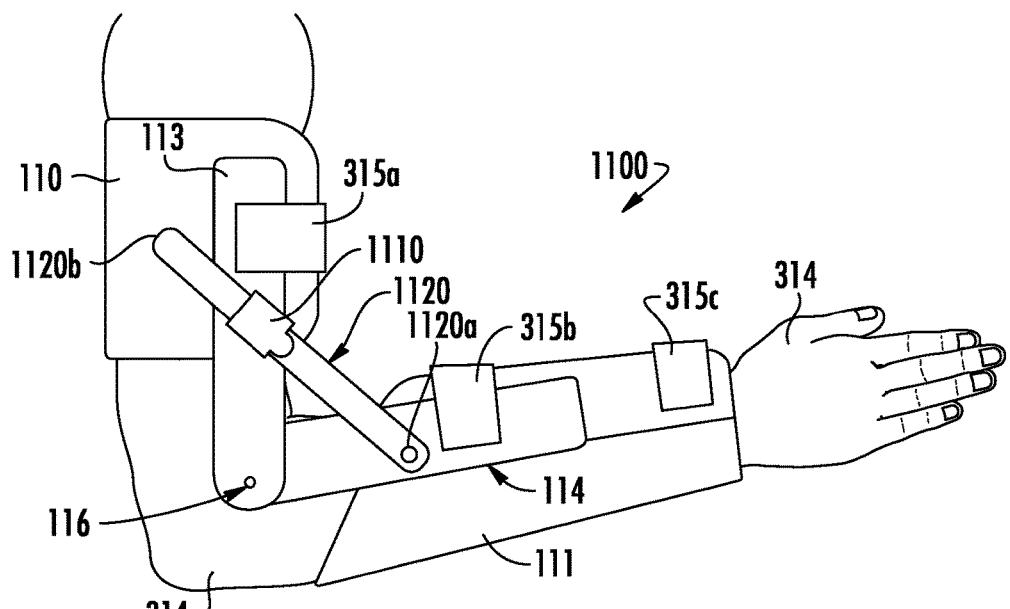
Figure 12:
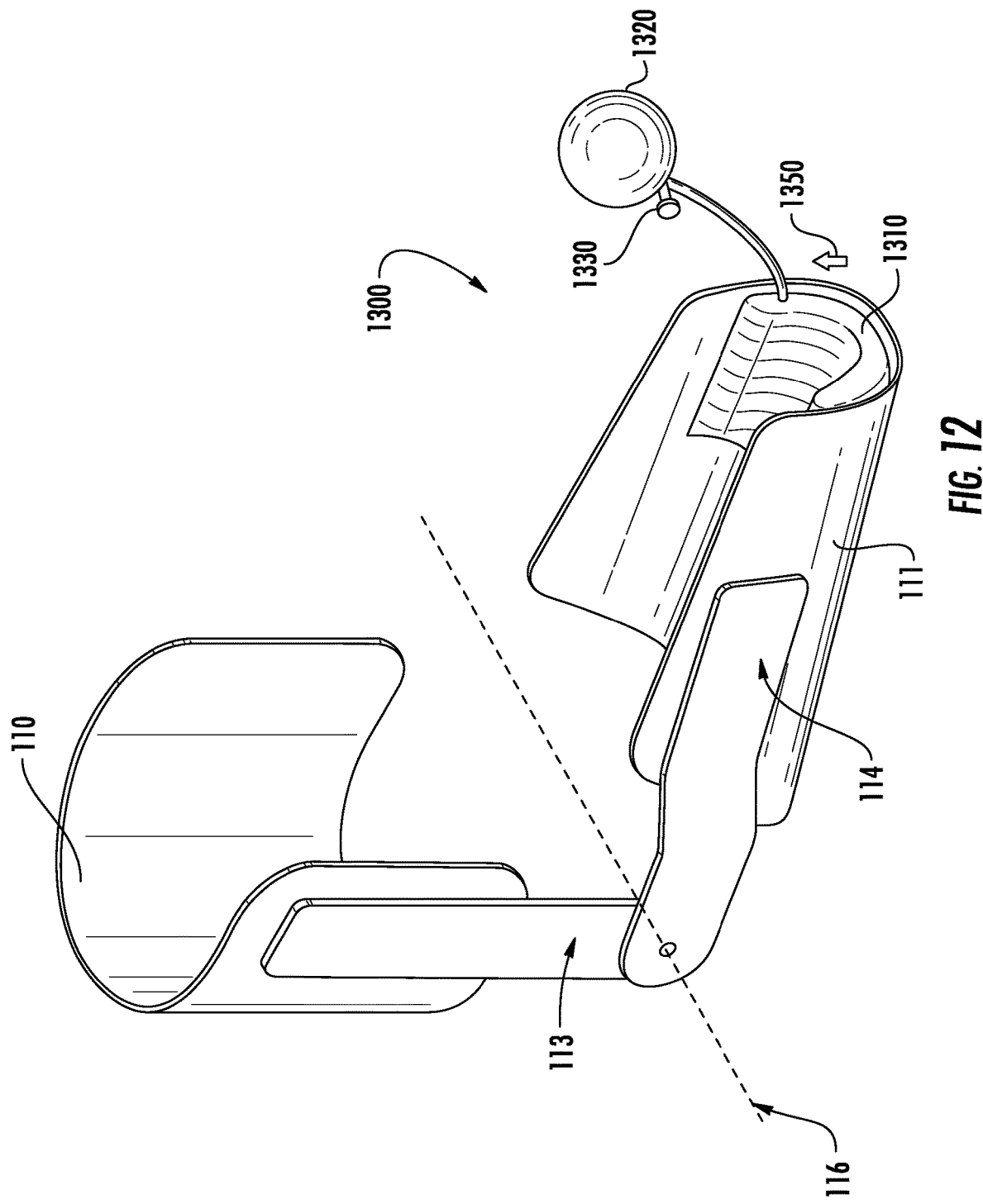
Figure 13:
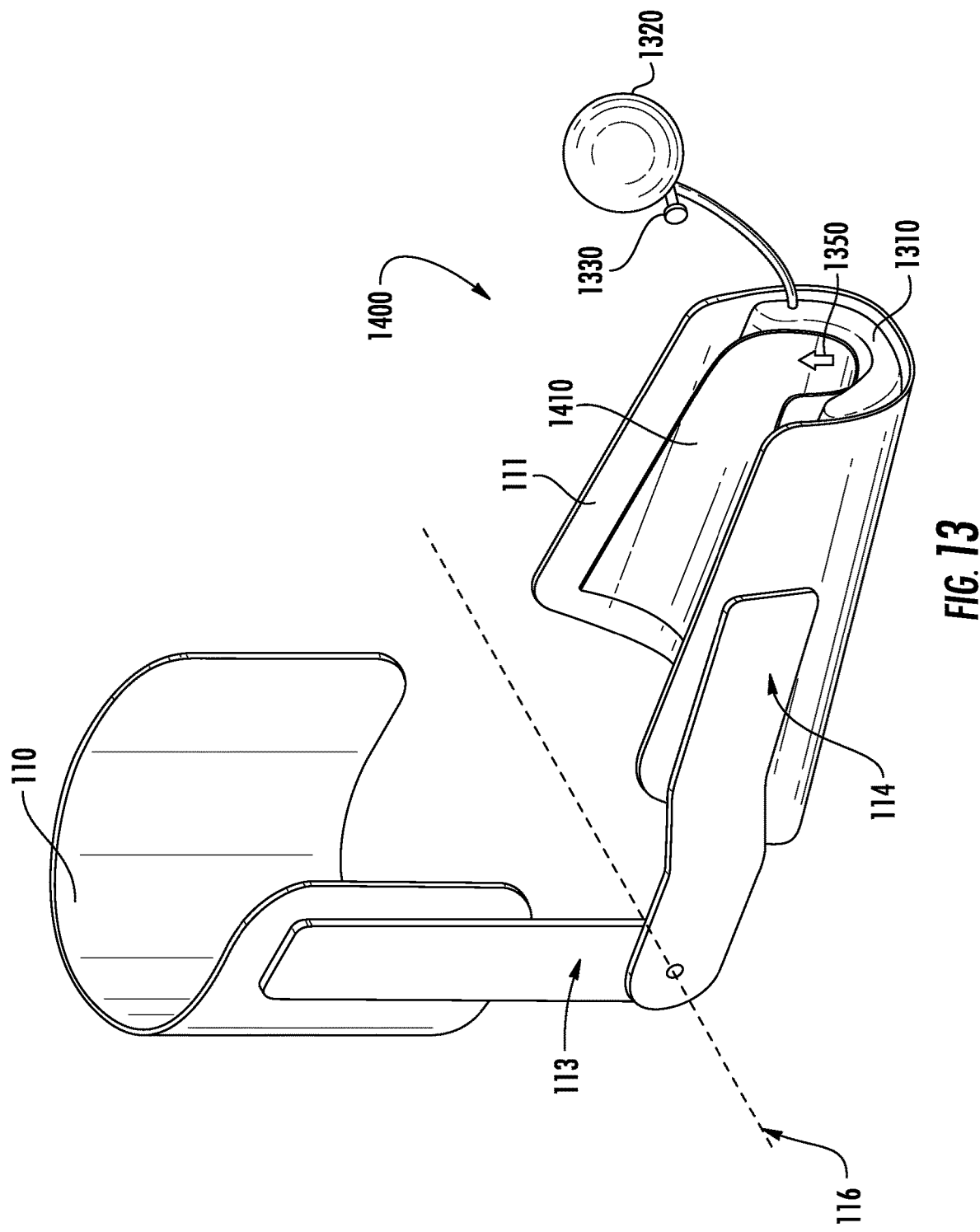
Figure 14:
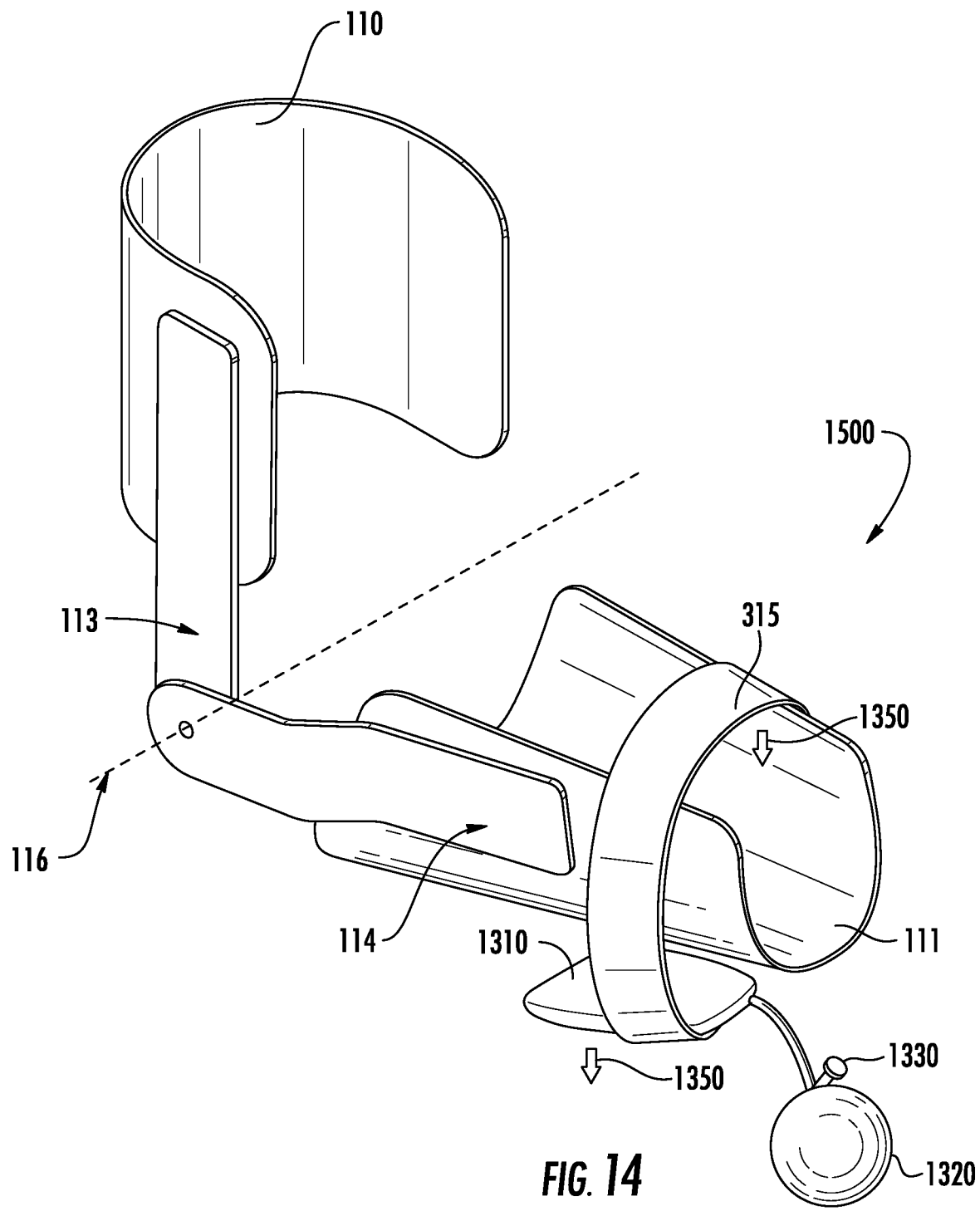
Figure 16:
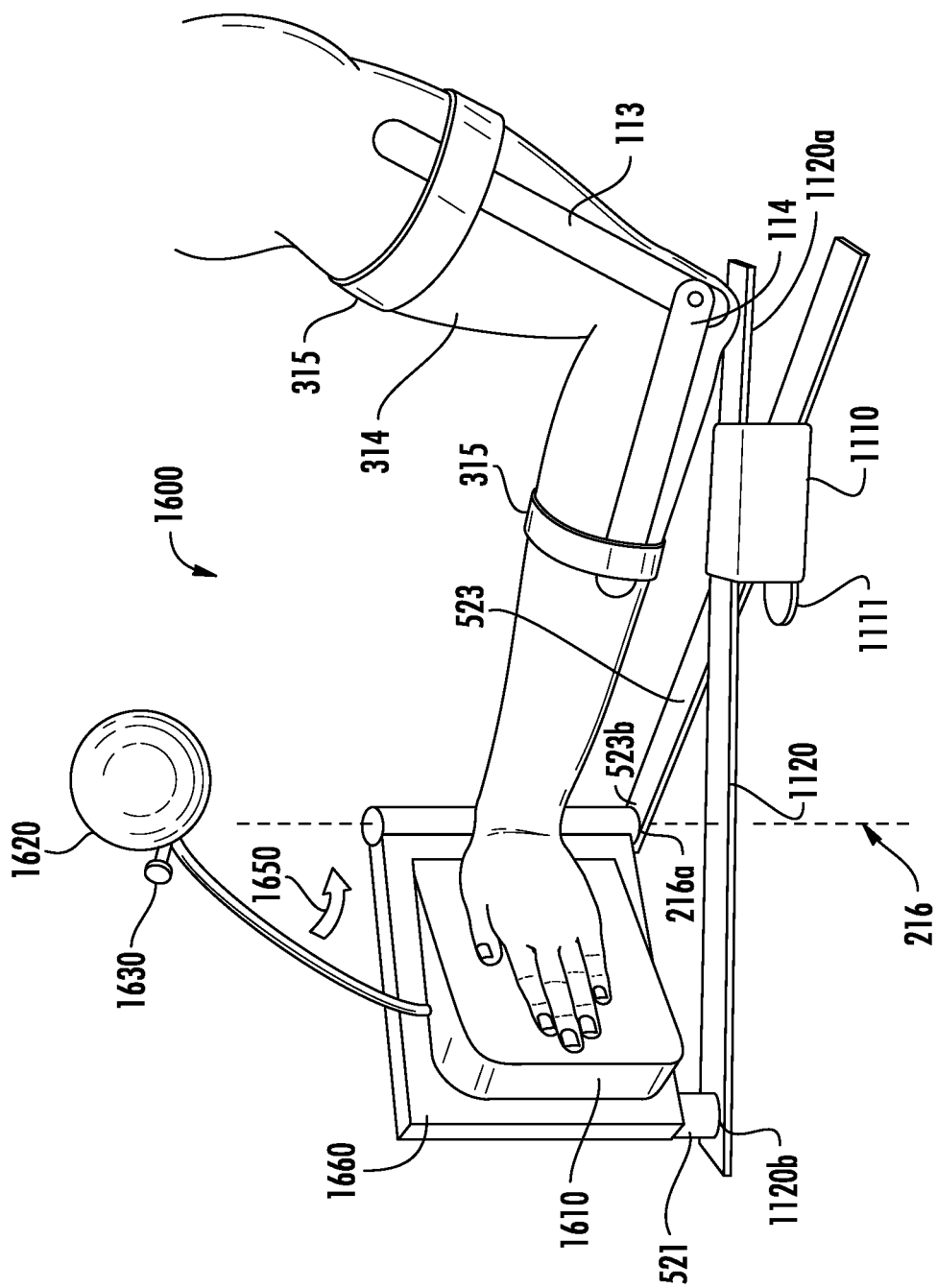
Figure 17:
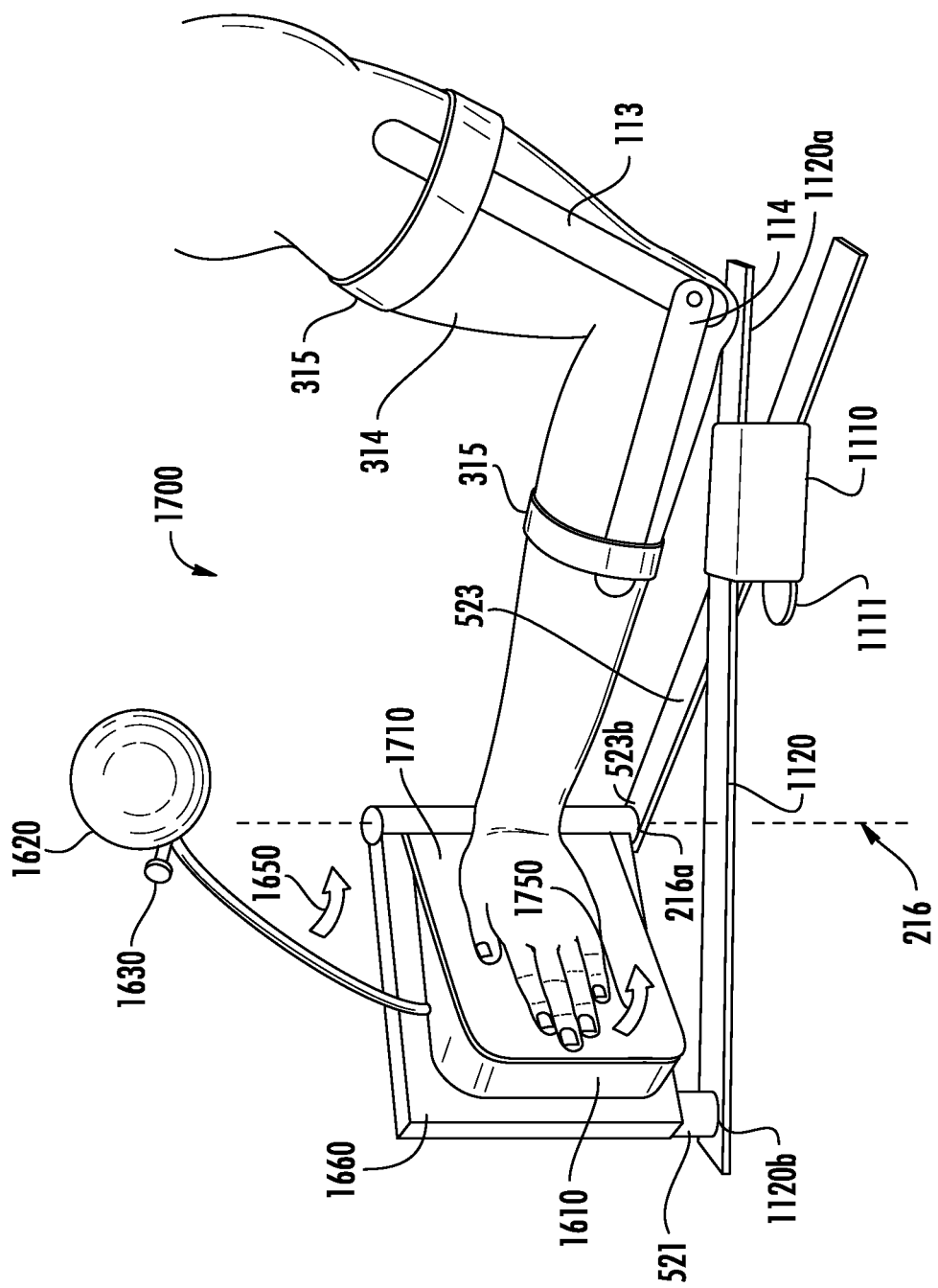
Figure 18:
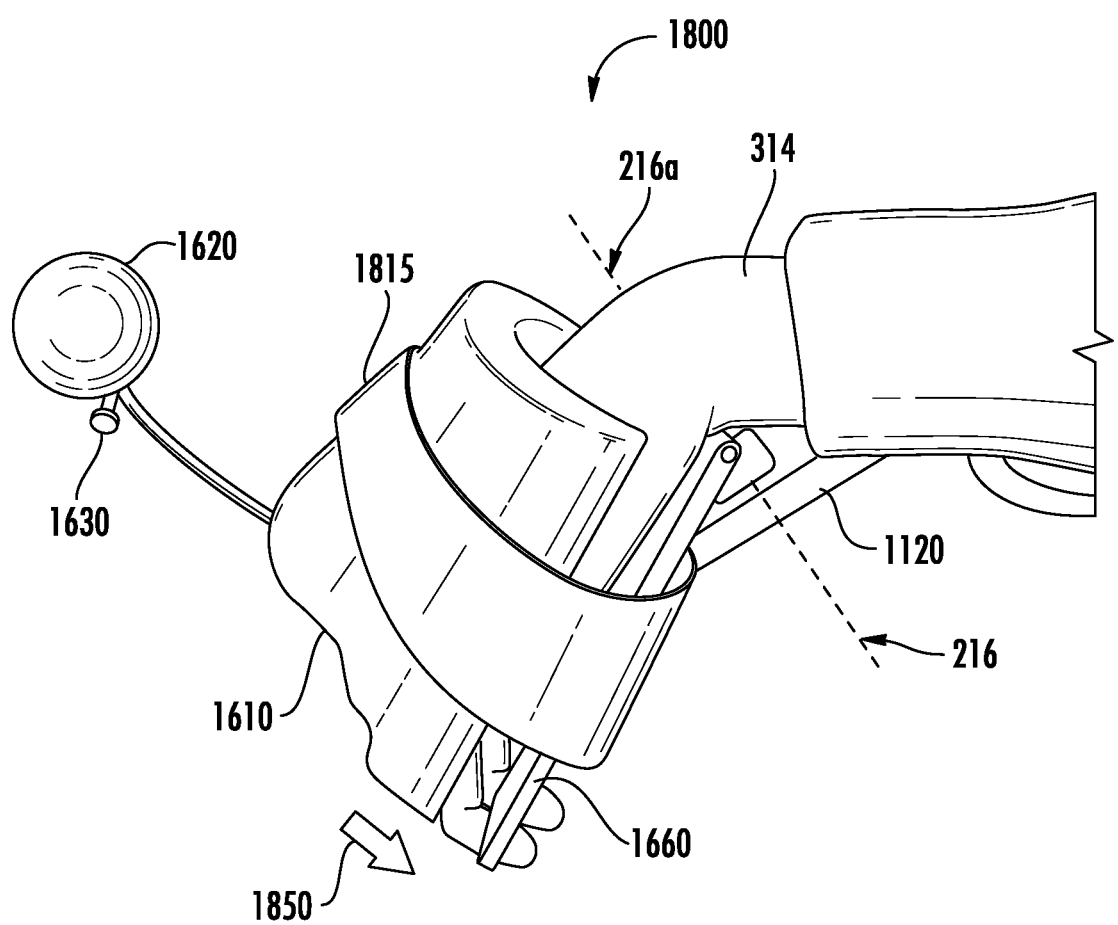
Figure 19:
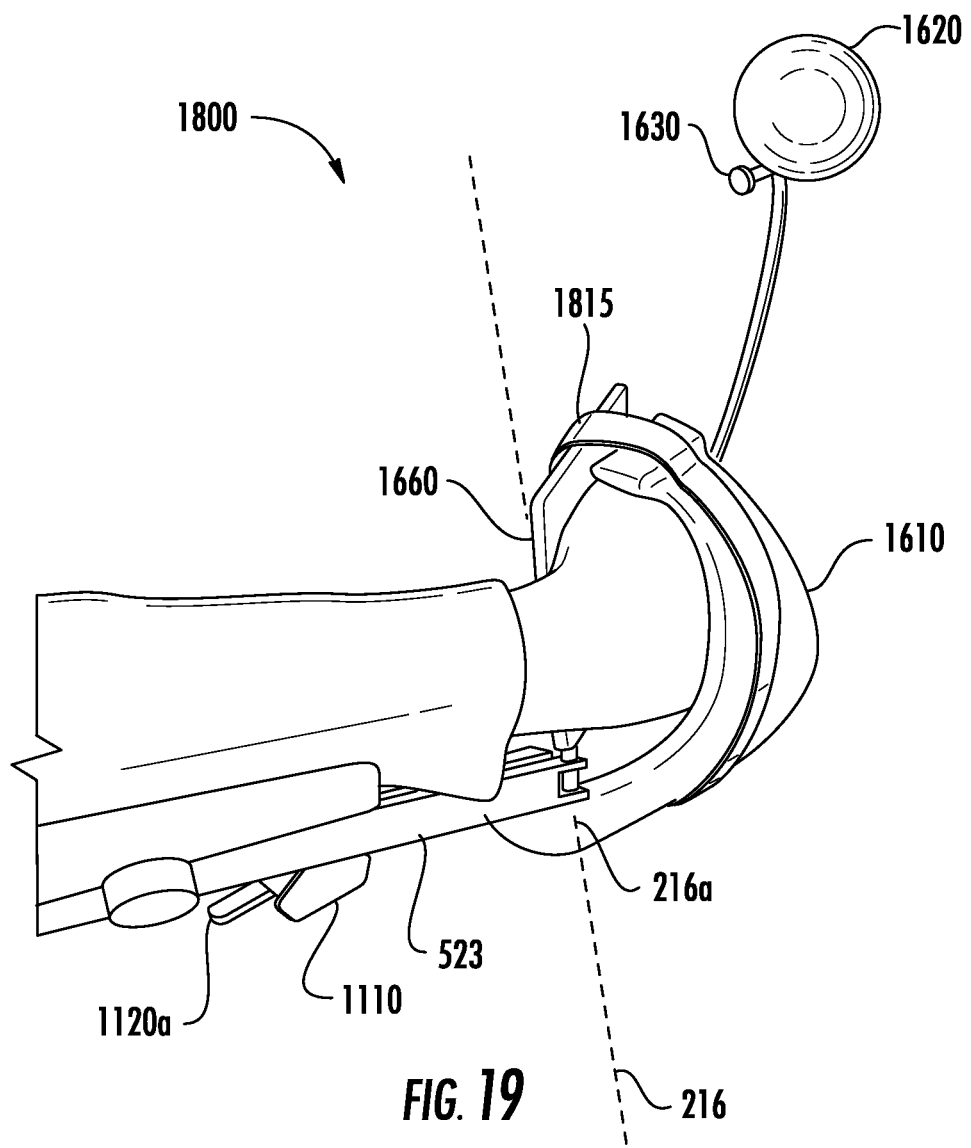
Figure 20:
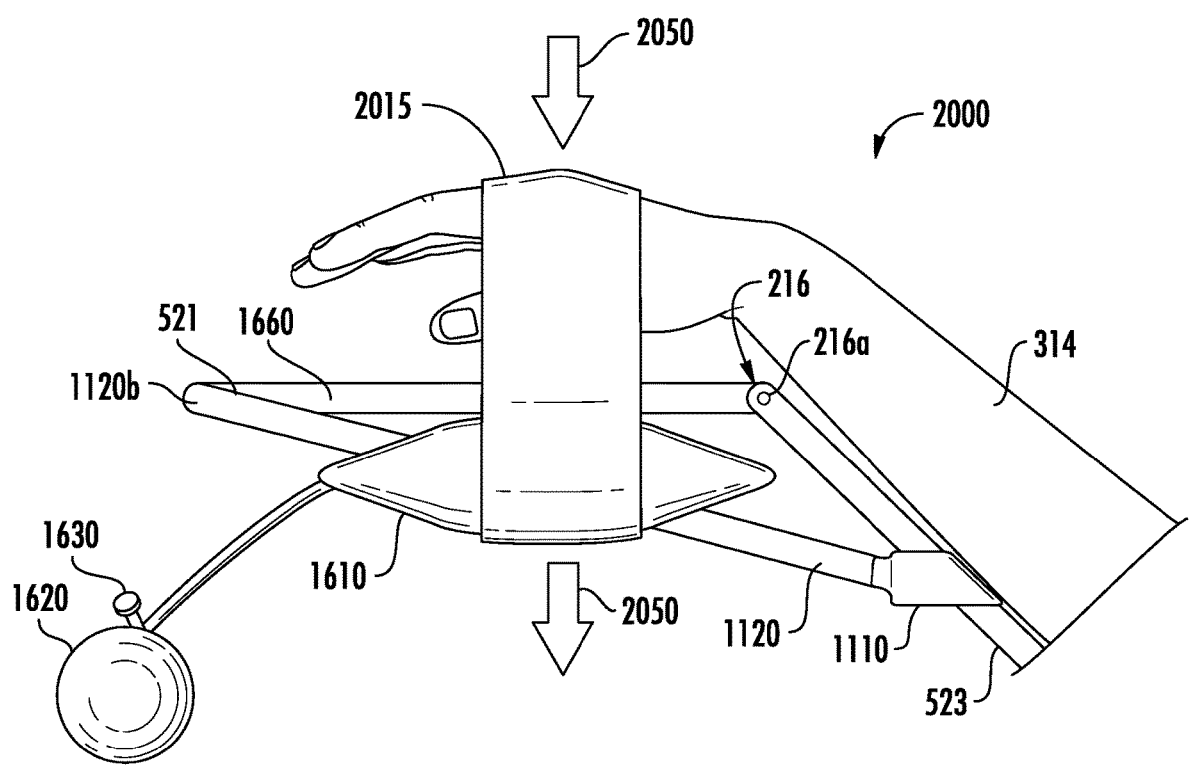
Figure 21:
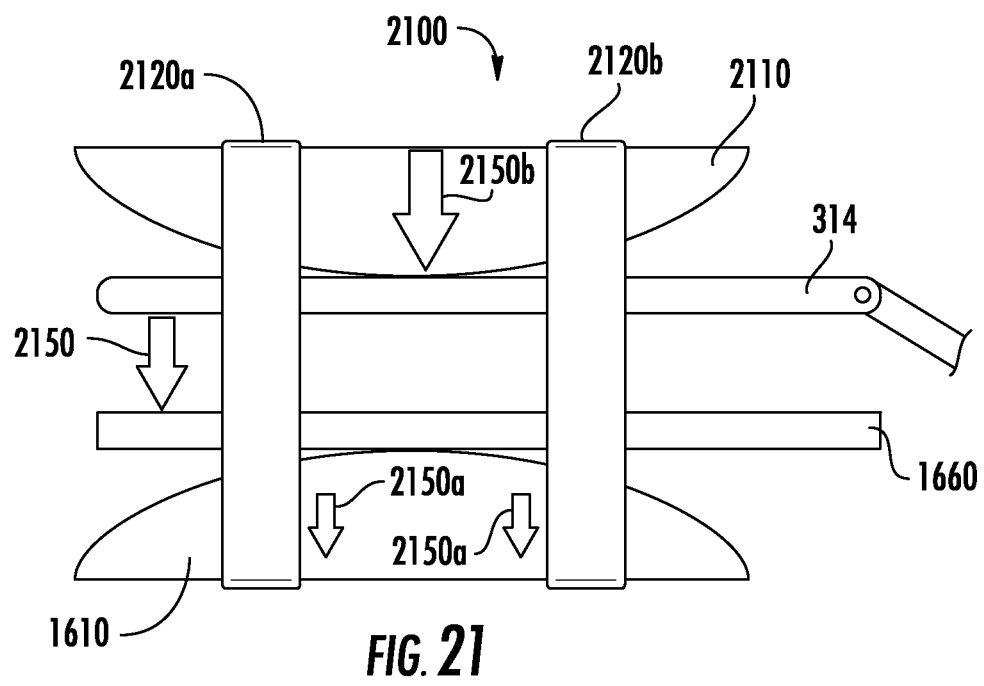

Having thus described embodiments of the invention in general terms, reference will now be made to the accompanying drawings, where:

FIG. 1 is a diagram illustrating a device for assisting with extension and flexion, in accordance with embodiments of the present invention;

FIG. 2 is a diagram illustrating a device for assisting with extension and flexion, in accordance with embodiments of the present invention;

FIG. 3 is a diagram illustrating a device for assisting with extension and flexion, in accordance with embodiments of the present invention;

FIG. 4 is a diagram illustrating a device for assisting with extension and flexion, in accordance with embodiments of the present invention;

FIGS. 5A and 5B are diagrams illustrating a device for assisting with extension and flexion, in accordance with embodiments of the present invention;

FIG. 6 is a diagram illustrating a device for assisting with extension and flexion, in accordance with embodiments of the present invention;

FIGS. 7A-7E are diagrams illustrating a friction lock, in accordance with embodiments of the present invention;

FIGS. 8A-8G are diagrams illustrating a force application mechanism, in accordance with embodiments of the present invention;

FIGS. 9A-9F are diagrams illustrating a force application mechanism in accordance with embodiments of the present invention;

FIGS. 10A-10H are diagrams illustrating a force application mechanism in accordance with embodiments of the present invention;

FIGS. 11A-11B are diagrams illustrating a device for assisting with extension and flexion, in accordance with embodiments of the present invention;

FIG. 12 is a diagram illustrating a device for assisting with extension and flexion, in accordance with embodiments of the present invention;

FIG. 13 is a diagram of a device for assisting with extension and flexion, in accordance with embodiments of the present invention;

FIG. 14 is a diagram of a device for assisting with extension and flexion, in accordance with embodiments of the present invention;

FIGS. 15A-15F are diagrams of a device for assisting with extension and flexion, in accordance with embodiments of the present invention;

FIG. 16 is a diagram of a device for assisting with extension and flexion, in accordance with embodiments of the present invention;

FIG. 17 is a diagram of a device for assisting with extension and flexion, in accordance with embodiments of the present invention;

FIG. 18 is a diagram of a device for assisting with extension and flexion, in accordance with embodiments of the present invention;

FIG. 19 is a diagram of a device for assisting with extension and flexion, in accordance with embodiments of the present invention;

FIG. 20 is a diagram of a device for assisting with extension and flexion, in accordance with embodiments of the present invention; and FIG. 21 is a diagram of a device for assisting with extension and flexion, in accordance with embodiments of the present invention.

DETAILED DESCRIPTION OF EMBODIMENTS OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Referring now to FIG. 1, an upper extremity support and range of motion device 100 is illustrated according to one embodiment of the present invention. It should be noted that as used herein the upper extremity support and range of motion device may be simply referred to as "the device" or "the arm engagement system". As shown in FIG. 1, the device 100 is defined by an upper extremity support structure that generally comprises an upper arm support member 110, a forearm support member 111, and at least one hinge assembly 112 operatively coupled to the support members 110, 111. The at least one hinge assembly 112 comprises two hinge plates 113, 114 attached to one another at an articulated joint 115 such that an upper hinge plate 113, and a lower hinge plate 114 pivot with respect to a first axis 116. As illustrated in FIG. 2, in some embodiments, the device 100 may comprise two hinge assemblies 112a, 112b positioned parallel to one another on opposite sides of the upper arm support member 110 and the forearm support member 111. In one embodiment, the device is positioned with respect to a joint (e.g. elbow joint) of an individual wearing the device (hereinafter, "the wearer") such that the upper arm support member 110 and the forearm support member 111 are attached to the upper arm and forearm of the individual, respectively, and the first axis 116 is parallel to a pivoting axis of the respective body part (e.g. the elbow). In exemplary embodiments, after the upper arm support member 110 and the forearm support member 111 have been suitably attached to the wearer's arm, the arm can bend at the elbow as the various members pivot relative to the first axis 116. The device 100 may include straps (not shown) that secure the device 100 to an arm of a user. The upper arm support member 110, the upper hinge plate 113, and at least one strap, collectively, may be referred to as the upper arm member. The forearm support member 111, the lower hinge plate 114, and at least one strap, collectively, may be referred to as the forearm member.

Referring again to FIG. 1, FIG. 1 illustrates a side oblique view of the upper extremity support and range of motion device 100. The device may be formed of various materials, including but not limited to a rigid plastic, wood metal, or other suitable materials such as any other erect material that provides needed support. It should be noted that the material of the device may vary based on the device component being constructed or the function of the device component. For example, the upper arm support member 110 and the forearm arm support member 111 may be constructed from a rigid plastic, and the hinge assembly 112 may be constructed from a metal. It should be understood that FIG. 1 is a simplified version of the invention. Padding of the upper arm support member 110 and forearm support member 111 may be optionally used if desired to increase comfort for the wearer. A plurality of straps or other attachment means may also be used as a method of securing the upper extremity support and range of motion device 100 to the wearer.

The upper arm support member 110 and forearm support member 111 utilize a cradle and/or cuff configuration. As shown in FIG. 1, in one embodiment, a first end 113a of the upper hinge plate 113 is attached to the exterior of the upper arm support member 110, proximate to the edge of a first end 110a of the upper arm support member 110, such that the hinge plate 113 is parallel to the first end 110a of the upper arm support member 110, and the hinge plate extends outward from the upper arm support member 110 towards the lower hinge plate 114. The first end 110a of the upper arm support member 110 extends away from the upper hinge plate 113 into a medial portion 110b of the upper arm support member such that the medial portion 110b of the upper arm support member 110 is positioned substantially beneath the upper hinge plate 113, and a second end 110c of the upper arm support member 110 is parallel to the first end 110a of the upper arm support member 110.

Likewise, in the embodiment of FIG. 1, a first end 114a of the lower hinge plate 114 is attached to the exterior of the forearm arm support member 111, proximate to the edge of a first end 111a of the forearm support member 111, such that the lower hinge plate 114 is parallel to the first end 111a of the forearm support member 111, and the lower hinge plate extends outward from the forearm support member 111 towards the upper hinge plate 113. The first end 111a of the forearm support member 111 extends away from the lower hinge 114 into a medial portion 111b of the forearm support member such that the medial portion 111b of the forearm support member 111 is positioned substantially beneath the lower hinge 114, and a second end 111c of the forearm support member 111 is parallel to the first end 111a of the forearm support member 110.

Furthermore, in the embodiment of FIG. 1, the upper hinge plate 113 and the lower hinge plate 114 may be operatively coupled to one another at a joint location 116a located relative to the first axis 116 (configured to align generally with the elbow joint of the wearer, in one embodiment) such that the first axis 116 extends through the joint location 116a. The joint location 116a may be defined by small apertures located within the ends 113b, 114b of the upper hinge plate 113 and the lower hinge plate 114, respectively. In such an embodiment, the upper hinge plate 113 and the lower hinge plate 114 may be operatively coupled to one another at the joint location 116a using one or more coupling mechanisms including, but not limited to, nuts, bolts, screws, adhesive, and the like. In one embodiment, the upper hinge plate 113 is defined by a flat plate, where the first end 113a of the upper hinge plate 113 is further defined by a squared shape, and the second end 113b of the upper hinge plate 113 is further defined by a rounded shape. The lower hinge plate 114 is defined by angled plate, where the first end 114a of the lower hinge plate 114 is further defined by a squared shape, the second end 114b of the lower hinge plate is further defined by a rounded shape, and a medial portion 114c of the lower hinge plate 114 extends outward and/or downward at an obtuse angle with respect to the first end of the forearm support member 111a towards the second end 114b of the lower hinge plate 114.

Referring again to FIG. 2, as previously mentioned FIG. 2 illustrates the use of a possible second hinge assembly along the first axis 116 to provide added stability and protection for the patient while wearing the upper extremity support structure. As such, the embodiments discussed herein may utilize either a single or double hinge assembly configuration. As shown in FIG. 2, in one embodiment, a first end 113a of the first upper hinge plate 113 is attached to the exterior of the upper arm support member 110, proximate to the edge of a first end 110a of the upper arm support member 110, such that the first upper hinge plate 113 is parallel to the first end 110a of the upper arm support member 110, and the first upper hinge plate 113 extends outward from the upper arm support member 110 towards a first lower hinge plate 114. The first end 110a of the upper arm support member 110 extends away from the first upper hinge plate 113 into a medial portion 110b of the upper arm support member such that the medial portion 110b of the upper arm support member 110 is positioned substantially beneath the first and second upper hinge plates 113, 117 respectively. A second end 110c of the upper arm support member 110 is parallel to the first end 110a of the upper arm support member 110, and the second upper hinge plate 117 is attached to the exterior of the upper arm support member 110, proximate to the edge of a second end 110c of the upper arm support member 110 such that the second upper hinge plate 117 is parallel to the second end 110c of the upper arm support member 110.

Likewise, in the embodiment of FIG. 1, a first end 114a of the lower hinge plate 114 is attached to the exterior of the forearm support member 111, proximate to the edge of a first end 111a of the forearm support member 111, such that the first lower hinge plate 114 is parallel to the first end 111a of the forearm support member 111, and the first lower hinge plate 114 extends outward from the forearm support member 111 towards a first upper hinge plate 113. The first end 111a of the lower arm support member 111 extends away from the first lower hinge plate 114 into a medial portion 111b of the forearm support member 111 such that the medial portion 111b of the forearm support member 111 is positioned substantially beneath the first and second lower hinge plates 114, 118 respectively. A second end 111c of the forearm support member 111 is parallel to the first end 111a of the forearm support member 111, and the second lower hinge plate 118 is attached to the exterior of the forearm support member 111, proximate to the edge of a second end 111c of the forearm support member 111 such that the second lower hinge plate 118 is parallel to the second end 111c of the forearm support member 111.

Furthermore, in the embodiment of FIG. 2, the second upper hinge plate 117 and the second lower hinge plate 118 may be operatively coupled to one another at a joint location 116b located relative to the first axis 116 (configured to align generally with the elbow joint of the wearer, in one embodiment) such that the first axis 116 extends through the joint location 116b. The joint location 116b may be defined by small apertures located within the ends 117b, 118b of the second upper hinge plate 117 and the second lower hinge plate 118, respectively. In such an embodiment, the upper hinge plate 113 and the lower hinge plate 114 may be operatively coupled to one another at the joint location 116b using one or more coupling mechanisms as previously discussed herein. In one embodiment, the second upper hinge plate 117 is defined by a flat plate, where the first end 117a of the upper hinge plate 117 is further defined by a squared shape, and the second end 117b of the upper hinge plate 117 is further defined by a rounded shape. The second lower hinge plate 118 is defined by angled plate, where the first end 118a of the lower hinge plate 118 is further defined by a squared shape, the second end 118b of the lower hinge plate is further defined by a rounded shape, and a medial portion 118c of the lower hinge plate 118 extends outward and/or downward at an obtuse angle with respect to the first end of the forearm support member 111a towards the second end 118b of the lower hinge plate 118.

Device for Providing Flexion and Extension of an Elbow

The following embodiments and additional components may be discussed in conjunction with the embodiments of FIGS. 1 and 2 for the purpose of providing flexion and extension of an arm about an elbow joint. As such FIG. 3 and FIG. 4 illustrate the device 100 in more detail than previously depicted in FIG. 1 and FIG. 2.

Extension of the Elbow: Elongate Members

FIG. 3 and FIG. 4 illustrate one possible variation of the device 300 designed to promote extension of an elbow of a wearer as the device pivots about the first axis 116, which is normal to the drawing surface. In such a configuration, the force application mechanism 318 and the force applicator 319 are each attached to the at least one hinge assembly 112 via elongate members 316, 317. In one embodiment, a member portion (proximal to the hinge assembly) of the elongate members 316, 317 may be coupled to ends of the upper hinge plate 113 and the lower hinge plate 114 via one or more apertures within the upper hinge plate 113 and the lower hinge plate 114, and attached with screws or rivets, or attached using other means. A plurality of straps 315 or other suitable means of attachment may be used as needed to secure the arm to the upper extremity support apparatus.

As shown in FIG. 3 and FIG. 4, in one embodiment, the upper arm support member 110 comprises one strap 315a located proximate to the end 110a, 110c of the upper arm support member 110 such that at least a portion of the strap 315a is affixed to the end 113a of the upper hinge plate 113, and the strap 315a is positioned perpendicularly with respect to the upper hinge plate 113. Likewise, the forearm support member 111 may comprise two straps 315b, 315c. The straps 315b, 315c may be located proximate to the ends 111a, 111c of the forearm support member 111 such that at least a portion of one strap 315b is affixed to the end 114a of the lower hinge plate 114, at least a portion of the second strap 315c is affixed directly to the ends 111a, 111c of the forearm support member 111 proximate to the wrist of the wearer 314, and the straps 315b, 315c are positioned perpendicularly with respect to the lower hinge plate 114. In such an embodiment, the straps 315a, 315b, 315c may be positioned parallel to one another at varied distances apart from one another.

In such an embodiment, the wearer 314 may secure the upper arm support member 110 and forearm support member 111 to their upper arm and forearm, respectively, as shown in at least FIG. 3. The wearer 314 may then operate the force application mechanism 318 which may subsequently result in activating the force applicator 319 to the device 300. This activation may be done by the other hand of the user, or by a second party. In one embodiment, the force application mechanism 318 is a dial that allows for a force to be applied by a force applicator 319 as said force applicator may be wound around the dial by the other hand of the user or by a second party, although other force application means may be used.

Referring to FIG. 3, the elongate member 316 may be attached near the end 114b of the lower hinge plate 114, proximate to the joint location 116a, and extend upward, relative to the bottom of the hinge plate 114, at an acute angle "X" facing inward towards the joint location 116a. Similarly, the elongate member 317 may be attached near the end 113b of the upper hinge plate 113, proximate to the joint location 116, and extend upward, relative to the bottom of the hinge plate 113, at an acute angle "Y" facing inward towards the joint location 116a. In such an embodiment, the elongate members 316, 317 cross at a medial point such that the elongate member 317 overlays the exterior of the elongate member 316, and the elongate member 316 is adjacent to the interior of the elongate member 317 such that at least a portion of its inner surface is proximate to the body of the wearer. In some embodiments, one or more of the elongate members 316, 317 may be bent, curved, or otherwise configured such that the elongate members 316, 317 may overlay each other without touching. In some embodiments, the elongate members 316, 317 are not hinged together so the medial point may move with respect to the positioning of the two elongate members 316, 317.

Continuing the description of the embodiment illustrated in FIG. 3, a force application mechanism 318 may be operatively coupled to a distal point 316b of the elongate member 316 at a significant distance from the lower hinge plate 114. A force applicator 319 may extend from the force application mechanism 318 and is operatively coupled at the other end to a distal position 317b on the elongate member 317 at a significant distance from the upper hinge plate 113. In such a configuration, activating the force application mechanism 318 shortens the length of the force applicator 319, and therefore applies a force 350 drawing the position 317b of the elongate member 317 towards the force application member 318 and its respective position 316b on elongate member 316. Such a force 350 causes a torque, or moment, with respect to the joint 116a of the brace, and therefore the elbow of the wearer 314, and causes the device 300 to rotate about the axis 116, moving the elbow from a first position to a second, more extended position. Using the elongate members 316, 317, as described, provides a longer moment-arm (the distance from a pivoting axis and a point where force is applied), and therefore more torque, than simply attaching the force application mechanism 318 and/or the force applicator 319 to the hinge assembly of the device 300.

In one embodiment (not pictured), the force application member 318 may instead be operatively coupled to the elongate member 317 and the end of the force applicator 319 may instead be operatively coupled to the elongate member 316. Such a configuration changes the directionality of the force 350 applied to the device 300, but does not change the result of applying the force as the ends of the elongate members 316, 317 will still approach each other as the force 350 is applied, causing the elbow of the wearer 314 to extend.

FIG. 4 illustrates a second position of the elbow extension embodiment of the device 300 previously discussed. The elongate member 316 is still attached to the same point 114b of the lower hinge plate 114, and maintained the acute angle "X" facing inward towards the joint location 116a. Similarly, the elongate member 317 is still attached to the same point 113b of the upper hinge plate 113, and maintained the acute angle "Y" facing inward towards the joint location 116a. As illustrated by FIG. 4's differences to FIG. 3, the force applicator 319 is significantly shortened and the joint angle is significantly greater, showing an extension of the elbow of the wearer 314.

In the embodiment of FIG. 3 and FIG. 4, the force application mechanism 318 may be utilized to shorten the force applicator 319 with respect to the elongate members 316, 317, such that when the force applicator 319 is substantially shortened, the hinge assembly 112 is straightened about the axis 116, extending the elbow of the wearer 314. In one embodiment, the force application mechanism 318 has a means of shortening the force applicator 319 as well as a means to resist or prevent extension of the force applicator 319 such that the force applicator 319 may only be shortened, and the elbow of the user 314 may therefore only extend. In one embodiment, an incremental force may be applied to the device by the force application mechanism 318 and the force applicator 319. In such an embodiment, the force applicator 319 may be shortened in increments such that the force resulting from each increased increment incrementally straightens the hinge assembly and, subsequently straightens or causes extension the elbow of the wearer 314. In another embodiment, a continuous force may be applied to the device by the force application mechanism 318 and the force applicator 319. In such an embodiment, the force applicator 319 may be continuously shortened such that the resulting force continuously straightens the hinge assembly and, subsequently straightens or causes extension of the elbow of the wearer 314. In either embodiment, the force may be applied in one direction with respect to the force application mechanism 318, and the force application mechanism 318 may comprise a means for releasing the force with a release 1111 and subsequently permitting lengthening of the force applicator 319 and allowing free range of motion of the elbow of the wearer 314.

As illustrated in FIGS. 5A and 5B, the relative orientation of the elongate members 416, 417 may be changed, causing the device 500 to promote flexion of the elbow via the manipulation of the force application mechanism 318. In some embodiments of the invention, the device 300 and device 500 are separate devices. In some embodiments, the device 300, 500 may be a single device where the elongate members 316, 317 (or 416, 417) may be repositioned to create flexion or extension.

Referring to FIG. 5A, the elongate member 416 may be attached near the end 114b of the lower hinge plate 114, proximate to the joint location 116a, and upward relative to the bottom of the hinge plate 114 at an angle "W" facing outward from the joint location 116a. Similarly, the elongate member 417 may be attached to the end 113b of the upper hinge plate 113 proximate to the joint location 116a, and upward relative to the bottom of the hinge plate 113 at an angle "Z" facing outward from the joint location 116a. In such an embodiment, the elongate members 416, 417 do not cross or intersect.

Continuing the description of the embodiment illustrated in FIG. 5A, a force application mechanism 318 may be operatively coupled to an elongate member 416 at a significant distance from the lower hinge plate 114. A force applicator 319 may extend from the force application mechanism 318 and is operatively coupled at the other end to a position 417b on the elongate member 417 at a significant distance from the upper hinge plate 113. In such a configuration, activating the force application mechanism 318 shortens the length of the force applicator 319, and therefore applies a force 350 drawing the position 417b of the elongate member 417 towards the force application member 318 and its respective position 416b on elongate member 416. Such a force 350 causes a torque, or moment, with respect to the joint 116a of the brace, and therefore the elbow of the wearer 314, and causes the device 500 to rotate about the axis 116, moving the elbow from a first position to a second, more flexed position. Using the elongate members 416, 417, as described, provides a longer moment-arm (the distance from a pivoting axis and a point where force is applied), and therefore more torque, than simply attaching the force application mechanism 318 and/or the force applicator 319 to the hinge assembly of the device 300.

In one embodiment (not pictured), the force application member 318 may instead be operatively coupled to the elongate member 417 and the end of the force applicator 319 may instead be operatively coupled to the elongate member 416. Such a configuration changes the directionality of the force 350 applied to the device 500, but does not change the result of applying the force as the ends of the elongate members 416, 417 will still approach each other as the force 350 is applied, causing flexion of the elbow of the wearer 314.

FIG. 5B illustrates a second position of the elbow flexion embodiment of the device 500 previously discussed. The elongate member 416 is still attached to the same point 114b of the lower hinge plate 114, and still maintains the angle "W" facing outward from the joint location 116a. Similarly, the elongate member 417 is still attached to the same point 113b of the upper hinge plate 113, and still maintains the angle "Z" facing outward from the joint location 116a. As illustrated by FIG. 5B's differences to FIG. 5A, the force applicator 319 is significantly shortened and the joint angle is significantly smaller, showing a flexion of the elbow of the wearer 314.

One alternative embodiment to FIGS. 5A and 5B, involves a single elongate member attached to one of the hinge plate assemblies 113, 114. For example, a force application mechanism 318 may be positioned directly on the upper hinge plate 113, a force applicator 319 may extend from the force application mechanism 318, and attach at the other end to a point 416b on the single elongate member 416. Of course, the force application member 318 and the end of the force applicator 319 may switch positions such that the force application member 318 is operatively coupled to the elongate member 416 and the force applicator is operatively coupled directly to the hinge assembly 112. In another embodiment, the elongate member 417 is located on the upper hinge assembly 112, the force application mechanism 318 is operatively coupled directly to the lower hinge assembly 114, and the force applicator 319 extends from the force application mechanism 318 and is operatively coupled at the other end to the position 417b on the single elongate member 417. Again, the force application member 318 and the end of the force applicator 319 may switch positions such that the force application member 318 is operatively coupled to the elongate member 417 and the force applicator is operatively coupled directly to the lower hinge assembly 114.

In the embodiment of FIG. 5A and FIG. 5B, the force application mechanism 318 may be utilized to shorten the force applicator 319 with respect to the elongate members 416, 417, such that when the force applicator 319 is substantially shortened a force is applied to the device which enables the hinge assembly 113, 114 to rotate about the axis 116, flexing the elbow of the wearer 314. In one embodiment, the force application mechanism 318 has a means of shortening the force applicator 319 as well as a means to resist or prevent extension of the force applicator 319 such that the force applicator 319 may only be shortened, and the elbow of the user 314 may therefore only flex. In one embodiment, an incremental force may be applied to the device by the force application mechanism 318 and the force applicator 319. In such an embodiment, the force applicator 319 may be shortened in increments such that the force resulting from each increased increment incrementally pivots the hinge assembly about the axis 116, and subsequently flexes or causes flexion of the elbow of a wearer 314. In another embodiment, a continuous force may be applied to the device by the force application mechanism 318 and the force applicator 319. In such an embodiment, the force applicator 319 may be continuously shortened such that the resulting force continuously pivots the hinge assembly 112, causing flexion of the elbow of the wearer 314. In either embodiment, the force may be applied in one direction with respect to the force application mechanism 318, and the force application mechanism 318 may comprise a means for releasing the force (e.g. a release button) and subsequently permit lengthening the force applicator 319 and allow a free range of motion of the elbow of the wearer 314.

While some embodiments of the device disclosed herein comprise a first arm member, a second arm member, and a hinge or pivot, some embodiments do not comprise a pivoting connection between the first and second arm members. In one embodiment, no hinge is provided between the first and second arm members such that the elbow of the user 314 is the only hinged aspect of the device. In some embodiments, a living hinge may be provided, where the living hinge is a rubber or elastic connector between the two arm members that is very flexible in every direction, exerting very little force on the user such that the user's elbow comprises the main rotational element of the assembly. In one embodiment, the two arm members are connected by more than one pivoting hinge. In such an embodiment, the two or more hinges may pivot about the same axis, pivot along parallel axes to each other, or pivot along non-parallel axes. In one embodiment comprising multiple hinges, the multidirectional configuration of the hinges may allow for a full range of motion about the elbow, and not the unidirectional range of motion allowed by a single hinge.

FIG. 6 illustrates one non-hinged embodiment 600 of a slide juncture 610 between a first and second arm member 620, 630. As illustrated in FIG. 6, the first arm member 620 and the second arm member 630 intersect at a general slide juncture 610. The first arm member comprises an aperture 640 that traverses the width of the arm first member 620. The second arm member 630 is slidably positioned such that one section of the second arm member 630 passes through the aperture 640 of the first arm member 620. The second arm member 630 may rotate, slide, extend, retract, and generally freely move within and throughout the aperture 640. The second arm member comprises stoppers 630a, b, c, and d that restrict the movement of the second arm member 630 to prevent the second arm member 630 from completely sliding through the aperture 640 of the first arm member 620 and thereby ceasing to create a general slide juncture 610 between the first and second arm members 620, 630. Such a configuration allows minimally restrictive movement about a joint of a user without requiring a hinge or joint to connect the arm members 620, 630. In one embodiment, the arm members 620, 630 are the upper hinge assembly 113 and the lower hinge assembly 114 of embodiments of the invention described herein.

Figure 7B:
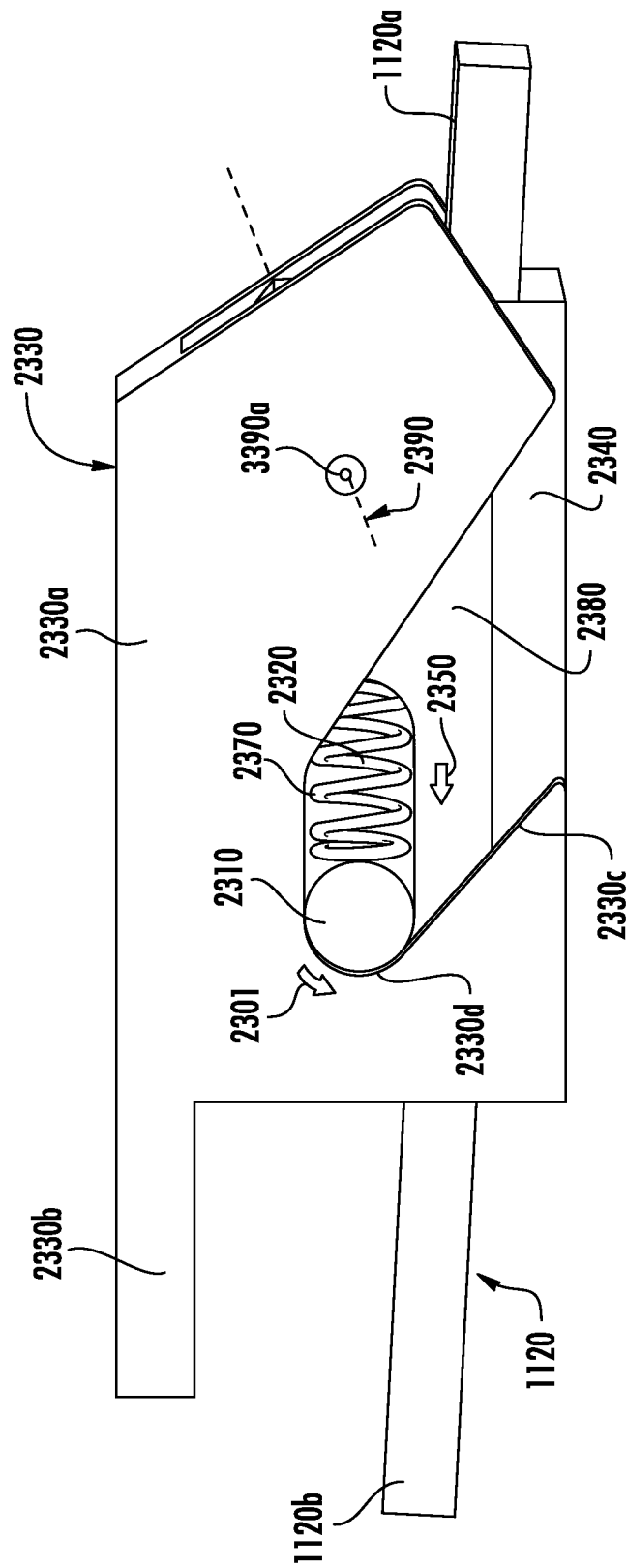

FIGS. 7A-E illustrate an embodiment of a friction lock 1110 device, as used throughout this disclosure. Referring to FIG. 7A, the friction lock 1110 comprises a base 2340, a main body 2380, a latch 2330, a roller 2310, a spring 2320, a recess 2370, and a pivot pin 2390a. The friction lock 1110 may engage a sliding bar 1120, as described in several embodiments herein. Each of these elements may be comprised of a metal, solid plastic, wood, or other substantially rigid material. The spring may be any type of coiled spring that may compress and expand. The sliding bar enters an alley 2370a that is approximately the width and height of the sliding bar 1120. The alley 2370a may be formed between the base 2340 and the main body 2380. The base 2340 and the main body 2380 may be connected by bolts, screws, nails, glue, adhesive, or in any other manner that secures the two parts together. In another embodiment, the base 2340 and the main body 2380 may be one solid piece and therefore the alley 2370a may pass through the combined base/main body member of the friction lock 1120. In one embodiment, the base 2340 of the friction lock 1110 is attached to a rigid surface such that the friction lock 1110 is securely fastened to the surface. In another embodiment, the base 2340 of the friction lock 1120 is slidably fastened to a surface such that the friction lock may slide along the surface without being separated from the surface. In one embodiment, the base 2340 of the friction lock 1110 is pivotally connected to a surface such that the entire friction lock 1110 may pivot about an axis perpendicular to the surface without separating from the surface.

The main body 2380 comprises a recess 2370, which houses a spring 2320 and a roller 2310. The roller 2310 is always in contact with the sliding bar 1120 which is positioned underneath the roller 2310. The spring 2320 comprises a first end 2320a that engages the roller 2310, and a second end 2320b that engages main body 2380 at a wall 2380a. The engagement of the main body 2380 and the second end of the spring 2320b at the wall 2380a is illustrated in the cross-section depiction of the friction lock shown in FIG. 7C. The spring provides a force 2350 on the roller 2310, causing the roller 2310 to roll away from the wall 2380a. The pivot pin 2390a runs through the main body 2380 and defines a pivot axis 2390. The latch 2330 is operatively coupled to the main body 2380 via the pivot pin 2390a such that the latch 2330 may rotate about the pivot axis 2390. The latch comprises a body 2330a, a lever 2330b, an unlocking interface 2330c, and a locking interface 2330d. The unlocking interface 2330c and the locking interface 2330d are illustrated with bolded lines, and generally comprise the surface area at the bolded areas.

Figure 7C:
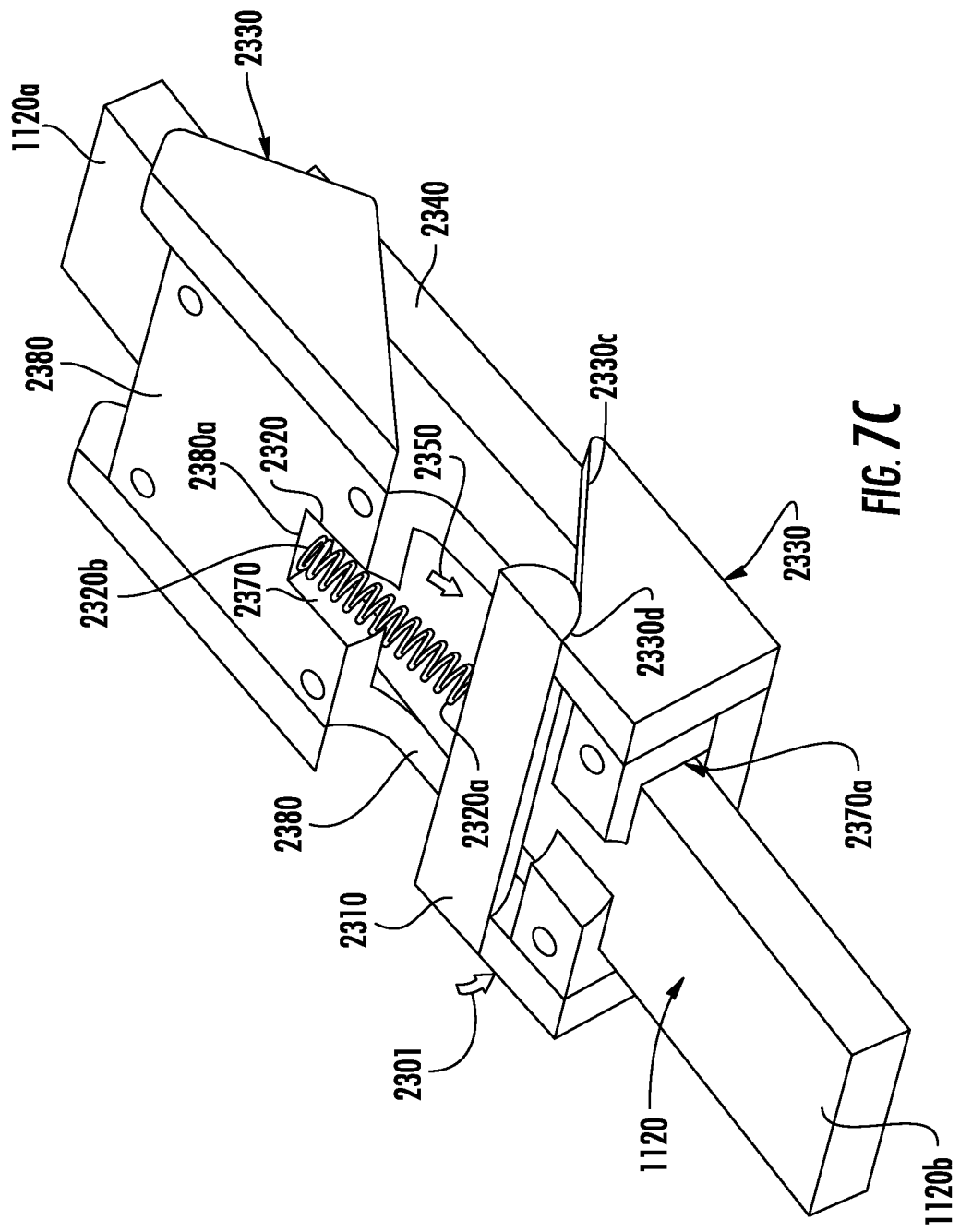
Figure 7E:
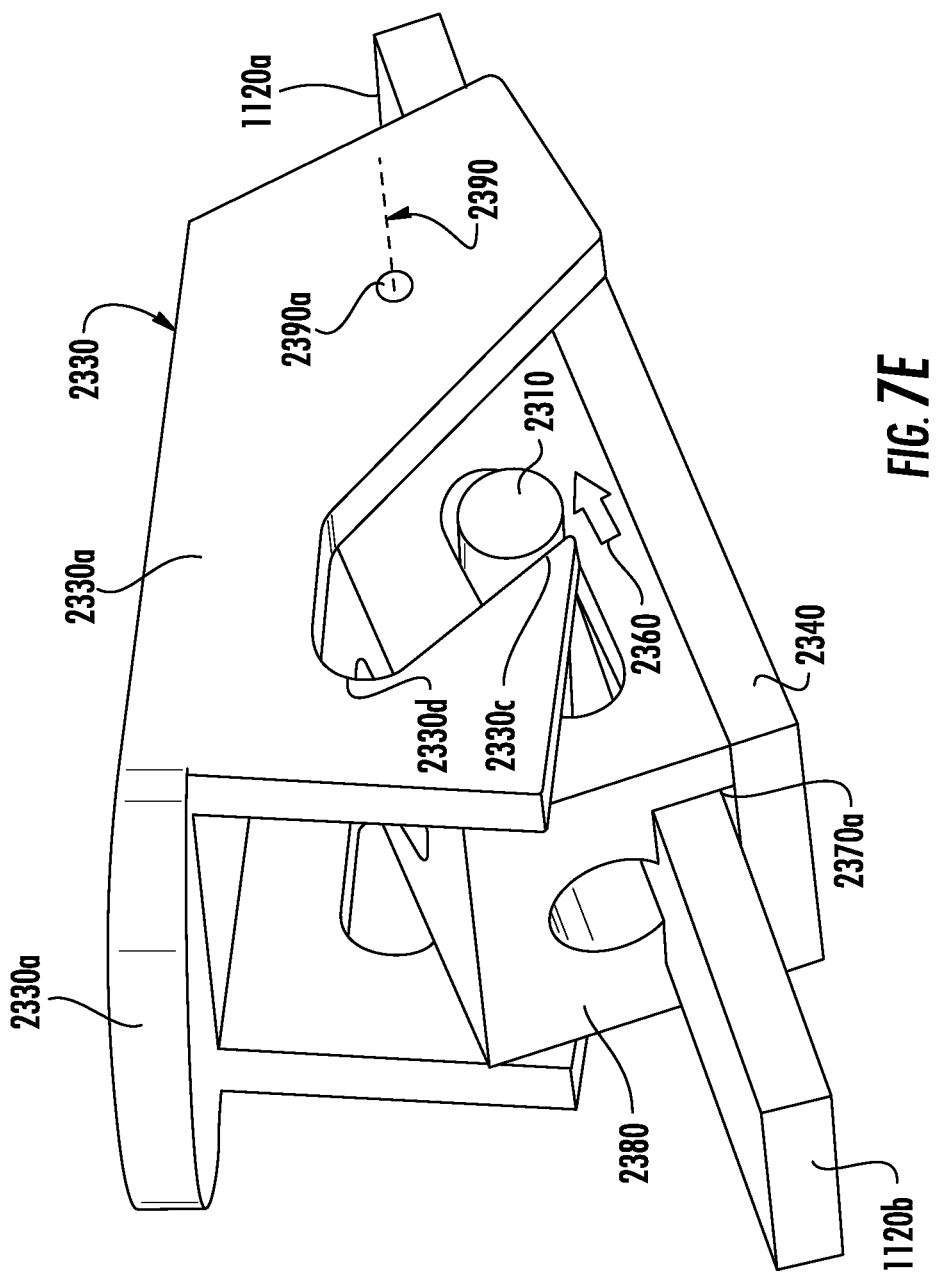

The friction lock 1110 has two modes: a locked mode, illustrated in FIGS. 7A-C, and an unlocked mode, illustrated in FIGS. 7D-E. In the locked mode, the latch 2330 is positioned such that the spring 2320 can extend the roller 2310 across the recess 2370 such that the roller 2310 is in contact with the latch at the locking interface 2330d. In such a position, the spring 2320 is applying a force 2350 on the roller 2310 such that the roller 2310 is pressed up against the locking interface 2330d. The locking interface 2330d is tapered such that the locking interface surface 2330d has approximately the same arc as the roller 2310 at the position where the roller 2310 engages the locking interface 2330d, and the locking interface 2330d has a wider arc in the positions not engaging the roller 2310, when the friction lock is in the locked position. The force 2350 applied by the spring 2320 increases the static friction between the roller 2310 and the locking interface 2330d. Therefore, when a force is applied to the sliding bar 1120, in the direction of a second end 1120b from a first end 1120a, the sliding bar 1120 engages the bottom of the roller 2310 and a clockwise force is applied to the roller 2310. However, the high static force 2301 of the roller 2310 and locking interface 2330d engagement creates a counter-force equal to clockwise force created by the sliding bar 1120. The roller 2310 therefore is pinched between the locking interface 2330d and the sliding bar 1120 such that neither the roller 2310 nor the sliding bar 1120 may roll or slide, respectively. Therefore, the friction lock 1110 is a restriction mechanism for a sliding bar 1120 traveling in a direction from a first end 1120a towards a second end 1120b.

Continuing with the locked mode of the friction lock 1110, if the sliding bar 1120 travels in a second direction, travelling from the second point 1120b toward the first point 1120a, the friction lock 1120 does not restrict the sliding movement. In such an embodiment, the sliding bar 1120 engages the bottom of the roller 2310 and creates a counter-clockwise force on the roller, along with a general force in the direction of the travelling path of the sliding bar. The force applied to the roller 2310 cause the roller 2310 to rotate in a direction away from the locking interface 2330d. As the surface of the latch 2330 is wider at the areas beyond the locking interface 2330d, the roller is not pinched into a surface of the latch 2330 and therefore only the static and sliding friction forces of the interface of the roller 2310 and the spring 2320 are resistive to the turning force of the roller 2310. In one embodiment, these friction forces are small enough, relative to the force applied by the sliding bar 1120, that the roller 2310 is able to roll. As the roller 2310 rolls in the counter-clockwise manner, the sliding bar 1120 may slide underneath the roller 2310 in the direction of the force applied to the sliding bar 1120. Therefore, even when the friction lock 1120 is in a "locked" position, the friction lock 1120 still allows a sliding bar 1120 to travel in one direction, while completely restricting movement of the sliding bar 1120 in the opposite direction.

The second mode of the friction lock 1120 is the unlocked mode, illustrated in FIGS. 7D-E. In this embodiment, the latch 2330 is in a second position defined by a rotation about the pivot axis 2390 such that the unlocking interface 2330c of the latch 2330 engages the roller 2310. As illustrated in FIGS. 7D-E, moving the latch 2330 into this second position causes the latch 2330 to roll the roller 2310 into the spring 2320, compressing the spring 2330 such that the roller 2310 is closer to the wall 2380(a) (illustrated in FIG. 7C) when the latch 2330 is in this second, unlocked, position than when the latch is in the first, locked, position.

As the latch is a flat, ramped surface, relative to the roller, the spring's 2320 force 2350 on the roller 2310 generally causes the roller 2310 to upward, away from the sliding bar 1120. In some embodiments, the roller 2310 is completely separated from the sliding bar 1120. In other embodiments, the roller 2310 still engages the sliding bar 1120, but no significant friction force is applied to the roller 2310 that could prevent the roller 2310 from rolling. As such, the sliding bar 1120 may slide beneath the sliding bar (either engaging and rolling the roller 2310, or not engaging the roller 2310) relatively freely without restriction of movement in either direction.

In one embodiment, as illustrated in FIGS. 8A through 8G, the force applicator mechanism 318 is embodied by a dial mechanism 800 having an upper dial member 800a, a lower dial member 800b, and a switch 800c where the upper dial member 800a rotates clockwise and/or counter-clockwise with respect to the lower dial member 800b, and the orientation of the switch 800c with respect to the upper dial member 800a allows for rotation of the upper dial member 800a in either two directions, or restricts the rotation of the upper dial member 800a to one (e.g. clockwise) direction.

The upper dial member 800a may comprise a plurality of plungers 802, rollers 804, springs 806, plates 808, or depressions 810. The bottom surface of the upper dial member 800a is defined by a spool 812 such that a force applicator 319 (e.g. a cable, a belt) may be wrapped around the spool 812, and may unravel and/or wind around the spool 812 to lengthen and/or shorten based on the orientation of the force applicator mechanism 318 (e.g. dial mechanism 800). The spool 812 may then be covered by the lower dial member 800b which may comprise an aperture 824 for allowing the force applicator 319 to exit the dial mechanism 800, a recess 822 in the top of the lower dial member 800b for receiving and being operatively coupled with the upper dial member 800a, and more specifically, the barrel 834 of the switch 800c. Furthermore, a recess 824 in the bottom of the lower dial member 800b may be internally threaded such that the dial mechanism 800 may be attached to another member (e.g., hinge plate) discussed previously herein. The switch 800c may comprise one or more pins 830, protrusions 832 located on the bottom surface switch 800c and a barrel 834 therein. The switch 800c may be operatively coupled with the upper dial member 800a. Specifically, the barrel 834 may be operatively coupled with the switch 800c via a fastener or rivet (e.g. a shoulder screw), or other like fastening means. The barrel 834 may then be securely positioned within an opening 816 in the center of the upper dial member 800a such that at least a portion 834a of the barrel 834 extends beyond the bottom surface of the upper dial member 800a, the extended portion 834a may be further shaped such that it securely fits within the recess 822 of the lower dial member. For example, as shown in the illustrated embodiments of FIG. 8, the extended portion 834a is square shaped such that is securely fits within the square shaped recess 822. In this way, the lower dial member 800b may be statically positioned such that, as the barrel 834 rotates, the upper dial member 800a dynamically moves with respect to the lower dial member 800b.

Figure 8A:
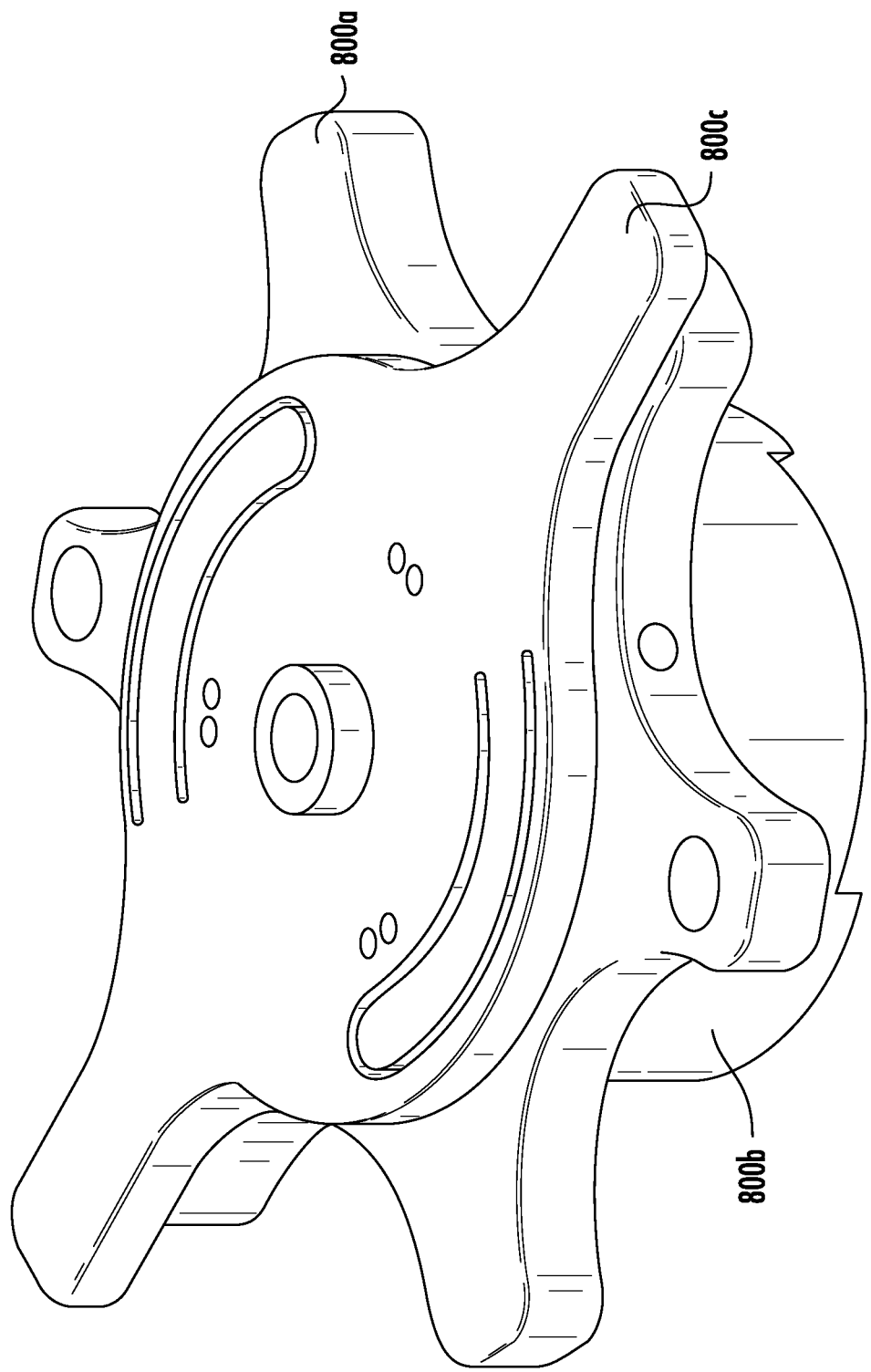
Figure 8B:
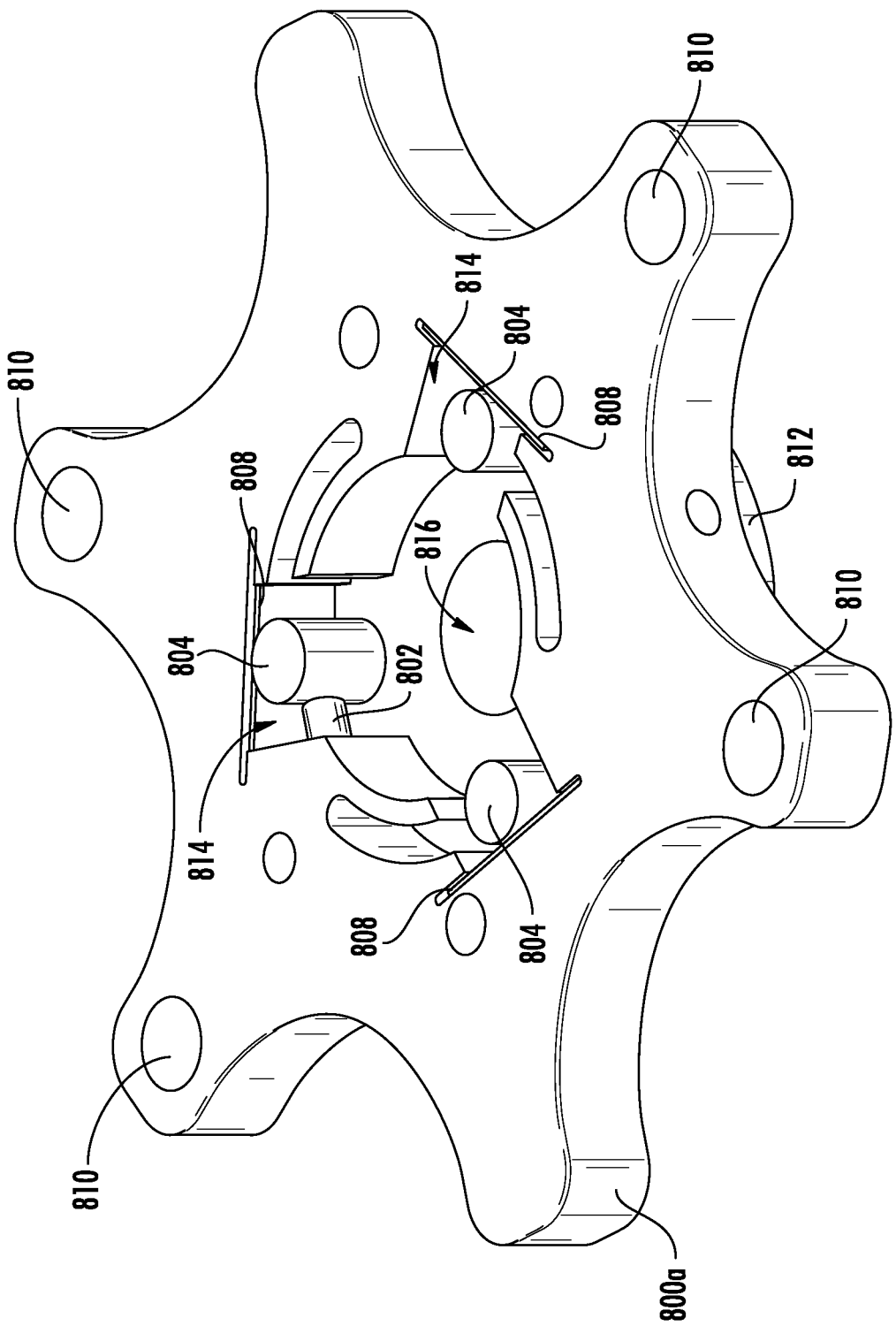
Figure 8C:
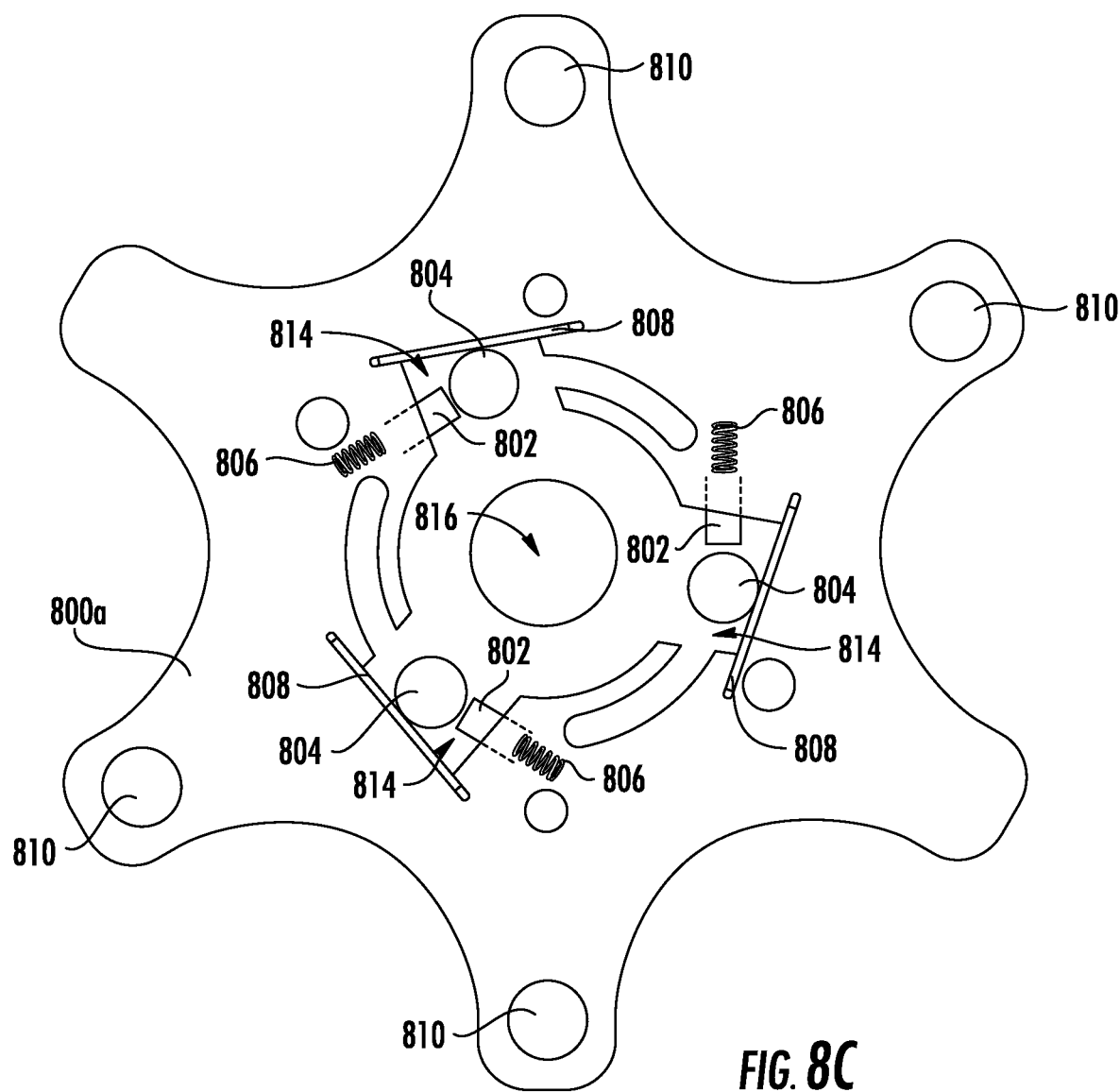
Figure 8D:
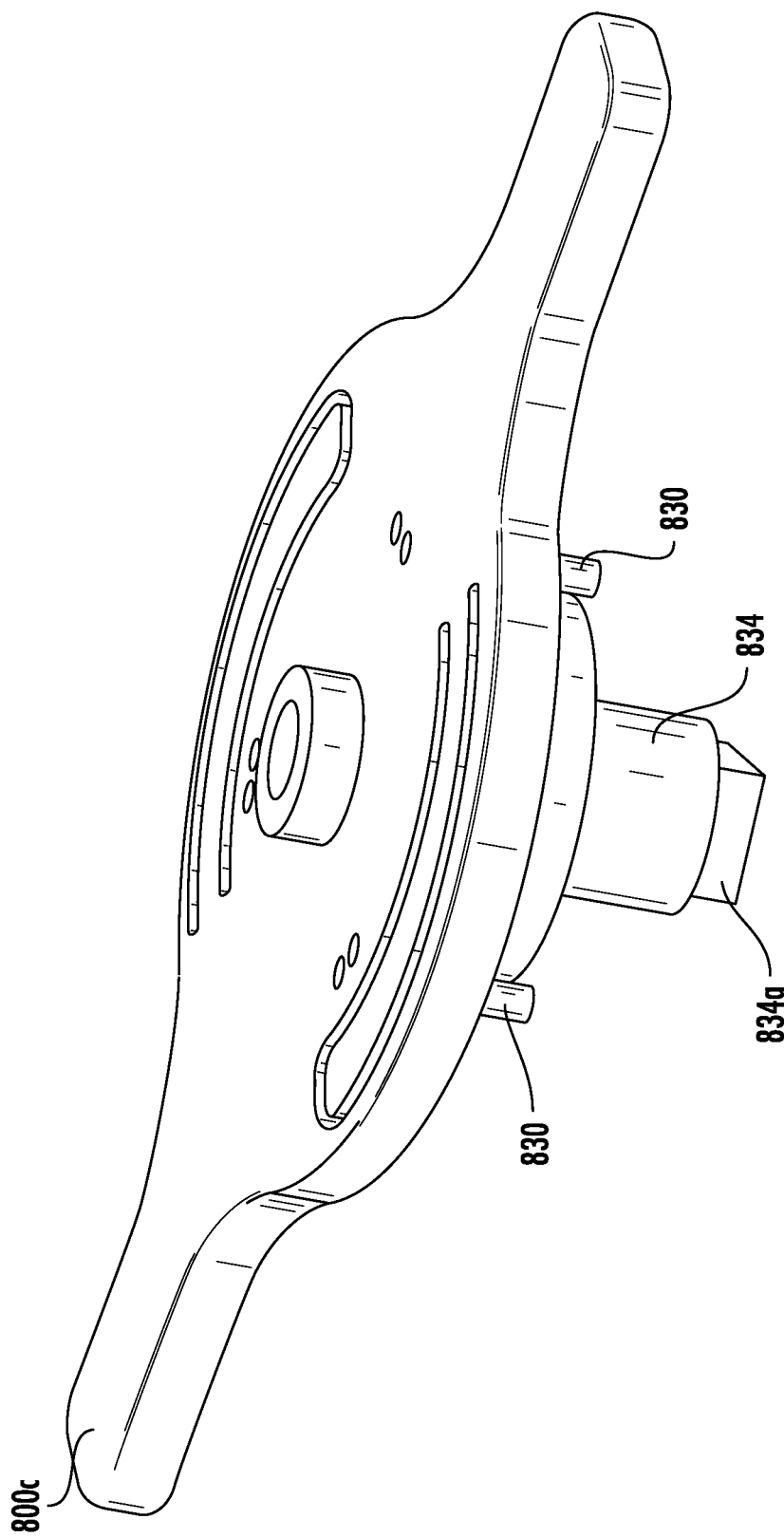
Figure 8E:
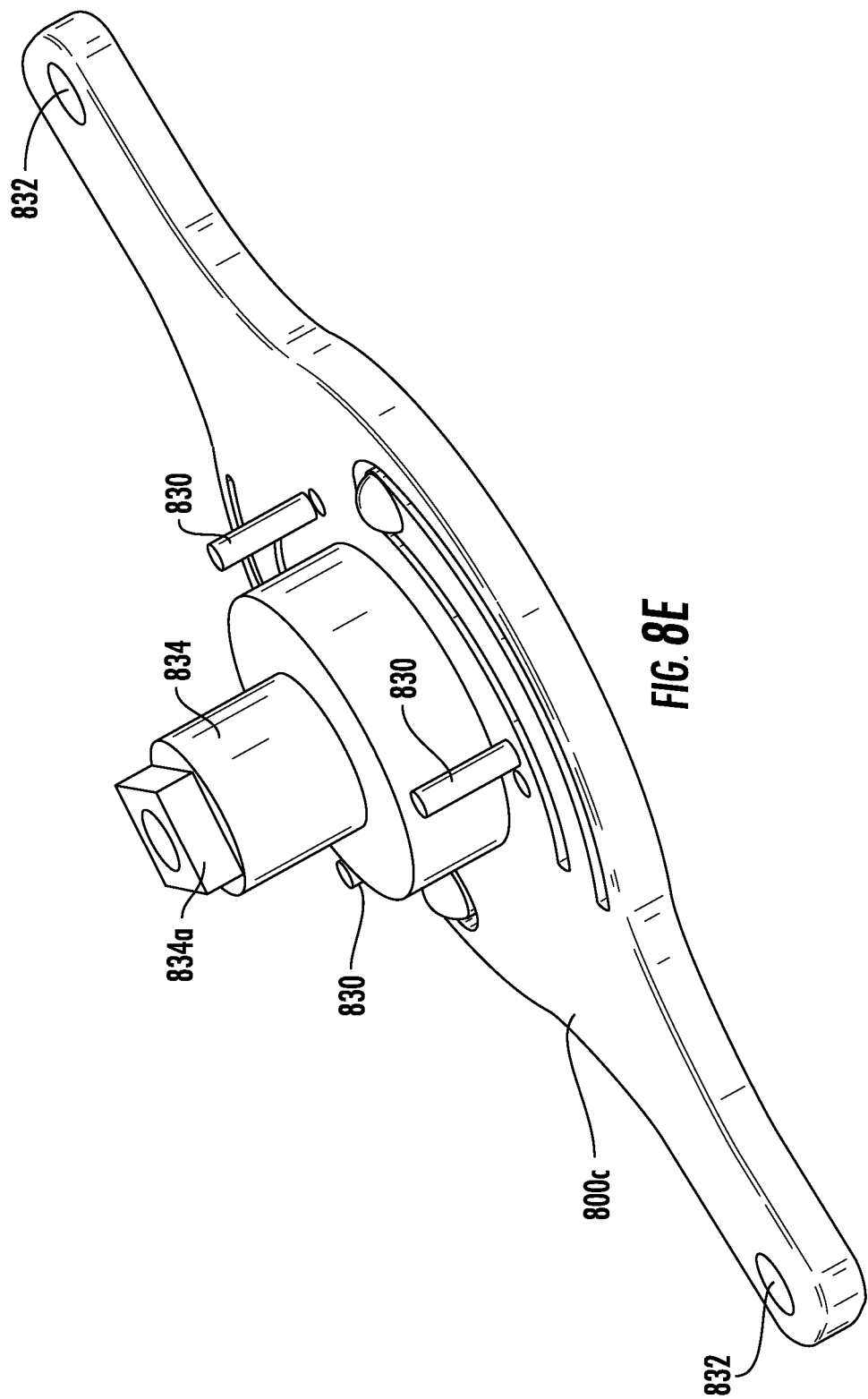
Figure 8F:
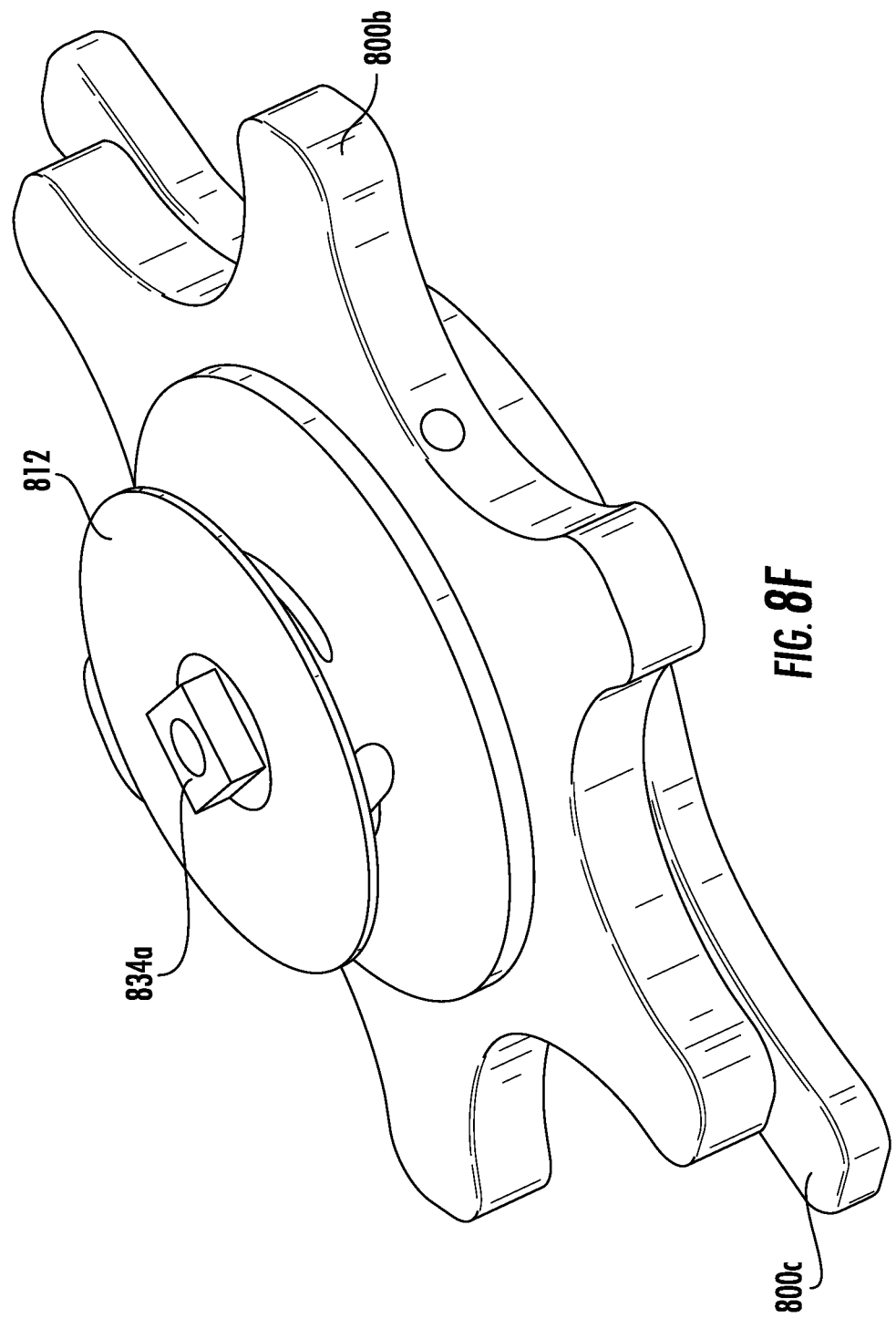
Figure 8G:
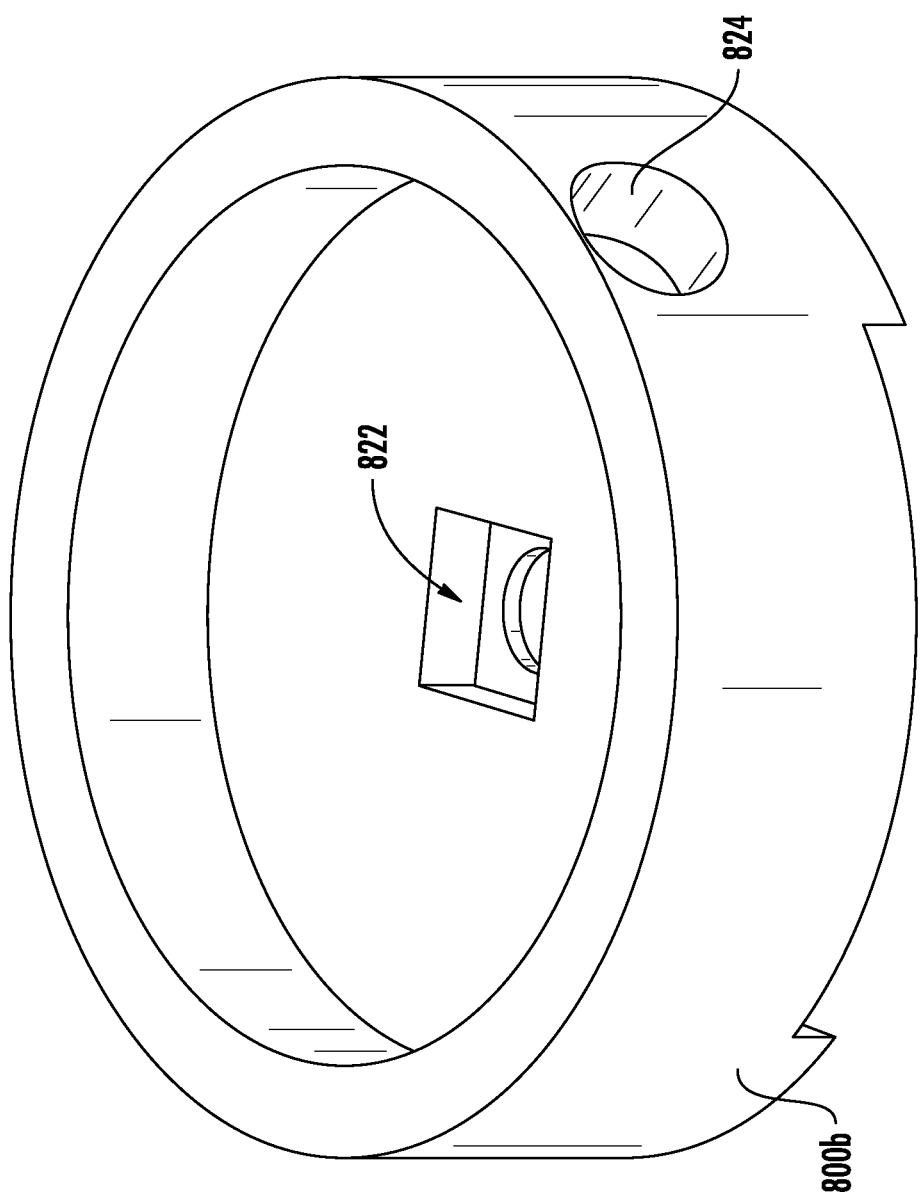
Figure 9C:
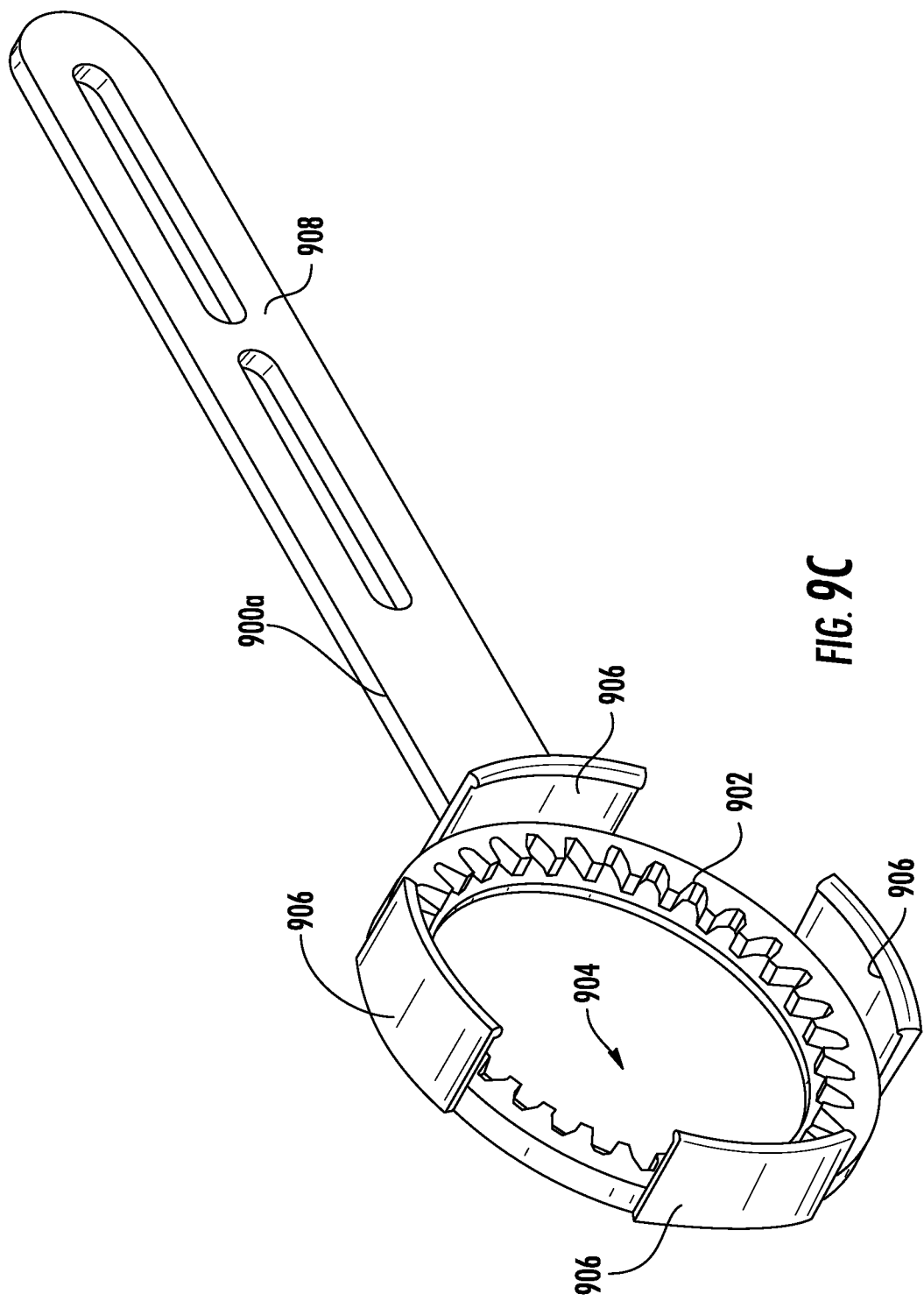
Figure 9D:
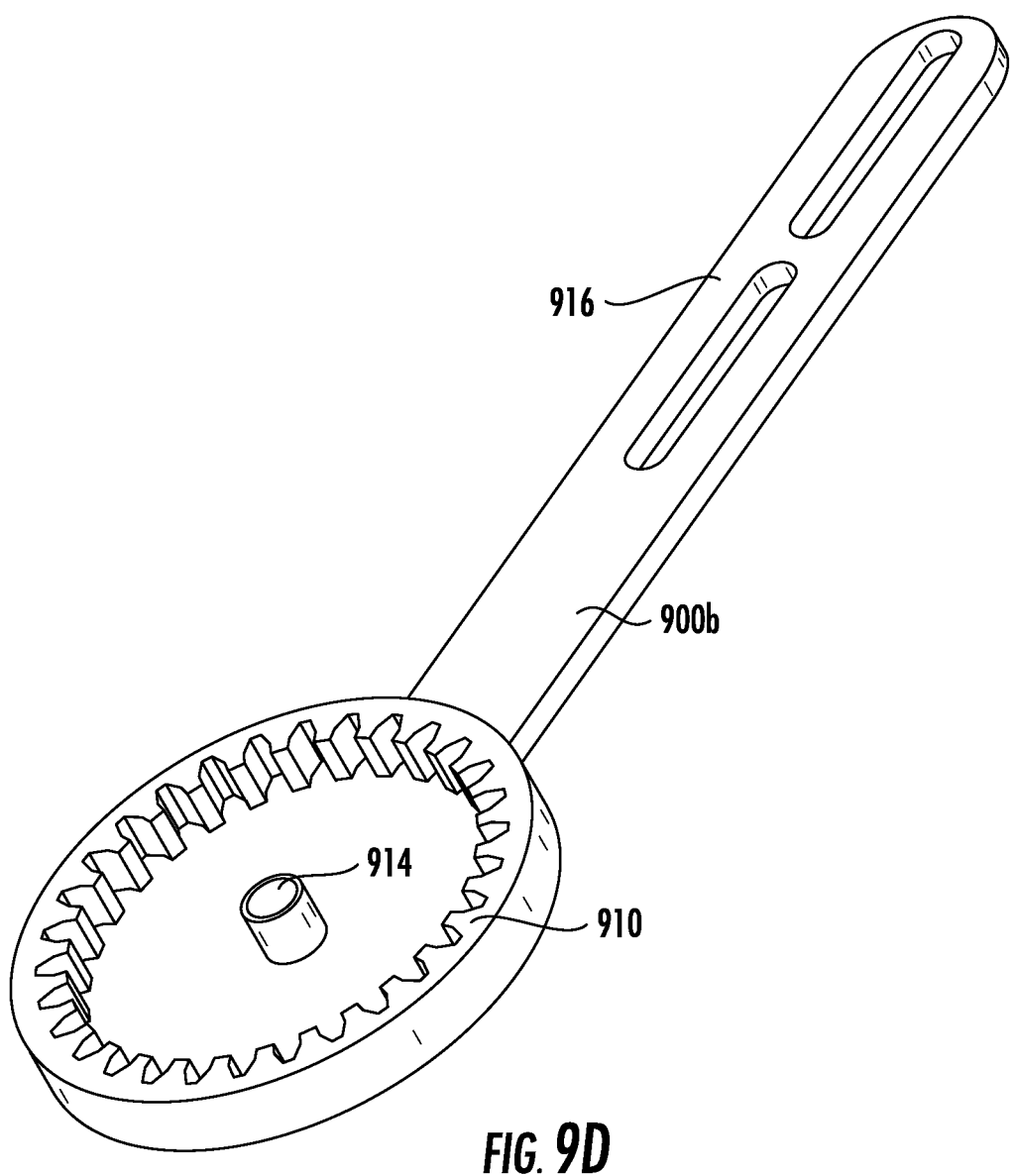
Figure 9E:
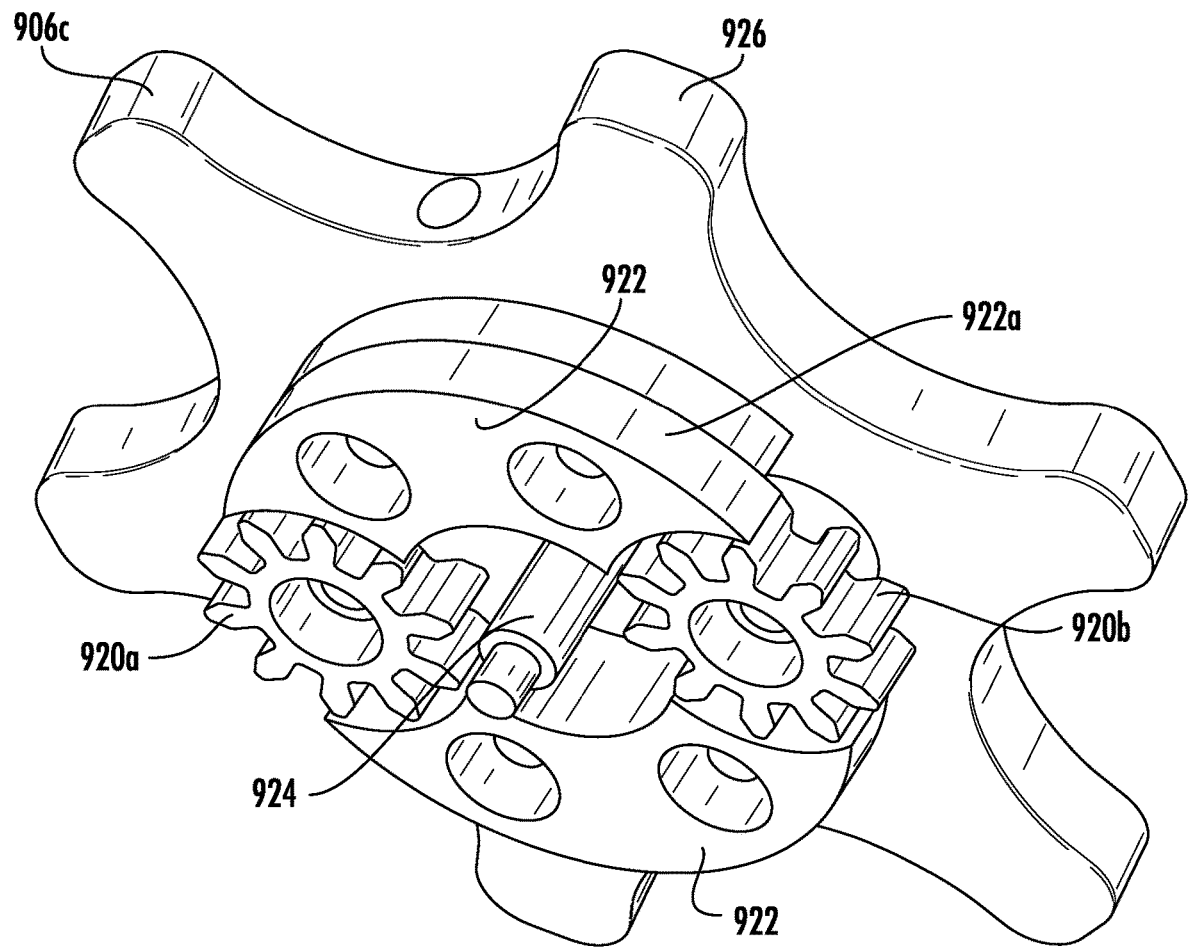
Figure 9F:
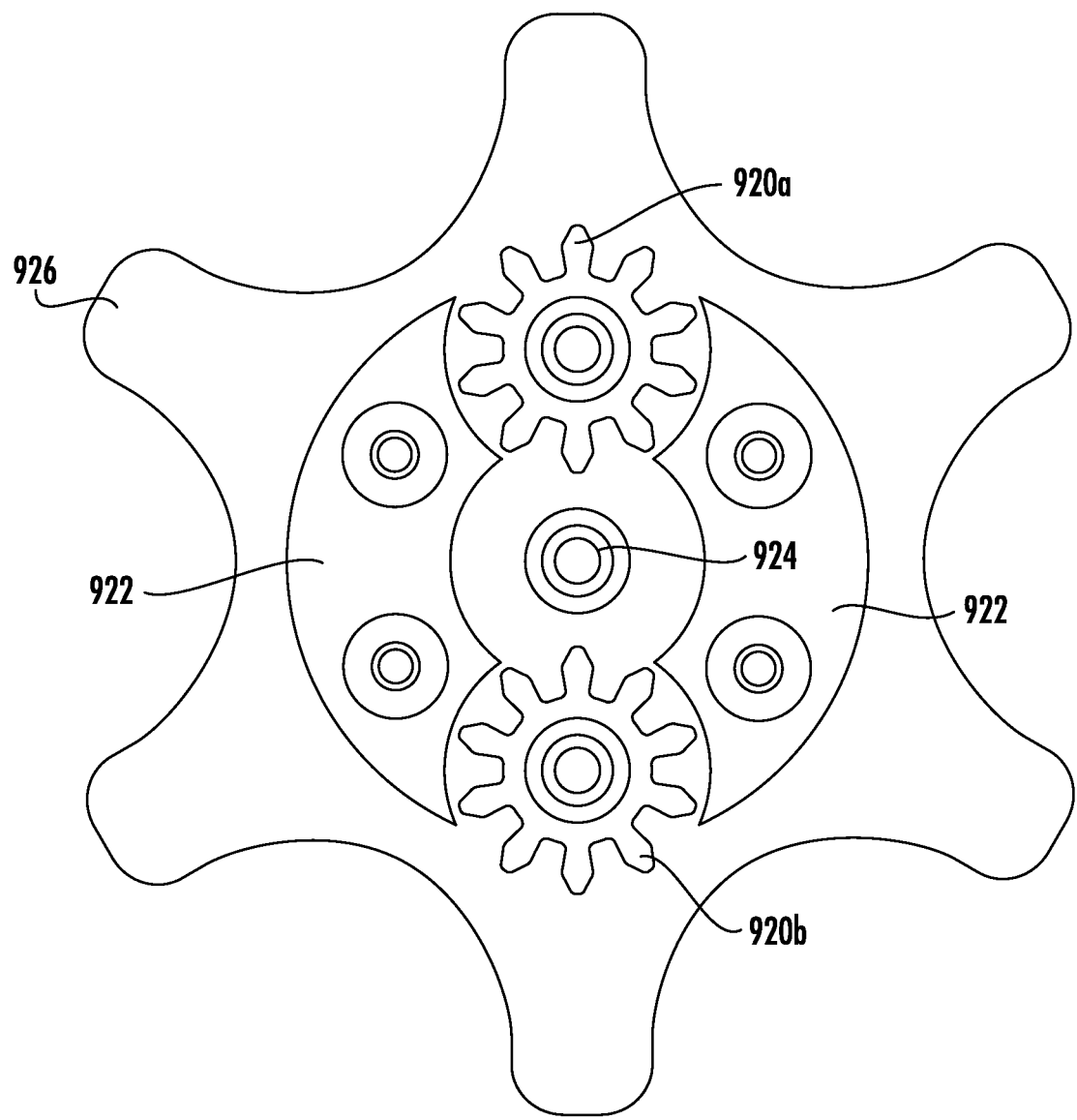
Figure 10B:
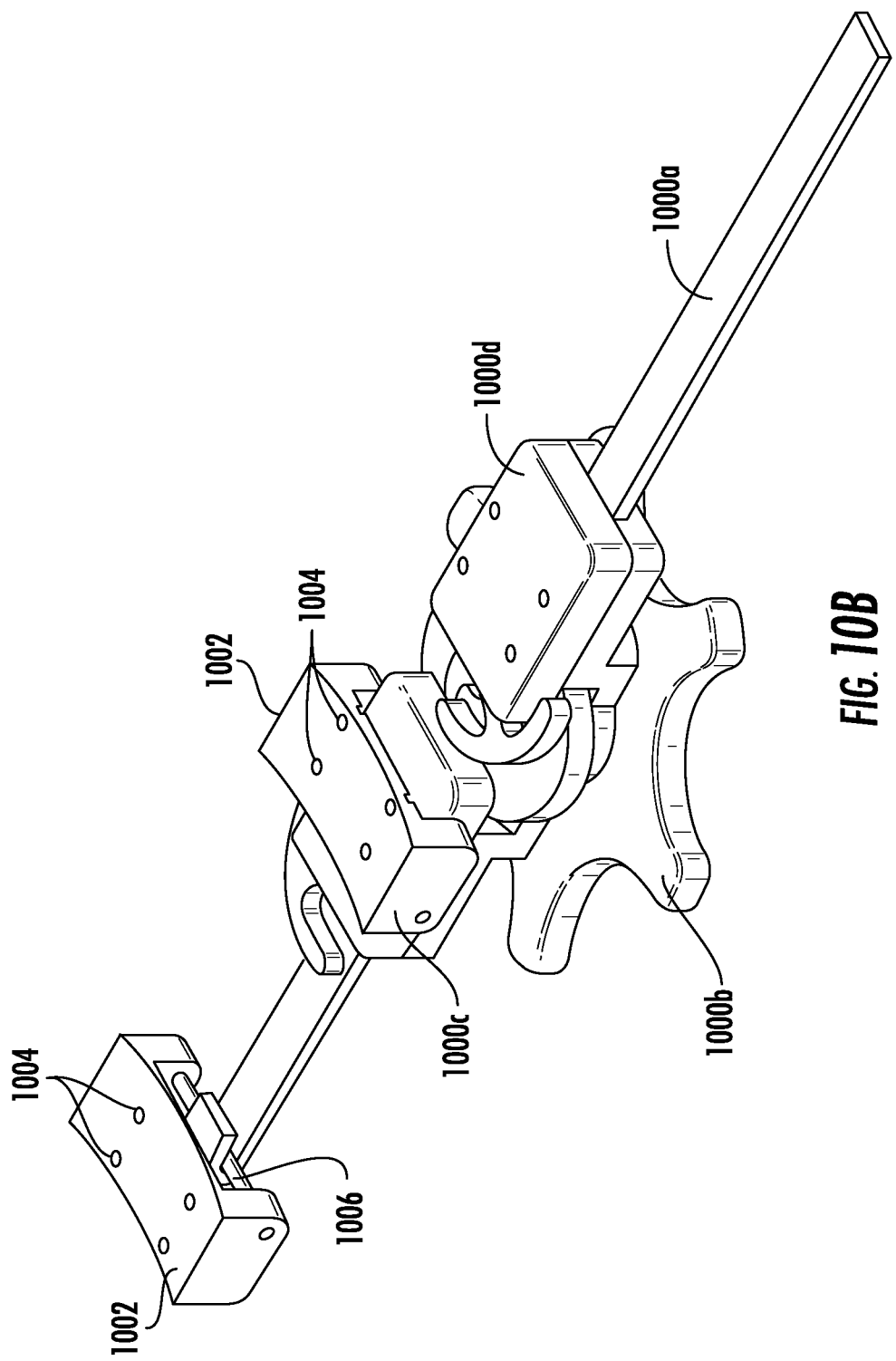
Figure 10C:
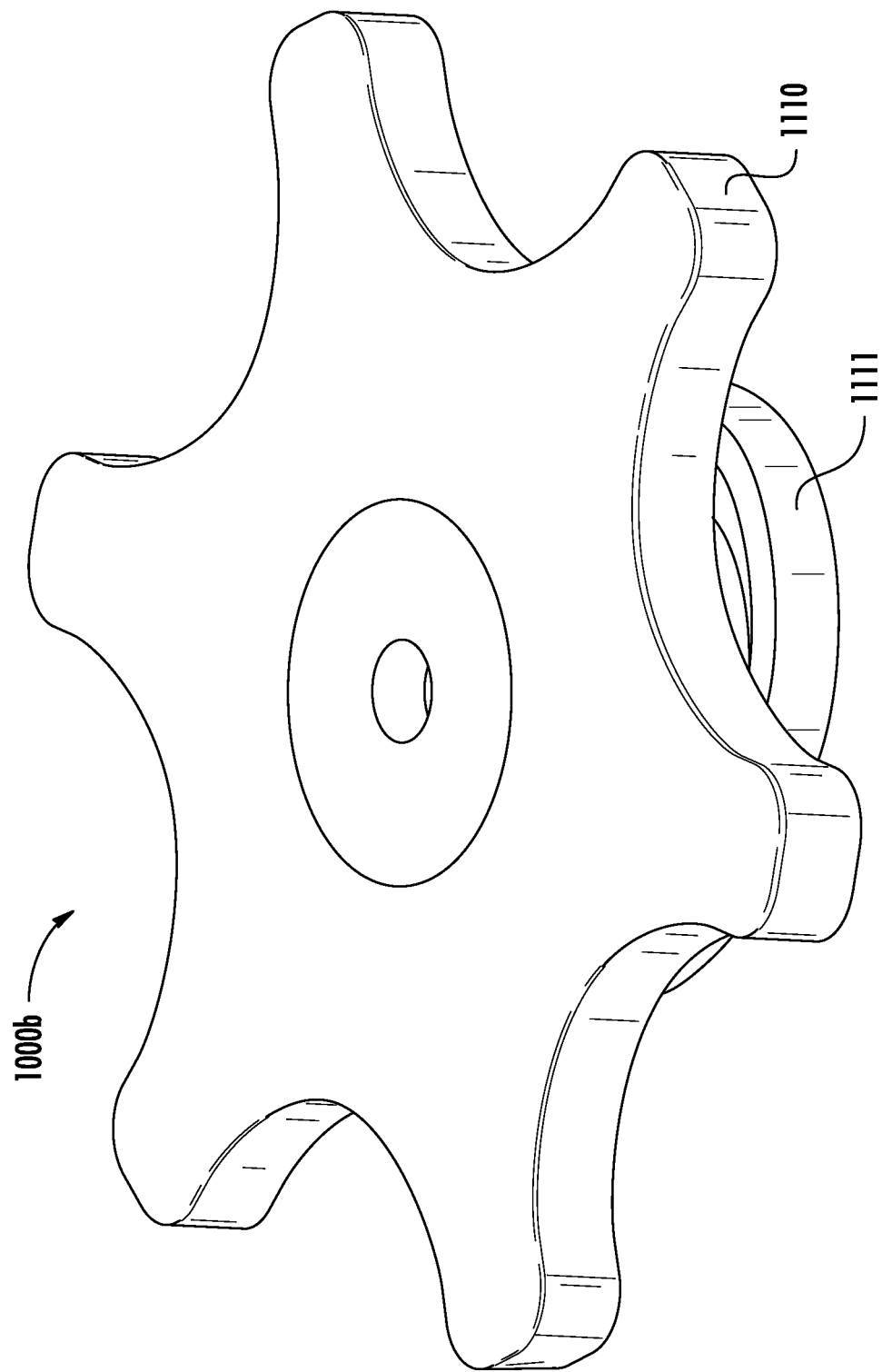
Figure 10D:
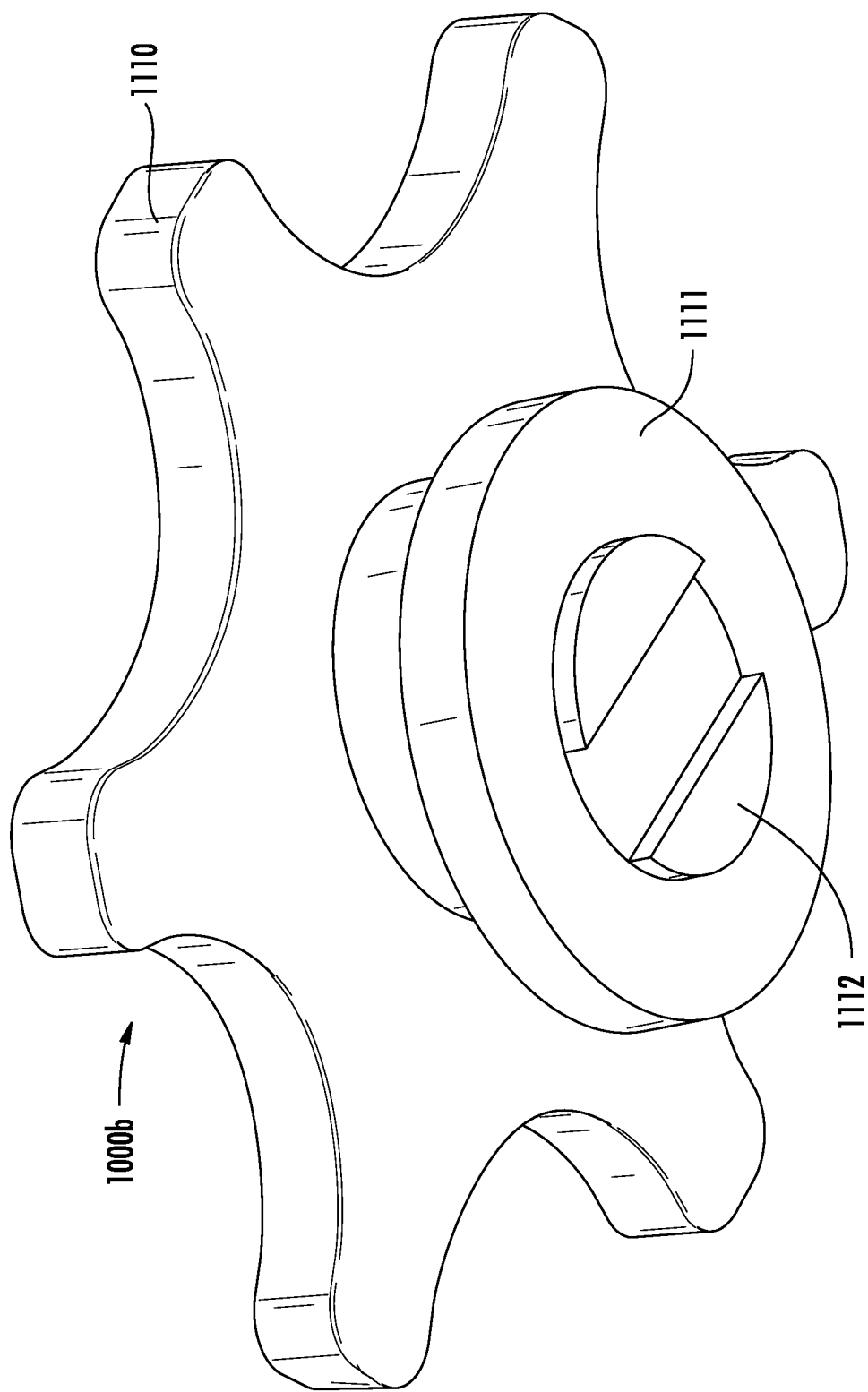
Figure 10E:
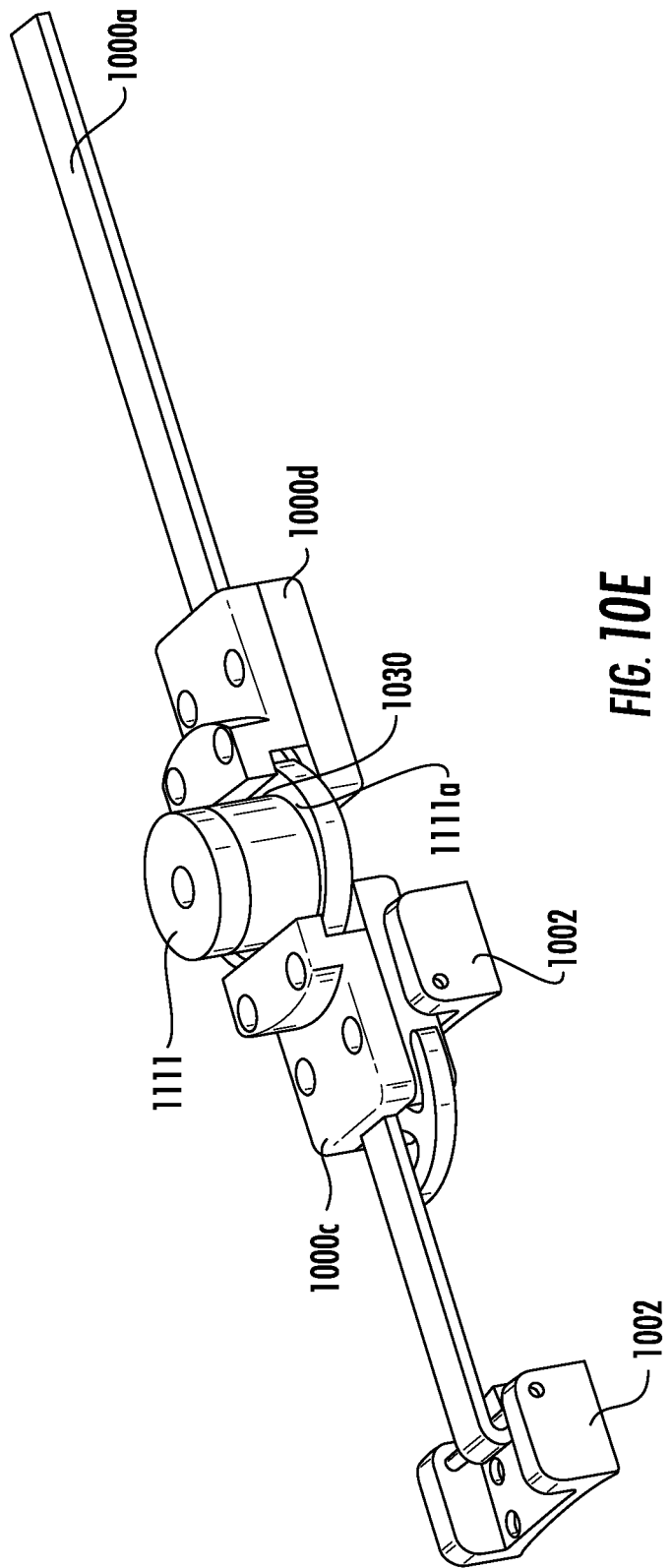
Figure 10G:
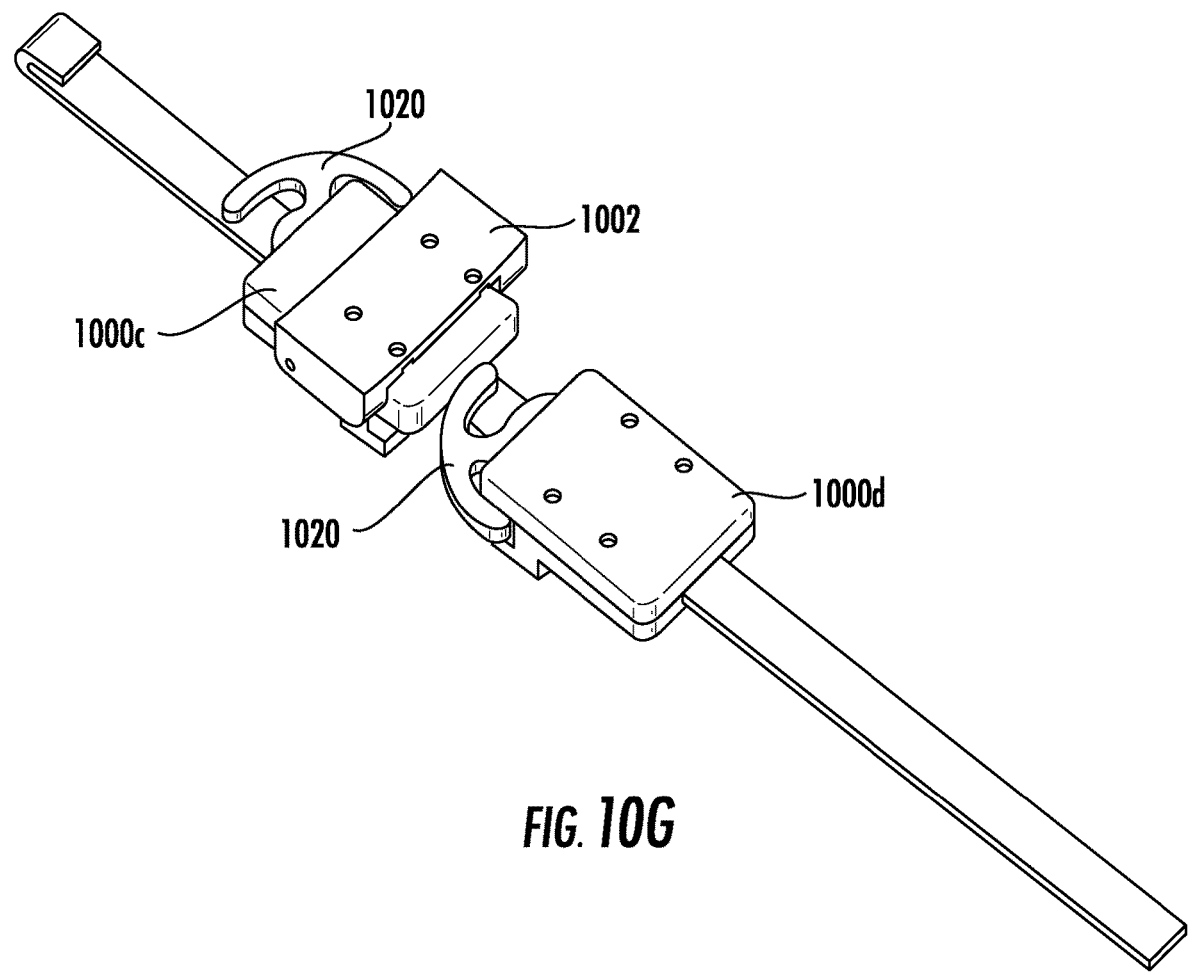
Figure 10H:
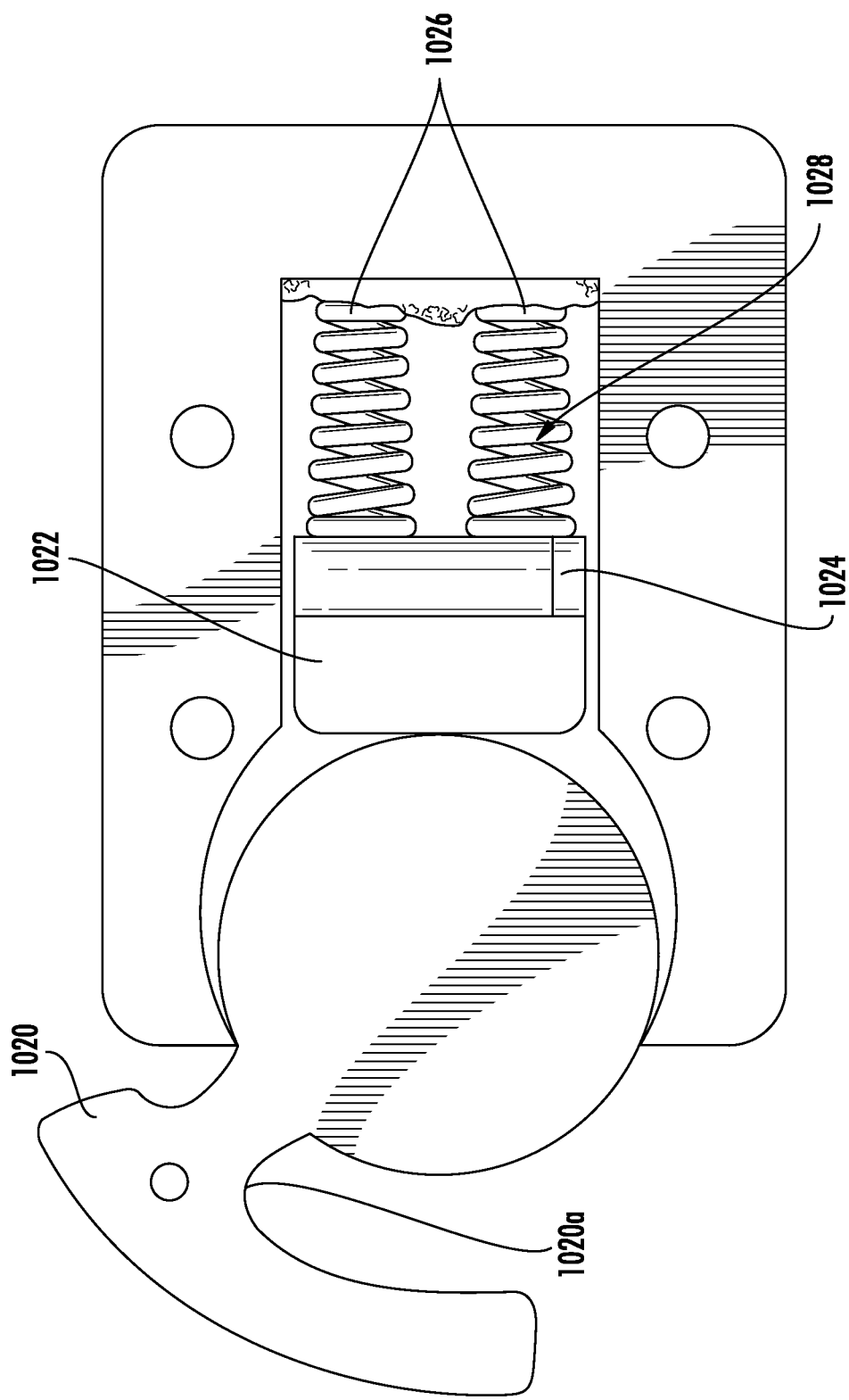

The rotational direction of the spool may be directed by the internal barrel 834 within the center of the dial mechanism, where the spool 812 may be configured to rotate in only one direction, or rotate in both directions, based on the configuration of the dial mechanism 800 with respect to the switch 800c. As illustrated in FIGS. 8B and 8C, when assembled one or more plungers 802, rollers 804, and springs 806 are positioned, within a plurality of recesses 814, in a circular orientation that corresponds to the one or more pins 830 within the switch 800c. The plunger 802 and the roller 804 may be defined by cylindrical components, and in one embodiment, the roller 804 may be positioned within the dial mechanism 800 in an upright orientation such that a top surface 804a of the roller 804 is flush with a top surface of the dial mechanism 800. In one embodiment, as shown in FIG. 8, the plunger 802 may be positioned within the dial mechanism 800 such that a top surface 802a of the plunger is adjacent to the side surface of the roller 804, and a bottom surface 802b of the plunger is operatively coupled with a spring 806 that is compressed within the interior of the dial mechanism 800. In such an embodiment, when the roller 804 is removed, the plunger 802 may be positioned within the dial mechanism 800 such that the plunger 804 fills the recess 814 and a tops surface 804a of the plunger 804 is adjacent to an interior side of the recess, and a bottom surface 802b of the plunger is operatively coupled with a spring 806 that is expanded within the recess 814 of the dial mechanism 800.

In one embodiment, the switch 800c may be mounted on the top of the upper dial member 800a, and positioned such that the side surface of the pins 830 are aligned with the side surface of the rollers 804, and in response to turning the switch 800c in a counter-clockwise direction the protrusions 832 are positioned within a first set of depressions 810a, and the pins 830 move in a lineal fashion towards the plungers 802. The coupling of the protrusions 832 within the depressions 810 may restrict free flowing movement and cause the switch 800c and the dial mechanism to be securely positioned with respect to one another. In another embodiment, the depressions may visually indicate the correct positioning for the switch. For example, the switch may be positioned in an "on" position in which the rollers 804 are engaged by the pins 830, or the switch may be positioned in an "off" position in which the rollers 804 are disengaged by the pins 830. In such an embodiment, in response to the counter-clockwise rotation of the switch 800c, the pins 830 may be configured to engage the rollers 804 such that the rollers 804 are caused to further compress the plungers 802 and springs 806 into the interior surface of the dial mechanism 800 allowing the roller 804 to be repositioned such that the dial can rotate in two directions. Specifically, the recess 814 may be defined by a channel having a width of "X" on a first end proximate to the plunger 802, and a narrower width of "Y" on a second end distal from the plunger 802 such that when the roller 804 is engaged by the pins 830 the roller 804 is repositioned proximate to the first end of the channel and the friction between the roller 804 and the barrel 834 is reduced or eliminated allowing the barrel 834 to freely rotate in a counter-clockwise and a clockwise direction resulting in the multidirectional rotation of the spool 812. As the barrel 834 rotates in the counter-clockwise direction the force applicator 319 may unwind from the spool 812 and further lengthen with respect to the dial mechanism. Alternatively, as the barrel 834 rotates in the clockwise direction the force applicator 319 may wind around the spool 812 and shorten with respect to the dial mechanism. It should be noted that, in such an embodiment, when the force applicator 319 is completely wound around the spool 812 the barrel 834 is restricted from further rotating in the clockwise direction.

In one embodiment, the switch 800c may be mounted on the top of the upper dial member 800a, and positioned such that the side surface of the pins 830 are aligned with the side surface of the rollers 804, and in response to turning the switch 800c in a clockwise direction the protrusions 832 are positioned within a second set of depressions 810b, and the pins 830 move in a lineal fashion away from the plungers 802. In such an embodiment, in response to the clockwise rotation of the switch 800c, the pins 830 may be configured to disengage the rollers 804 such that the rollers 804 and plungers 802 are expanded within the recess 814 of the dial mechanism 800 allowing the roller 804 to be repositioned such that the dial is restricted to rotate in one direction (e.g. clockwise). Specifically, the recess 814 may be defined by a channel having a width of "X" on a first end proximate to the plunger 802, and a narrower width of "Y" on a second end distal from the plunger 802 such that when the roller 804 is disengaged by the pins 830 the roller 804 is repositioned proximate to the second end of the channel and the friction between the roller 804 and the barrel 834 is increased restricting the barrel 834 from freely rotating in the counter-clockwise direction resulting in the one directional rotation of the spool 812 in the clockwise direction. The barrel 834 may be restricted from rotating in the counter-clockwise direction such that the force applicator 319 is restricted from unwinding from the spool 812 and further lengthening with respect to the dial mechanism. Alternatively, as the barrel 834 rotates in the clockwise direction the force applicator 319 may wind around the spool 812 and shorten with respect to the dial mechanism. It should be noted that, in such an embodiment, when the force applicator 319 is completely wound around the spool 812 the barrel 834 is restricted from further rotating in either the clockwise or counter-clockwise direction.

In one embodiment, as illustrated in FIGS. 9A through 9F, the force applicator mechanism 318 is embodied by a harmonic dial mechanism 900 having an upper dial member 900a, a lower dial member 900b, and a gear dial 900c where the upper dial member 900a and the lower dial member 900b pivot with respect to an axis, and the gear dial 900c is configured to control the rotational movement of the upper and lower dial members 900a, 900b when the gear dial 900c is actively engaging both the upper and lower dial members 900a, 900b. It should be noted that in such an embodiment at least a portion, and more specifically extended arms, of the upper dial member 900a and the lower dial member 900b may be defined by the upper and lower hinge plates 113, 114. In an exemplary embodiment, the harmonic dial mechanism 900 may be located at the elbow joint of the wearer, the lower hinge plate 114 may be defined by the extended arm of the upper dial member 900a, and the upper hinge plate 113 may be defined by the extended arm of the lower dial member 900b. The force applicator mechanism 318 may additional provide a pneumatic force in some embodiments.

The upper dial member 900a may comprise an upper set of teeth 902, an opening 904 for receiving and being operatively coupled with the gear dial 900c, a plurality of fasteners 906 configured for fastening the upper dial member 900a to the lower dial member 900c, and an extended arm 908. The lower dial member 900b may comprise a lower set of teeth 910, a bottom surface 912, a recess 914 configured for coupling with the gear dial 900c, and an extended arm 916. The gear dial 900c may comprise one or more planetary gears 920, at least one stopping mechanism 922, a rivet 924 configured for coupling with the lower dial member 900b, and a dial head 926, where the components of the gear dial 900c may be operatively coupled with the gear dial 900c via a plurality of apertures within the dial head 926 one or more attachments means including, but not limited to, nuts, bolts, screws, adhesive, other rivets, and the like. As such at least a portion of the recess 914 may be internally threaded, and at least a portion of the rivet 924 may be externally threaded such that the two components are configured to securely attach to one another. Additionally the harmonic dial mechanism 900 may be spring loaded such that a spring (not shown) is positioned around the rivet 924, where the spring is configured to aid in positioning the gear dial 900c with respect to the upper dial member 900a and the lower dial member 900b. Furthermore, the stopping mechanism 922 may comprise a ledge 922a that extends beyond the diameter of the opening 904 in the upper dial member 900a such that when the top surface of the ledge 922a reaches the opening 904, the ledge 922a stops the motion of the gear dial 900c, and the gear dial 900c is restricted from being positioned beyond the opening 904 of the upper dial member 900a. In this way the gear dial 900c is configured to be contained within a housing defined by the upper and lower dial members 900a, 900b.

In one embodiment, the gear dial 900c is positioned in a first position such that the planetary gears 920 engage both the upper and lower set of teeth 902, 910. In such an embodiment the top surface of the planetary gears 920 may be positioned proximate to the opening 904 of the upper dial member 900a such that there is a recess between the upper dial member 900a and the dial head 926. In one embodiment, the first set of teeth 902 may comprise more teeth than the second set of teeth 910, or vice versa, such that the gear ratio between the planetary gears 920 and the first set of teeth 902 is different than that gear ratio between the planetary gears 920 and the second set of teeth 910. In this way, when the dial head 926 is turned the extended arms of the upper and lower dial member 908, 916 move, rotate, and/or pivot with respect to one another. In an alternate embodiment, the first planetary gear 920a may comprise more teeth than the second planetary gear 920b, or vice versa, such that the gear ratio between the first planetary gears 920s and the first and second set of teeth 902, 910 is different than that gear ratio between the second planetary gears 920b and the first and second set of teeth 902, 910. In this way, when the dial head 926 is turned the extended arms of the upper and lower dial member 908, 916 may incrementally move, rotate, and/or pivot with respect to one another such that the gear dial 900c maintains the position of the first and second set of teeth 902, 910 and does not allow for free movement of the extended arms 908, 916 or back drive of the current position. The gear dial 900c may be rotated either clockwise or counter-clockwise such that the harmonic dial mechanism 900 may promote either the extension of flexion of the elbow joint of the wearer.

In another embodiment, the gear dial 900c is positioned in a second position such that the planetary gears 920 is disengaged from the upper set of teeth 902, and engages the lower set of teeth 910. In this way the gear dial 900c may be configured to freely rotate either clockwise or counter-clockwise based on the natural motion of the wearer, where the current position may be locked into place my moving the gear dial 900c back into the first position. In such an embodiment the bottom surface of the planetary gears 920 may be positioned proximate to the bottom surface 912 of the lower dial member 900b such that the top surface of the planetary gears 920 is flush with the top surface of the second set of teeth 910, and the bottom surface of the dial head 926 is adjacent to the top surface of the upper dial member such that there is not a recess between the upper dial member 900a and the dial head 926. In this way, when the dial head 926 is turned the extended arms of the upper and lower dial member 908, 916 move, rotate, and/or pivot with respect to one another. In such an embodiment, the extended arms of the upper and lower dial member 908, 916 may continuously move, rotate, and/or pivot with respect to one another.

In one embodiment, as illustrated in FIGS. 10A through 10H, the force applicator mechanism 318 is embodied by a dual friction lock mechanism 1000 having a friction lock bar 1000a, a rotary dial 1000b, and a first and a second friction lock member 1000c, 1000d, respectively, where the first and second friction lock members 1000c, 1000d are configured to either incrementally move linearly along the friction lock bar 1000a in an "inchworm" like motion with respect to one another, or continuously move linearly along the friction lock bar 1000a. The dual friction lock mechanism 1000 may further comprise and/or be coupled with one or more hinge plates via an attachment member 1002. The attachment members 1002 may be defined by a component having a plurality of apertures 1004 for receiving rivets and a rod 1006 configured to operatively couple with at least a portion of the friction lock bar 1000a. Furthermore, the bottom surface of the attachment members 1002 may be shaped such that they correspond to the attaching member. For example, the attachment members 1002 may be curved (as illustrated) if being attached to a curved bar or hinge plate, or the attachment members 1002 may be straight if being attached to a straight bar or hinge plate.

The rotary dial 1000b may comprise a dial head 1110, a camshaft 1111, and a base and/or bottom surface 1112 configured to be coupled with the friction lock bar 1000a. In this way, at least a portion of the bottom surface 1112 of the rotary dial 1000b may be sized and shaped such that it can be securely attached to the friction lock bar 1000a. When the friction lock bar 1000a is positioned within the bottom surface 1112 of the rotary dial 1000b, the friction lock bar 1000a is flush with the bottom surface 1112 of the rotary dial 1000b. The camshaft 1111 of the rotary dial 1000b may be substantially oval shaped and may comprise a recess 1111a configured for receiving and/or be operatively coupled with at least a portion of the first and second friction lock members 1000c, 1000d.

The first and second friction lock members 1000c, 1000d may each comprise a switch 1020, a plate 1022, a roller 1024, and springs 1026, where the orientation of the switch 1020 repositions the roller 1024 such that the movement of the roller 1024 is either restricted to one direction, or enabled for movement in two directions (e.g. forwards and backward). An optional piece of material (e.g. foam) may be placed between the springs 1026. It should be noted, that although the illustrated embodiments depict a plastic plate 1022, the plate 1022 may be formed of any suitable material not explicitly contemplated or illustrated herein (e.g. metal). Furthermore, in some embodiments, the plate 1022 may be optionally removed and the switch 1020 may directly engage the roller 1024.

The switch 1020 may be configured to lock the position of the first and second friction lock members 1000c, 1000d with respect to the friction lock bar 1000a such that the first and second friction lock members 1000c, 1000d are configured to only incrementally move linearly in one direction and do not back drive and/or move in the opposite direction. In such an embodiment, the switch 1020 may be centrally positioned such that the neck 1020a of the switch is perpendicular to the roller 1024, and the switch 1020 either directly or indirectly (e.g. via the plate 1022, engages the roller 1024 such that the roller 1024 is positioned proximate to a narrow and/or tapered end 1028a of a recess 1028, in which the roller 1024 and springs 1026 are positioned, within the first and second friction lock members 1000c, 1000d. In this way, the movement of the roller 1024 is restricted by the friction between the roller 1024 and the tapered end 1028a.

Alternatively, the switch 1020 may be configured to release and/or allow for a release of the position of the first and second friction lock members 1000c, 1000d with respect to the friction lock bar 1000a such that the first and second friction lock members 1000c, 1000d are configured to continuously move linearly in two directions (e.g. forwards/backwards, up/down) with respect to the friction lock bar 1000a. In such an embodiment, the switch may be offset proximate to an edge of the first and second friction lock members 1000c, and positioned such that the neck 1020a of the switch is acutely angled with respect to the roller 1024, and the roller 1024 is positioned proximate to a wider end 1028b of a recess 1028, in which the roller 1024 and springs 1026 are positioned, within the first and second friction lock members 1000c, 1000d. In this way, the roller 1024 is disengaged from the tapered end 1028a, and the movement of the roller 1024 is not restricted by the friction between the roller 1024 and the narrower tapered end 1028a.

A ledge 1030 of the first and second friction lock members 1000c, 1000d may be configured for being operatively coupled with the a recess 1111a in the camshaft 1111 of the rotary dial 1000b. As such the ledge 1030 may extend into the recess 1111a such that the first and second friction lock members 1000c, 1000d are coupled with one another via the camshaft 1111, and the first and second friction lock members 1000c, 1000d may move in relation to one another based on the orientation of the camshaft.

In one embodiment, the switch 1020 may be centrally positioned such that the neck 1020a of the switch is perpendicular to the roller 1024, the roller 1024 is positioned with the tapered end 1028a of the recess 1028 to restrict the movement of the first and second friction lock members 1000c, 1000d to one linear direction along the friction lock bar 1000a. Specifically, in response to turning the friction lock dial 1000b in either a clockwise or counter-clockwise motion, the camshaft 1111 moves the first and second friction lock members 1000c, 1000d apart from one another as its longer axis aligns with the first and second friction lock members 1000c, 1000d. In such an embodiment, only the first friction lock member 1000c is incrementally advanced forward along the friction lock bar, and the second friction lock member 1000d remains in a static position as the first friction lock member 1000c moves forward. As the friction lock dial 1000b is further rotated, the camshaft moves the first and second friction lock members 1000c, 1000d back towards one another as its shorter axis aligns with the first and second friction lock members 1000c, 1000d. In such an embodiment, only the second friction lock member 1000d is incrementally advanced forward along the friction lock bar, and the first friction lock member 1000c remains in a static position as the second friction lock member 1000d moves forward. In this way, the first and second friction lock members 1000c, 1000d alternate motion as they "inch" or incrementally advance along the friction lock bar 1000b similar to the motion of an inchworm.

In another embodiment, the switch may be offset proximate to an edge of the first and second friction lock members 1000c such that the neck 1020a of the switch is acutely angled with respect to the roller 1024, and the roller 1024 is positioned proximate to a wider end 1028b of a recess 1028 to enable the continuous movement of the first and second friction lock members 1000c in two linear directions along the friction lock bar 1000a. Specifically, in response to sliding the first and second friction lock members 1000c, 1000d forwards and/or backwards with respect to the friction lock bar 1000b the first and second friction lock members 1000c, 1000d may be continuously repositioned with respect to the friction lock bar 1000b. In this way, the first and second friction lock members 1000c, 1000d may be configured to embody a free flowing movement as they are slid back and forth on the friction lock bar 1000a.

Referring now to FIG. 11A, a device 1100 is illustrative of another embodiment of the invention. A friction lock 1110 is operatively coupled to the upper hinge assembly 113. In one embodiment, the friction lock 1110 has a pivoting connection with the upper hinge assembly 113 such that the friction lock 1110 may swivel, or rotate, around its connection point. A sliding bar 1120 having a proximal end 1120a and a distal end 1120b, is operatively coupled to both the friction lock 1110 and the lower hinge assembly 114. In one embodiment, the distal end 1120b of the sliding bar 1120 is pivotally connected to the lower hinge assembly 114 such that the sliding bar 1120 may rotate, or pivot, about its distal end 1120b. In one embodiment, the proximal end 1120a is positioned such that the sliding bar 1120 passes through the friction lock 1110, and the proximal end 1120a extends beyond the friction lock 1110.

In one embodiment, the friction lock 1110 may allow the sliding bar 1120 to slide in one direction, but resist or restrict movement of the sliding bar in the opposite direction. For example, the friction lock 1110 may be configured to allow the sliding bar 1120 to slide along the friction lock 1110, in the direction of the proximal end of the sliding bar 1120a, but the friction lock may prevent the sliding bar 1120 from reversing direction and moving toward the distal end 1120b. Applying this orientation of the friction lock 1110 to FIG. 11A, as the arm of the user 314 rotates about the pivot axis from a fully extended position (as shown) to a flexed position (not shown), the sliding bar 1120 will move further through the friction lock 1110, such that the distal end of the sliding bar 1120b is closer in distance to the friction lock 1110 than when the arm of the user 314 was fully extended. FIG. 11B is illustrative of this second position of the device 1100, whereby the arm of the user 314 is substantially flexed, the distal end of the sliding bar 1120b is closer in distance to the friction lock 1110, and the proximal end of the sliding bar 1120a is farther away in distance to the friction lock 1110. Continuing the example illustrated by FIGS. 11A and 11B, if the user's arm 314 attempts to reverse direction, and exerts a force that would normally cause extension of the elbow, the friction lock 1110 will prevent the sliding bar 1120 from travelling back through the friction lock 1110, and will keep the arm in the flexed position. As this device may be used by users 314 with trouble flexing their elbows, such a feature will help a user 314 maintain or improve the amount of flexion in an arm without moving back to an extended position.

Alternatively, the device 1100 may be configured such that the friction lock 1110 is oriented in the opposite direction. In such an embodiment, the sliding bar 1120 may only slide in the direction toward the distal end 1120b of the sliding bar, and away from the proximal end 1120a. Such an embodiment allows an arm of a user 314 in some degree flexion to either maintain its current position or move to a second position that is closer to full extension than the first position. If the arm of the user 314 attempts to move back into a more flexed position, the friction lock 1110 may prevent the sliding bar 1120 from travelling back through the friction lock 1110. As this device may be used by users 314 with trouble extending their elbows, such a feature will help a user maintain or improve the amount of extension in an arm without moving back to a flexed position.

In any of the friction lock 1110 embodiments, the friction lock 1110 may have two or more configurations. One possible configuration restricts travel of a sliding bar 1120 in a first direction. A second possible configuration restricts travel of a sliding bar 1120 in a second direction, where the second direction is the opposite direction of the first direction. A third possible configuration restricts travel of a sliding bar 1120 in both the first and second directions, such that the sliding bar, and therefore the arm of the user 314, is locked into one position. In a fourth configuration, a release is activated in the friction lock 1110 and the sliding bar 1120 is free to slide in both the first and second direction.

In one embodiment of the device 1100 illustrated in FIGS. 11A and 11B the only force that moves the sliding bar 1120 through the friction lock 1110 is the arm of the user, whether through the user flexing or extending its own arm 314, the user applying pressure to the sliding bar 1120 with a second arm, or a third person applying pressure to the sliding bar 1120. In another embodiment, a force application mechanism is operatively coupled to the sliding bar 1120 and the hinge support of the friction lock 1110, such that the force application mechanism may push or pull the sliding bar through the friction lock 1110. In one embodiment, the force application mechanism is a cam device. In another embodiment, the force mechanism is a roller that applies friction in one direction on the sliding member 1120 to push the sliding member into a second position from a first position. Such a roller may be activated electronically or through manual force. The benefit of adding a force application mechanism to the device 1100 in FIGS. 11A and 11B is to allow a user 314 to force the joint of the user's elbow 314 into either flexion or extension when the user is incapable of doing so without aid.

In addition to, or in lieu of, the above-mentioned embodiments, one or more inflatable members (e.g. an inflatable bladder) may be used to manipulate the arm of a user 314 into extension or flexion. In some embodiments, the inflatable member is used in conjunction with the arm engagement system 100 illustrated in FIG. 1 and FIG. 2.

FIG. 12 illustrates one embodiment of the arm engagement device 1300 comprising an inflatable member 1310.

The device 1300 is generally the same as the device 100 in FIG. 1, but an inflatable member 1310 is positioned between forearm support 111 and the forearm of a user 314. In some embodiments, a second inflatable member 1310 may be positioned between the upper arm support 110 and the upper arm of the user 314. In one embodiment, the inflatable member 1310 is a bladder inflatable by air or fluid. In some embodiments, an inflator 1320 is used to inflate the inflatable member 1310. In some embodiments, the inflator is a pump. In some embodiments, the inflatable member 1310 may be deflated by a release 1330 that lets air or fluid out of the inflatable member 1310. As the inflatable member 1310 is inflated, the inflatable member 1310 may expand away from the forearm support 111. When a forearm of the user is engaged with the device 1300, inflating the inflatable member 1310 will provide a force 1350 on the forearm, expanding the distance between the forearm support 111 and the part of the hand of the user 314 that engages the inflatable member 1310. As such, an inflatable member 1310 positioned proximally to the pivot axis 116, and therefore proximal to the elbow of the user 314, will cause the arm of the user 314 to extend as the inflatable member 1310 is inflated. This extension because the elbow of the user 314 is being pushed away from the forearm support while the rest of the forearm and the upper arm are held in place by the straps 315a and 315c. Alternatively, an inflatable member 1310 positioned distally from the pivot axis 116, as well as from the elbow of the user, may promote flexion of the elbow of the user 314. This flexion occurs because the distal part of the forearm of the user 314, near the wrist, is extending away from the support while the rest of the forearm and the upper arm are held in place by the straps 315a and 315b.

Referring to FIG. 13, an inflatable member 1310 may be positioned between a forearm support 111 and a forearm cuff 1410. In such an embodiment, the forearm cuff 1410 may provide improved structural support and comfort to a forearm of a wearer 314 during inflation of the inflatable member 1310. The same configuration may also be applied to the upper arm area, or both the upper arm area and the forearm area. An inflatable member 1310 located proximal to the elbow joint may provide a force 1350 on the cuff 1410 that aids in extending the elbow joint of a wearer. An inflatable member 1310 located distally from the elbow joint may provide a force 1350 on the cuff 1410 that aids in flexing the elbow joint of a wearer. Again, the use of a cuff provides an additional advantage to older methods of applying a force imparting member directly to the arm as the device 1400 is likely used by wearers 314 that recently underwent surgery on their arms and need the support and comfort of the arm provided by a substantially rigid arm cuff 1410.

In one embodiment, the inflatable member 1310 may apply a force 1350 by expanding and increasing the distance between the forearm strapping system 315 and the arm of the wearer 314, although other configurations of the inflatable member 1310 may be used. In one embodiment, the inflatable member 1310 may be positioned between the forearm of the wearer 314 and at least one strap 315b, 315c, at a significant distance from the elbow joint, such that the force 1350 applied by the inflatable member 1310 pushes the distal section of the forearm further downward into the forearm support member 111 and increases the distance between the at least one strap 315b, 315c and the arm of the wearer 314, promoting extension. In another embodiment, the inflatable member 1310 may be positioned between the upper arm of the wearer 314 and the strap 315a, at a significant distance from the elbow joint, such that the force 1350 applied by the inflatable member pushes the upper arm further downward into the upper arm support member 110 and increases the distance between the strap 315b and the arm of the wearer 314, promoting extension. In yet another embodiment, the inflatable member may be positioned with respect to both the forearm and the upper arm of the wearer 314. In such an embodiment, a single inflatable member may extend alongside the arm of the wearer 314 from the wrist to the upper arm. Alternatively, two inflatable members may be utilized such that a first bladder that is positioned with respect to the forearm of the wearer 314, as previously discussed herein, and a second inflatable member is positioned with respect to the upper arm of the wearer 314, as previously discussed herein.

FIG. 14 illustrates one embodiment of the device 1500 that utilizes an inflatable member 1310 to apply a force 1350 on an arm of a wearer 314, causing the arm of the wearer 314 to rotate about the pivot axis 116. In this embodiment, a strap 315 wraps entirely around the forearm assembly of the forearm support 111, the forearm of a wearer 314 (not shown), and the inflatable member 1310. The inflatable member 1310 is located beneath the forearm support 111, and above part of the strap 315. As the inflatable member 1310 is inflated, it expands and provides a force 1350 on the strap 315, pushing the strap 315 downward, away from the forearm support 111. A resulting force 1350 is therefore also applied by the top of the strap 1350 which may engage the forearm of the wearer 314 and push the forearm of the wearer 314 downward, into the forearm support 111. As configured in FIG. 14, with the strap 315 and inflatable member 1310 positioned distally from the elbow, the resulting movement of the forearm 314 causes the arm of the wearer 314 to extend. Such a configuration, with the inflatable member 1310 located below the forearm support 315 may be advantageous to the earlier described embodiment where the inflatable member 1310 is pressing up against the arm of the user 314 because the strap 315 may provide more support and comfort to a wearer 314 than the inflatable member 1310 could provide.

As with all disclosed embodiments, these embodiments comprising inflatable members may be used in conjunction with any other extension or flexion embodiment described herein. This allows a wearer to utilize a general extension or flexion technique to position the elbow in a strategic orientation, and then use one or more inflatable members to apply a finer force 1350 to the joint of the wearer, thereby stretching damaged tissue at a more precise level and aiding in rehabilitation of the joint. Additionally, the inflatable member 1310 may comprise a release that deflates the inflatable member 1310 and therefore lessens or removes the force 1350 applied by the inflatable member 1310.

While the above embodiments were illustrated as applying to extension and flexion of an arm of a wearer about an elbow, one skilled in the art would understand that each of the previously discussed embodiments may also be utilized to promote extension and flexion of other body parts, where there is a first and second body part connected by a joint. As such, these embodiments could be used in elbow, wrist, finger, shoulder, neck, hip, knee, ankle, and/or toe embodiments.

Apparatus for Providing Flexion of the Wrist

The following embodiments and additional components may be discussed in conjunction with the embodiments of FIGS. 1 and 2 for the purpose of providing flexion and extension of a wrist joint. As such FIGS. 15A-F illustrates the device 100 in more detail than previously depicted in FIG. 1 and FIG. 2.

Figure 15A:
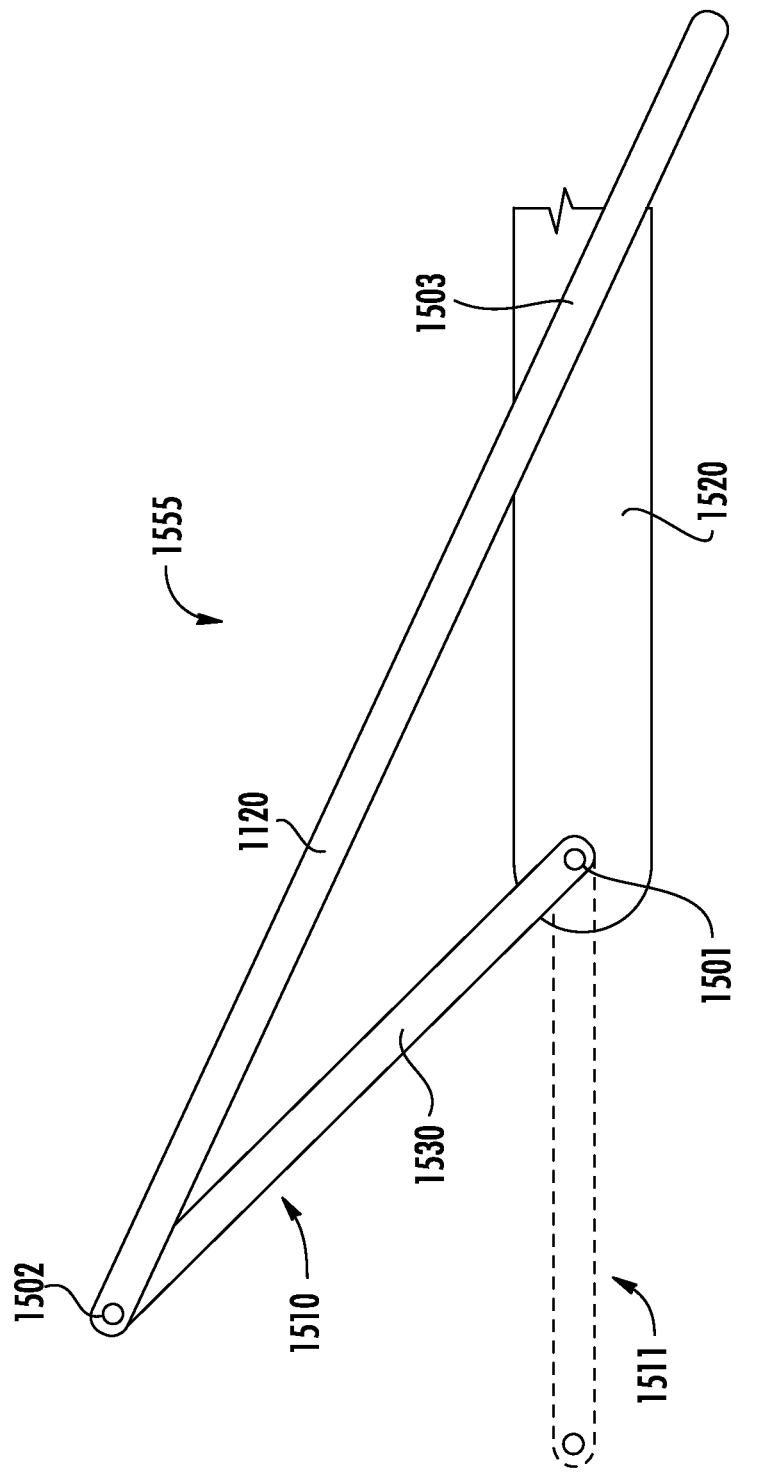

FIG. 15A illustrates the general concept of a device 1555 configured to manipulate a first body member 1530 relative to a second body member 1520 where the first and second body members 1520, 1530 are connected at a first pivot 1501, and a sliding bar 1120 is connected to the first body member at a second pivot 1502 and the second body member at a third pivot 1503. The first and second body members 1520, 1530 may rotate relative to each other about pivot 1501. Pivot 1501 may be a pivot, a living hinge, multiple pivots, or a sliding juncture. The first body member 1530 and the sliding bar 1120 may rotate relative to each other about pivot 1502. Pivot 1502 may be a pivot, a living hinge, multiple pivots, or a sliding juncture. The sliding bar 1120 and the first body member 1530 may rotate relative to each other at pivot 1503. Pivot 1503 may be a pivot, a living hinge, multiple pivots, or a sliding juncture. In one embodiment, pivot 1503 is a friction lock 1110 pivotally attached to the first body member 1520 such that the friction lock 1110 rotates substantially about the pivot axis caused by pivot 1503. Such a friction lock may allow the sliding bar to slide through the friction lock. In some embodiments, a force application mechanism applies a force to the sliding bar 1120 such that the sliding bar 1120 causes the second member 1530 to rotate[[s]] about the first member 1520. For example, in the embodied configuration of the device 1555, retracting the friction bar 1120 toward a friction lock 1110 located at pivot 1503 may cause the second body member 1530 in a first position 1511, to flex, relative to the first body member 1520, about pivot 1501 and end up at a second position 1510. The friction lock may be a friction clutch.

Figure 15B:
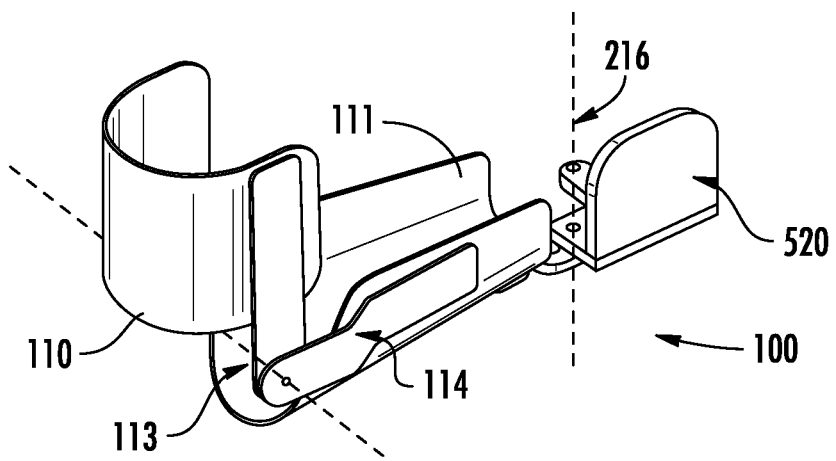
Figure 15C:
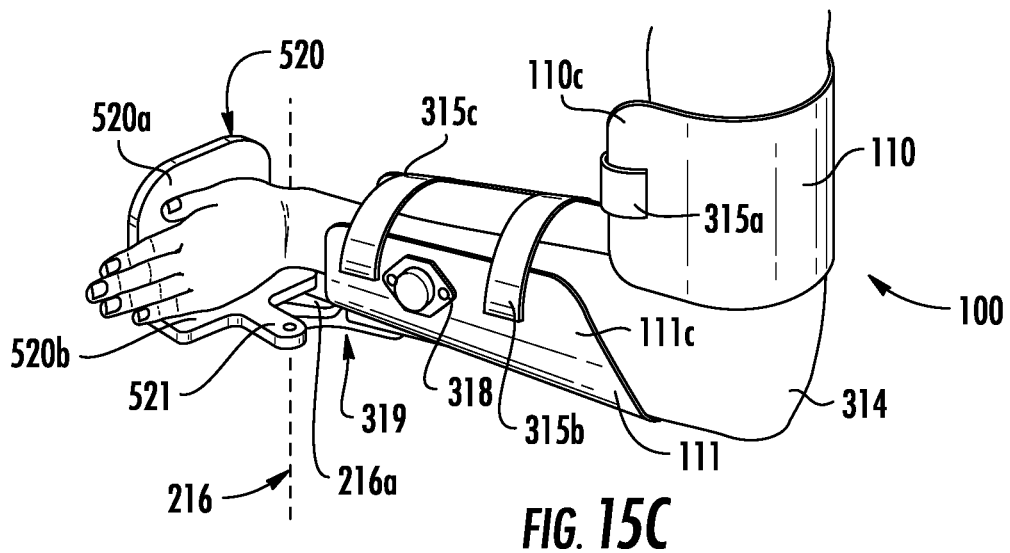
Figure 15D:
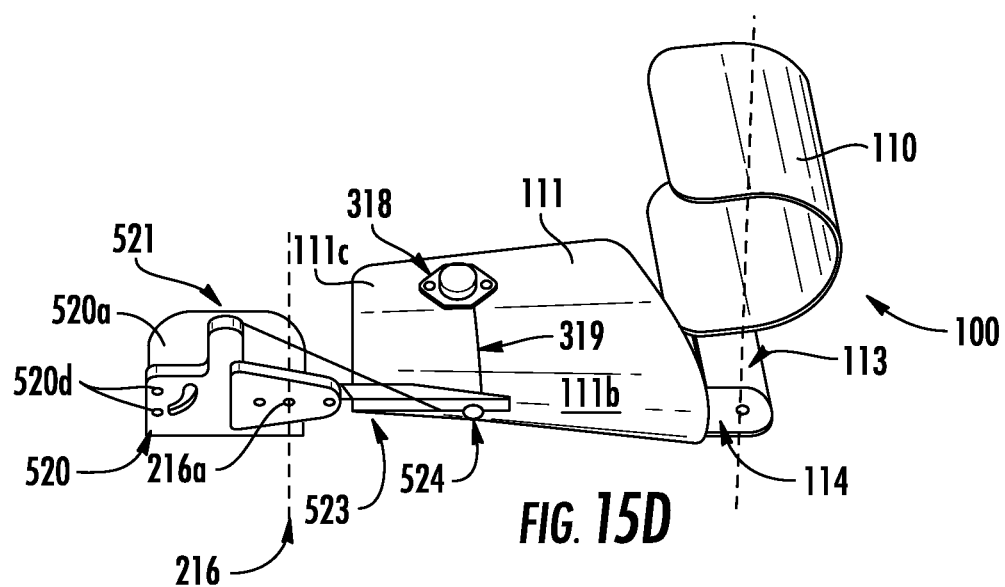

FIGS. 15B-D illustrate one possible variation of the apparatus 900 aimed at further promoting dorsiflexion and palmar flexion of the wrist by usage of a hand interface 520. As shown in FIG. 15D, the force application mechanism 318 is operatively coupled to the forearm support 511. A force applicator 319 extends outward from the force application mechanism 318, engages a force amplifier 524, and attaches to a hand interface 520 attachment point 521. The force amplifier 524 may be a guide or other device that may control the orientation and positioning of the force applicator 319 such that the force amplifier 524 may redirect an original force originating from the force application mechanism 318 and apply the force to the hand interface 520. In some embodiments, the force amplifier 524 is a hook, loop, peg, or other device configured to redirect a cable, line or other force applicator 319. A rigid extension member 523 may extend from the forearm support member 111 and operatively connect with the hand interface 520. The operative connection between the rigid extension member 523 and the hand interface 520 may be a pivoting connection such that the hand interface 520 may rotate relative around the pivot axis 216. In one embodiment, the pivot axis 216 is substantially a dorsiflexion and palmar flexion axis of a user's wrist, when engaged with the device 900. In such an embodiment, when a force is applied via the force application mechanism 318, the force applicator 319 is shortened, applying a force 950 to attachment point 521 of the hand interface 520. This force creates a torque, or moment, rotating the hand interface 520 about the pivot axis 910.

As illustrated in FIG. 15C, one embodiment of the invention comprises the palm of the user 314 being positioned adjacent to the inner side of the upright surface 520a of the hand interface 520. In this configuration, when the force application mechanism 318 is activated, the hand interface 520 pivots around the pivot axis 116, causing the wrist joint of the user 314 to flex in dorsiflexion. In another embodiment of the invention (not shown), the dorsal (back) side of the wearer's hand 314 is positioned adjacent to the inner side of the upright surface 520a of the hand interface 520 such that when a force is applied via the force application mechanism 318 the flexion conductor mechanism 522 acts as a pivot which allows the wrist joint of the user to flex into palmar flexion. In some embodiments, the hand interface 520 is configured to easily switch orientations relative to the rigid attachment member 523 and the axis 116 such that a singular device 900 may provide for both dorsiflexion and palmar flexion based on the configuration of the hand interface 520.

Referring again to FIG. 15D, the force application mechanism 318 may be positioned on the forearm support member 111. The force applicator 319 may extend outward from the force application mechanism 318 such that it partially winds around an exterior groove of the force amplifier 524 toward the attachment point 521 using one or more coupling mechanisms including, but not limited to, nuts, bolts, screws, adhesive, other rivets, or the like to attach the force applicator 319 to the hand interface 520. The attachment member 523 may be centrally positioned on the bottom of the medial portion 111b of the forearm support member 111 such that the attachment member 523 extends outward from the forearm support member 111 towards the hand interface 520. The attachment member 523 may be further operatively coupled to the hand interface 520 at a joint location 216c such that the hand interface 520 is positioned beneath at least a portion of the attachment member 523 that extends beyond the edge front edge of the forearm support member 111.

In one embodiment, the rigid attachment member 523 may be attached to the forearm support member 111, and extend outwards to the middle of the wearers 314 hand. In one embodiment, the rigid attachment member 523 may be positioned in a fixed or static orientation. In another embodiment, the rigid attachment member 523 may be positioned in a non-fixed or dynamic orientation such that it is configured to slide/extend radially outward and/or inward from the front end of the forearm support member 111 located proximate to the hand interface 520. In such an embodiment, the rigid attachment member 523 may be configured to be adjustable to accommodate different arm lengths of perspective wearers 314. The rigid attachment member 523 may be adjusted to extend outward allowing the device 900 to accommodate longer arm lengths, and rigid attachment member 523 may be adjusted to extend inward allowing the device 100 to accommodate shorter arm lengths. In such an embodiment, the distance between the hand interface 520 and the forearm support member 111 may widen or become narrower based on the adjustment of the rigid attachment member 523. For example, the distance between the hand interface 520 and the forearm support member 111 may increase when the rigid attachment member 523 is adjusted to extend further outward, and the distance between the hand interface 520 and the forearm support member 111 may decrease when the rigid attachment member 523 is adjusted to extend further inward. In such an embodiment, the rigid attachment member 523 may be operatively coupled to the forearm support member 111 by means of a dynamic adjustment mechanism such as a friction lock, to allow for adjustment of the rigid attachment member 523 relative to the forearm support member 111.

In some embodiments, the hand interface 520 may comprise a single upright surface 520a, such that the upright surface 520a may engage either the palmar side of a hand of a user 314 or a dorsal side of a hand of the user 314. In other embodiments, and in addition to the upright surface 520a, the hand interface 520 may comprise a horizontal support surface 520b such that the horizontal support surface 520b may engage the ulnar edge of the hand of a user 314. In some embodiments, the hand interface 520 may be comprised of a metal, hard plastic, or other rigid material. In some embodiments, the hand interface 520 may be comprised of a mildly flexible, resilient material. In some embodiments, the upright surface 520a may be flat, while in other embodiments, the upright surface 520a may be configured to conform to the shape of a hand.

In one embodiment, the hand interface 520 may comprise a single upright surface 520a that connects to the rigid attachment member 523 at the pivot point 216a, and to the force applicator 319 at the attachment point 521. The hand interface 520 may be defined by an "L-shaped" platform comprising an upright surface 520a, and a bottom surface 520b. The upright surface 520a and the bottom surface 520b may be positioned in a substantially perpendicular orientation with respect to one another. In one embodiment, the palm of the wearer (palmar side of the hand) is positioned adjacent to the inner side of the upright surface 520a of the hand interface 520 such that the ulnar side of the wearers hand is positioned adjacent to the bottom surface 520b of the hand interface 520, and when a force is applied via the force application mechanism 318, the hand interface 520 rotates about the pivot axis 216, manipulating the wrist joint of the wearer 314 to flex into dorsiflexion. In another embodiment, the dorsal side of the wearer's hand 314 is positioned adjacent to the inner side of the upright surface 520a of the hand interface 520 such that the ulnar side of the wearers hand is positioned adjacent to the bottom surface 520b of the hand interface 520, and when a force is applied via the force application mechanism 318, the hand interface 520 rotates about the pivot axis 216, manipulating the wrist joint of the wearer 314 to flex into palmar flexion. The flexion interface attachment point 521 may be located at a distal point of the extension tab 520a. In some embodiments, the attachment point 521 may be located at a distal point 521 of the horizontal side of 520b of the hand interface 520. In another embodiment, the horizontal side 520b of the hand interface 520 may include an elongate member that extends outward from the hand interface 520, and the attachment member 521 may be located at a point along the elongate member. The hand interface 520 may further comprise one or more apertures 520d for the purpose of alternating the orientation of the hand interface 520 to allow the device to be worn on either the left or right arm of the wearer 314. In such an embodiment, the hand interface 520 may be removably coupled with the flexion conductor mechanism and/or the rigid attachment member 523 such that the hand interface 520 may be removed from a first orientation and reattached in a second orientation via the apertures 520d and one or more means of attachments (e.g. rivets).

In the embodiment of FIG. 15B through Figure D, the force application mechanism 318 may be utilized to shorten and/or lengthen the force application 319 with respect to the flexion interface attachment point 521 and the force amplifier 524, such that when the force applicator 319 is substantially shortened the hand interface 520 is positioned such that the wrist joint of the wearer 314 is in either a dorsiflexion or palmar flexion orientation. In one embodiment, an incremental force may be applied to the device by the force application mechanism 318 via the force applicator 319. In such an embodiment, the force applicator 319 may be shortened in increments such that the force resulting from each increased increment, incrementally pivots the hand interface 520 about the pivot axis 216, and subsequently cause flexion in the wrist of the wearer 314. In another embodiment, a continuous force may be applied to the device by the force application mechanism 318 via the force applicator 319. In such an embodiment, the force applicator 319 may be continuously shortened such that the resulting force continuously pivots the hand interface 520 about the axis 216, and subsequently cause flexion in the wrist of the wearer 314. In either embodiment, the force may be applied in one direction with respect to the force application mechanism 318, such that the force applicator may only shorten and may not extend. In some embodiments, the force application mechanism 318 may comprise a means for releasing the force in an opposite direction (e.g. a release button) and subsequently allowing the force applicator 319 to lengthen.

The embodiment illustrated in FIG. 15B through FIG. 15D, may also allow for radial and ulnar deviation of the wrist. This may be accomplished by rotating the hand interface 520 ninety degrees, relative to the hand of the user 314 such that the upright side 520*a* of the hand interface 520 may engage either the ulnar or radial side of the hand. It should be noted that while this embodiment may be accomplished by rotating the hand interface 520 at a ninety degree angle, the embodiment may also be accomplished by rotating the hand interface at other angles (e.g. 0° to 180°) not contemplated herein. In some embodiments, an additional hole or holes may be drilled into the hand interface 520 such that the attachment point 521 is relocated to an anatomically correct position. The hand interface 520 may be attached to the forearm support member 111 by a pivoting connection between rigid attachment member 523 and flexion conductor mechanism 522. In such an embodiment a force is applied by the force application mechanism 318, via the force applicator 319, pivoting the hand interface 520 about the pivot axis 216 such that the wrist may flex into either radial or ulnar deviation. In one embodiment, the radial side of the wearer hand is positioned adjacent to the inner side of the upright surface 520*a* of the hand interface 520 such that when a force is applied via the force application mechanism 318 the flexion conductor mechanism 522 acts as a pivot which allows the joint to flex into an ulnar deviation. In another embodiment, the ulnar side of the wearers 314 hand is positioned adjacent to the inner side of the upright surface 520*a* of the hand interface 520 such that when a force is applied via the force application mechanism 318 the flexion conductor mechanism 522 acts as a pivot which allows the joint to flex into a radial deviation. In some embodiments, the hand interface 520 is configured to easily switch orientations relative to the rigid attachment member 523 and the axis 216 such that a singular device 100 may provide for both radial ulnar deviation based on the configuration of the hand interface 520.

Friction Lock Embodiment

Figure 15E:
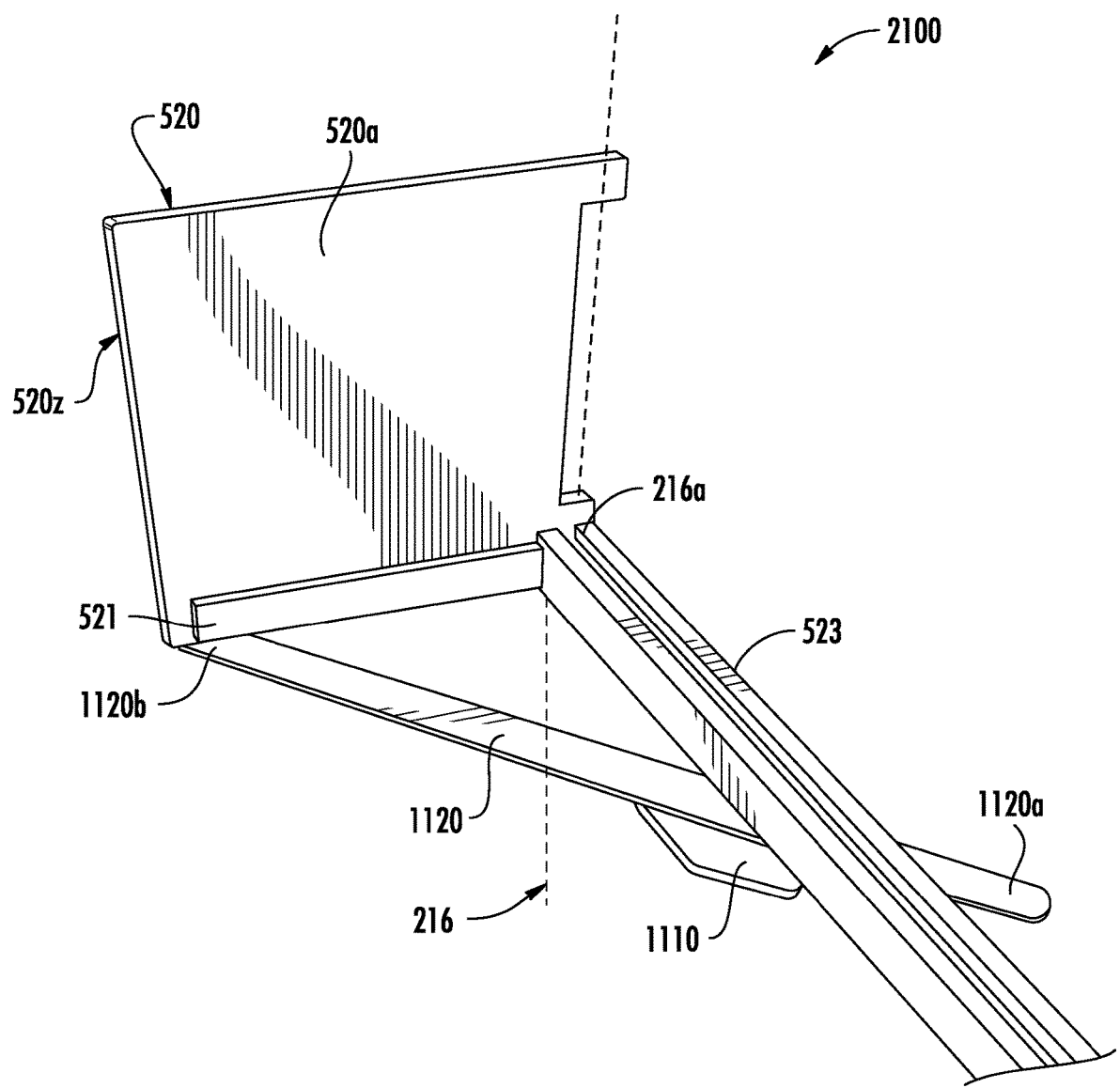

FIG. 15E illustrates the device 2100 in more detail than previously depicted in FIG. 1 and FIG. 2. FIG. 15E illustrates a wrist flexion assembly 2100 removed from the arm support assembly so that the embodiments may be fully viewed. The rigid extension member 523 would be secured to the arm support assembly as previously discussed. The rigid extension member 523 would also be operatively connected to the hand interface 520 at a pivot point 216*a*, such that the hand interface 520 may rotate about the pivot axis 216. Additionally, a sliding bar 1120 and friction lock 1110 assembly is provided. The sliding bar 1120 engages the friction lock 1110 such that the sliding bar 1120 may pass through the friction lock 1110. The sliding bar 1120 comprises a proximal end 1120*a* (proximal to the wearer 314) and a distal end 1120*b*. In one embodiment, the distal end 1120*b* of the sliding bar 1120 is operatively connected to an attachment point 521 such that the distal end 1120*b* of the sliding bar 1120 is connected to the hand interface 520 and such that the sliding bar 1120 and the hand interface 520 may rotate relative to each other about the attachment point 521.

In one embodiment, the sliding bar may pass through the friction lock 1110 such that the proximal end 1120*a* and the distal end 1120*b* may be on opposite sides of the friction lock 1110. The friction lock 1110, as previously described, may be pivotally connected to the rigid extension member 523 such that the friction lock 1110 may swivel, or pivot, in relation to the rigid extension member 523. By allowing the friction lock to pivot, the friction lock 1110 may always be oriented in the same direction as the sliding bar, as the sliding bar 1120 pivots relative to the hand interface 520, about the attachment point 521.

In one embodiment, the friction lock 1110 may allow the sliding bar 1120 to slide in one direction, but resist or restrict movement of the sliding bar in the opposite direction. For example, the friction lock 1110 may be configured to allow the sliding bar 1120 to slide along the friction lock 1110, in the direction of the proximal end of the sliding bar 1120*a*, but the friction lock may prevent the sliding bar 1120 from reversing direction and moving toward the distal end 1120*b*. Applying this orientation of the friction lock 1110 to FIG. 15E, as hand interface 520 pivots about the pivot axis 216 in a clockwise motion, the sliding bar 1120 will move further through the friction lock 1110, such that the distal end of the sliding bar 1120*b* is closer in distance to the friction lock 1110 than when the arm of the user 314 was fully extended. If the right forearm, wrist, and hand of a user 314 engaged the device 2100 in such a configuration, with the dorsal side of the user's hand engaging the upright surface 520*a*, then the wearer's wrist 314 would undergo palmar flexion as the sliding bar 1120 moves through the friction lock. Continuing the example, if the user's right arm 314 attempts to reverse direction, and exerts a force that would normally cause dorsiflexion of the wrist and hand, the friction lock 1110 will prevent the sliding bar 1120 from travelling back through the friction lock 1110, and will keep the wrist in the flexed position. Such an embodiment allows wrist of a user 314 to either maintain its current position (a first position) or move to a second position through palmar flexion. As this device may be used by users 314 with trouble achieving palmar flexion of the wrist, such a feature will help a user 314 maintain or improve the amount of palmar flexion in an arm without moving back to an extended position.

Alternatively, the device 1100 may be configured such that the friction lock 1110 is oriented in the opposite direction. In such an embodiment, the sliding bar 1120 may only slide in the direction toward the distal end 1120*b* of the sliding bar, and away from the proximal end 1120*a*. For such an embodiment, a user's right hand 314 may be positioned on the rear surface 520*z* of the upright surface 520*a*, so that the palmar side of the user's right hand 314 may engage the hand interface 520 along the rear surface 520*z*. Such an embodiment allows wrist of a user 314 to either maintain its current position (a first position) or move to a second position through dorsiflexion. If the right arm of the user 314 attempts to move back into palmar flexion, the friction lock 1110 may prevent the sliding bar 1120 from travelling back through the friction lock 1110. As this device may be used by users 314 with trouble extending their wrists from a substantially palmar flexion position to a substantially extended position, such a feature will help a user maintain or improve the amount of extension of the wrist without moving back to a more palmar flexed position. Note that the use of "extension" in these embodiments, relating to the wrist, may also be considered movement from a first position of dorsiflexion to a second position of lower dorsiflexion.

Figure 15F:
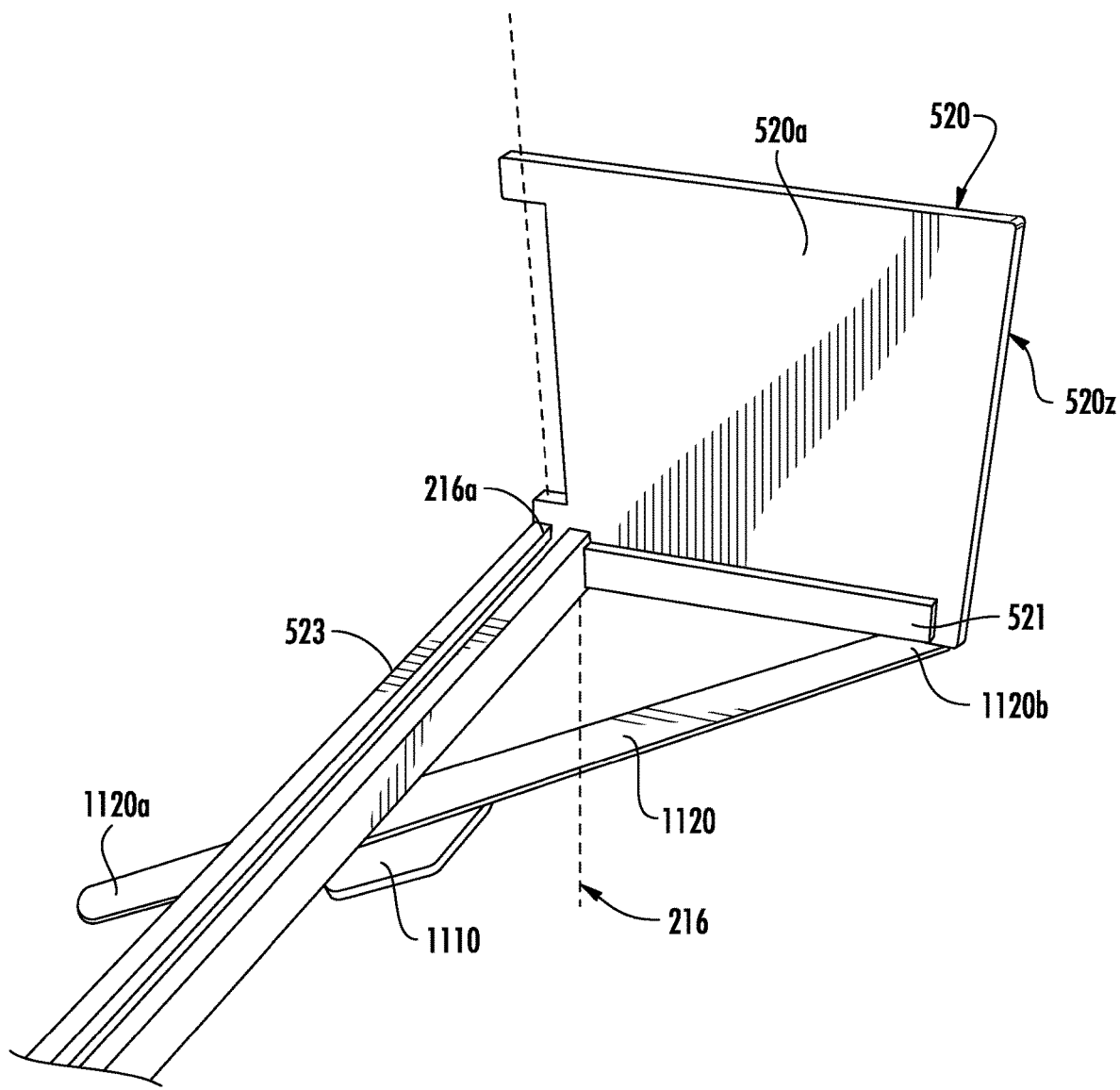

In another embodiment, as illustrated by FIG. 15F, the hand interface 520 may pivot around the pivot axis 216 and become oriented on the opposite side of the rigid extension member 523. As the friction lock 1110 may pivot in all directions, the entire assembly may easily change its orientation without removing or substantially altering its elements. In some embodiments, the friction lock 1110 may need to be released such that the sliding bar may freely slide in both directions, relative to the friction lock, so that the wrist flexion assembly 2100 may enter into this second orientation. This modular embodiment of the wrist flexion assembly 2100 allows a user 314 to promote both dorsiflexion and palmar flexion of a single arm of the user 314 with a single device 2100. For example, the user 314 may be able to promote palmar flexion by positioning engaging dorsal side of the right hand of the user 314 with the upright side of the hand interface 520a of the wrist flexion assembly 2100 configured in FIG. 15E. The user 314 may then switch the configuration of the wrist flexion assembly 2100 to the configuration shown in FIG. 15F, engage the palmar side of the user's hand 314 with the upright surface of the hand interface 520a, and the wrist flexion assembly 2100 may then assist the user's wrist 314 in dorsiflexion.

In any of the friction lock 1110 embodiments, the friction lock 1110 may have two or more configurations. One possible configuration restricts travel of a sliding bar 1120 in a first direction. A second possible configuration restricts travel of a sliding bar 1120 in a second direction, where the second direction is the opposite direction of the first direction. A third possible configuration restricts travel of a sliding bar 1120 in both the first and second directions, such that the sliding bar, and therefore the arm of the user 314, is locked into one position. In a fourth configuration, a release is activated in the friction lock 1110 and the sliding bar 1120 is free to slide in both the first and second direction.

In one embodiment of the wrist flexion assembly 2100 comprising a sliding bar 1120 and a friction lock 1110, a force application mechanism 318 may be applied to cause the sliding bar 1120 to slide in one direction. This embodiment may be similar to previously discussed embodiments, but the force applicator 319 in this example is the sliding bar 1120. By applying a force to the sliding bar 1120, the force application mechanism 318 will be assisting in the promotion of a flexion of the wrist (dorsiflexion or palmar flexion) depending on the orientation of the wrist flexion assembly 2100.

Inflatable Member

Referring to FIG. 16, in one embodiment, an inflatable member 1610 may be positioned between the left hand of a user 314 and the restrictive member 1660. The inflatable member 1610 may be expanded through inflation by an inflator 1620. In some embodiments, the inflator is a pump. The inflatable member 1610 may retract through deflation via a release 1630. The expansion of the inflatable member 1610 may allow for an increase in the distance between the restrictive member 1660 and the left hand of the user 314 thus providing a force 1650 that assists in dorsiflexion of the left wrist of the user 314. While FIG. 16 illustrates one embodiment that involves assisting a left wrist of a user 314 in dorsiflexion, other embodiments of the invention allow for a right hand to be placed in the current device 1600, with the dorsal side of the right hand of the user 314 engaging the inflatable member 1610 such that the device 1600 may assist the right hand of the user 314 in palmar flexion.

In one embodiment, the inflatable member 1610 may be operatively coupled to the restrictive member 1660 via an adhesive, a strap, a hook, or other connection that substantially keeps the inflatable member 1610 in place beside or against the restrictive member 1660. In some embodiments, a strap is used to hold the inflatable member 1610 in place against the restrictive member 1660. In one embodiment, a strap is circumscribes the restrictive member 1660, the inflatable member 1610, and the hand of the wearer 314 such that all three elements are substantially held in place.

As illustrated in previous embodiments, the restrictive member 1660 may pivot about the pivot axis 216 such that the current configuration is mirrored across the rigid extension member 523. In one embodiment mirroring the device 1600 across the rigid extension member 523 requires removing the inflatable member 1610 from a first side of the restrictive member 1660 and re-attaching the inflatable member 1610 to a second side of the restrictive member 1660. In one embodiment, the inflatable member is positioned on both sides of the restrictive member 1660 such that mirroring the device 1600 does not require moving the inflatable member 1610 from one side of the restrictive member 1660 to the other.

As picture din FIG. 16, the restrictive member 1660 may be attached to a sliding bar 1120 at an attachment point 521 some distance from the pivot axis 216. The sliding bar 1120 may engage a sliding lock, as described before, such that the sliding bar 1120 may only slide in one direction while the friction lock 1110 restricts the sliding bar 1120 from sliding in the opposite direction. As illustrated in FIG. 16, the friction lock 1110 may be configured to allow the sliding bar 1120 to slide in the direction of 1120a, away from position 1120b. Such a movement would cause the restrictive member 1660, the inflatable member 1610, and the left hand of the wearer 314 to rotate substantially about the pivot axis 216, thus assisting the wrist of the user 314 in dorsiflexion. The friction lock may also be configured to prevent the sliding bar from sliding back in the opposite direction (toward 1120b). This restrictive force prevents the restrictive member 1660 from giving way, or rotating, when the inflatable member 1610 expands, thereby making the restrictive member 1660 restrictive in one-way directional motion. This restricted orientation of the restrictive member 1660 causes the inflatable member 1610 to expand away from the restrictive member 1660 when inflated, so that it may engage the palmar side of the left hand of the wearer 314, and thereby causing the left hand of the user 314 to rotate substantially about the pivot axis 216 in dorsiflexion. Deflating the inflatable member 1610 would allow the left hand of the user 314 to rotate back, substantially about the pivot axis 216, in palmar flexion. Of course, this exact embodiment could be engaged by a right hand of a user 314, causing the right hand of the user 314 to enter palmar flexion when the inflatable member 1610 is expanded. And again, the entire embodiment may pivot about the pivot axis 216 such that the embodiment is mirrored on the other side of the rigid extension member 523.

FIG. 16 includes the sliding bar 1120 and friction lock 1110 previously discussed, but other embodiments are envisioned and, as all embodiments are interchangeable, the invention should not be limited to the embodiments pictured. For example, the inflatable member 1610 and its necessary elements may be used in conjunction with, and in addition to, the embodiments of the invention described and pictured in FIGS. 7-9.

In one embodiment, the inflatable member 1610 is positioned on the opposite side of the restrictive member 1660, such that the dorsal side of a hand of a user 314 may engage the inflatable member 1610. In such an embodiment, the friction lock 1110 may be reconfigured to only allow movement of the sliding bar 1120 in the direction of the distal end 1120b, and restricting movement toward the proximal end 1120a. In this embodiment, the restrictive member 1660 may only rotate counterclockwise relative to the pivot axis 216 and has a restricted orientation to not allow clockwise movement. This restricted orientation of the restrictive member 1660 causes the inflatable member 1610 to expand away from the restrictive member 1660 when inflated, such that it may engage the dorsal side of the left hand of the wearer 314, and thereby causing the left hand of the user 314 to rotate substantially about the pivot axis 216 in palmar flexion. Deflating the inflatable member 1610 would allow the left hand of the user 314 to rotate back, substantially about the pivot axis 216, in dorsiflexion. Of course, this exact embodiment could be engaged by a palmar side of a right hand of a user 314, causing the right hand of the user 314 to enter dorsiflexion when the inflatable member 1610 is expanded. And again, the entire embodiment may pivot about the pivot axis 216 such that the embodiment is mirrored on the other side of the rigid extension member 523.

In one embodiment, the friction lock 1110 or the force application mechanism 318 may be considered a restriction mechanism that restricts rotational movement in one direction for a restrictive member 1660. In one embodiment of the invention, the restrictive member 1660 is also a hand interface 520.

FIG. 17 illustrates a different embodiment of the device 1700. The device 1700 may be configured in substantially the same ways as device 1600, so the illustrated configuration is only for non-limiting example purposes. As illustrated, a hand interface 1710 may engage the palmar side of a left hand of a user. Generally, the hand interface 1710 may pivotally attach to the restrictive member 1660 and/or the rigid extension member 523 such that the hand interface 1710 may substantially rotate about the pivot axis 216. In some embodiments, the hand interface 1710 conforms to the hand of the user 314, or otherwise provides support to the hand.

Referring to the configuration of FIG. 17, as the inflatable member 1610 expands, it applies a force 1750 on the hand interface member 1710, causing the hand interface member 1710 to rotate counter clockwise about the pivot axis 216. Since the palmar side of the user's hand 314 is engaged with the hand interface, the force 1750 assists the wrist of the user 314 in dorsiflexion. The use of the hand interface 1710 allows the device 1700 to apply an evenly distributed force 1750 to the hand of a user 314. This evenly distributed force may be beneficial to a user 314 with an injured or sensitive hand as the entire hand 314 is supported throughout the engagement. Simply using the inflatable member, as described in FIG. 16, may cause an uneven force 1650 to be applied to the hand, which may be undesirable for some users 314 with injured or sensitive hands or wrists.

FIG. 18 illustrates another embodiment of the device 1800. The device 1800 may be substantially similar to the device 1600 of FIG. 16, with a few added and/or changed features. As illustrated, restriction member 1660 may engage a strap 1815. The strap 1815 may circumvent the restriction member 1660, an inflatable member 1610, and a hand of a user 314. In this embodiment, the palmar side of the hand is facing the restrictive member 1660, but the hand 314 is not engaging the restrictive member 1660 because the wrist of the user 314 is limited in palmar flexion motion and cannot flex enough to engage the hand of the user 314 with the restrictive member 1660. Therefore a gap exists between the palm of the user 314 and the surface of the restrictive member 1660. In this configuration, the restrictive member 1660 is restricted from moving clockwise about the pivot axis 216 such that the hand of the user 314 may only move in palmar flexion. This restrictive orientation of the restrictive member 1660 requires that the inflatable member 1610, when inflated, only expands toward the restrictive member 1660, away from the top of the strap 1815, and therefore applies a counterclockwise force 1850 on the hand of the user 314, assisting the wrist of the user 314 in palmar flexion.

FIG. 19 shows an alternate view of the device 1800. While FIG. 19 includes a friction lock 1110 as the restriction mechanism, any other restriction mechanism from prior art or herein described may be used. As with other embodiments discussed, this embodiment may be reconfigured such that the restrictive member 1660 is mirrored across the rigid extension member 523, such that a user 314 may engage the dorsal side of the hand 314 with the inflatable member 1610. In some embodiments, a hand interface 1710 may interpose the inflatable member 1610 and the hand of a user 314 such that an evenly distributed force may be applied across the hand of the user 314.

FIG. 20 illustrates another embodiment of the device 2000 similar to the device 1800 in FIGS. 18 and 19. As illustrated in FIG. 20, a strap 2015 may circumscribe an inflatable member 1610, a restrictive member 1660, and a hand of a user 314. In one embodiment, the inflatable member 1610 is on the opposite side of the restrictive member 1660. The dorsal side of the hand of the user 314 engages the strap 2015, but the palmar side of the hand 314 does not engage the restrictive member 1660. The hand of the user 314 may not engage the restrictive member 1660 because the wrist of the user 314 is limited in palmar flexion motion and cannot achieve enough palmar flexion to engage the restrictive member 1660 without assistance. In this configuration, the resistive member 1660 is resistant to clockwise motion because of its engagement with the sliding bar 1220 and the friction lock 1110 as previously described. Therefore, when the inflatable member 1610 expands, the inflatable member 1610 may only extend away from the restrictive member 1660, such that it applies a force 2050 on the bottom of the strap 2015. This force 2050 is therefore simultaneously applied at the top of the strap 2050 such that the strap 2015 may apply the force to the dorsal side of the hand of the user 314. This force 2050 may cause the hand of the user 314 to rotate substantially about the pivot axis 216 such that the wrist of the user 314 is assisted in palmar flexion and the hand of the user 314 may approach and/or engage the restrictive member.

As will several of the embodiments mentioned before, this device 2000 may be mirrored across the rigid extension member 523 such that the palmar side of the hand may engage the strap 2015 and the force 2050 caused by inflation of the inflatable member 1610 may assist in dorsiflexion of the wrist.

In one embodiment of the invention, the devices 1800, 2000, of FIGS. 18 and 20 may be combined into one device 2100, as generally illustrated in FIG. 21. Such a device may be configured in the same manner as the device 2000 in FIG.

20, except a second inflatable member 2110 is located between, and engages with, the dorsal side of the hand of the user 314 and the strap 2050, in the same manner as the inflatable member 1610 described in FIG. 18. The palmar side of the hand of the user 314 faces, but does not contact or engage the restrictive member 1660 such that a gap exists between the palmar side of the hand 314 and the surface of the restrictive member 1660. Continuing with the current example, the first inflatable member 1610 is located on, and engages with, the opposite side of the restrictive member 1660 from the hand of the user 314. Again, just as in FIG. 20, the strap 2015 engages the side of the inflatable member 1610 that faces away from the resistive member. Therefore the strap 2015 circumscribes a first inflatable member 1610, a restrictive member 1660, a gap between the restrictive member 1660 and the hand of the user 314, the hand of the user 314, and a second inflatable member.

As described in embodiment 2000, as the first inflatable member 1610 inflates, it expands downward from the restrictive member 1660, applying a "pulling" force 2150a to one or more straps 2120a, 2120b. This force 2150a, applied to the bottom of one or more straps 2120a, 2120b, creates a "pushing" force 2150b on the top of the same one or more straps 2120a, 2120b, such that the tops of the one or more straps 2120a, 2120b applies a force downward onto the second inflatable member 2110, which transfers the force 2150b to the dorsal side of the hand of the user 314. This pushing force 2150b causes the hand of the user 314 to move closer to the restrictive member 1660, assisting the wrist of the user 314 in palmar flexion. Either simultaneously or at a different point in time, the second inflatable member 2110 may be inflated. As described in embodiment 1800, as the second inflatable member 2110 inflates, it expands away from the one or more straps 2120a, 2120b, applying a "pushing" force 2150b on the dorsal side of the hand of the user 314. This force pushes the hand of the user 314 downward, into the gap between the palmar side of the hand 314 and the restrictive member 1660, generally assisting palmar flexion of the wrist of the user 314.

This combination of the "pushing" and "pulling" forces 2150a, 2150b on the hand of the user 314 allows the device 2100 to provide a stronger force 2150 to assist the wrist in flexion. The combination also allows for one inflatable member to exert a large force until the hand of the user 314 is in a desired orientation, before inflating a second inflatable member that is capable of applying a finer, or smaller, force to more precisely orient the wrist in a desired flexion. Of course, the same general embodiment may be mirrored such that the palmar side of the hand of the user 314 engages the second inflatable member and the device assists in dorsiflexion of the wrist of the user 314.

In some embodiments of the invention, two or more force application mechanisms may be provided. In some embodiments, two or more force applicators may be provided. In some embodiments, a first force application mechanism provides a first force, and a second force application mechanism provides a second, smaller force. In such an embodiment, the first force may be applied to a wrist or elbow of a user 314, causing the wrist or elbow to rotate about its joint until the joint is in a desired position. Then, the second force may be applied either incrementally or continuously to slowly and/or precisely assist the joint in further rotation. Such an embodiment may allow a user with limited range of motion in a joint to apply a first force to the joint and body members until the joint is at or near a limit of its range of motion, and then apply a second force to the joint and body members that further stretches the tissue around the joint at a more precise level so that the ideal amount of flexion or extension is achieved at the joint. In some embodiments, the two or more force application mechanisms may be two rotary dial mechanisms. In another embodiment, one force applicator may be a rotary dial and a second force application mechanism may be an inflatable member. These are merely examples and any force application mechanism known from prior art or disclosed herein may be used to satisfy these embodiments.

While some embodiments of the device disclosed herein comprise a first arm member, a second arm member, and a hinge or pivot, some embodiments do not comprise a pivoting connection between the first and second arm members. In one embodiment, no hinge is provided between the first and second arm members such that the elbow of the user 314 is the only hinged aspect of the device. In some embodiments, a living hinge may be provided, where the living hinge is a rubber or elastic connector between the two arm members that is very flexible in every direction, exerting very little force on the user such that the user's elbow comprises the main rotational element of the assembly. In one embodiment, the two arm members are connected by more than one pivoting hinge. In such an embodiment, the two or more hinges may pivot about the same axis, pivot along parallel axes to each other, or pivot along non-parallel axes. In one embodiment comprising multiple hinges, the multidirectional configuration of the hinges may allow for a full range of motion about the elbow, and not the unidirectional range of motion allowed by a single hinge.

According to various embodiments of the invention, one or more devices, systems, components, apparatuses may perform one or more process or method steps. As generally discussed in this description, for example, a device component may apply a force, direct a force, receive a force, engage a body part, manipulate a body part, engage and/or be operatively coupled to one or more other components, and/or function, perform, take action and/or any other method or process step described herein. Accordingly, embodiments of the invention include various methods for assisting with pronation and/or supination and/or extension and/or flexion of one or more body parts of a user as implemented in whole or in part by device components described herein, and in some cases, components not described herein and/or manual method or process steps.

According to various embodiments of the invention, assistance may be provided to (or about) any body part and/or joint of a user's body. While various embodiments described herein may specifically refer to a device that is used to provide assistance, for example, to an elbow joint of the user, to a wrist joint of the user, or to provide pronation and/or supination assistance, it should be understood that the devices, systems, components, apparatuses and the like discussed in this description may be used to assist other joints, including, but not limited to shoulders, hips, knees, ankles, knuckles, finger joints, toe joints and/or the like.

As used herein, the term "operatively coupled" is intended to refer to two or more devices, systems, components, apparatuses, body parts and/or the like being rigidly attached or connected, non-rigidly attached or connected, in mechanical communication with one another, directly attached or connected, indirectly attached or connected (for example, with one or more intermediate devices, systems, components, apparatuses, body parts and/or the like being interposed, disposed, attached, connected, coupled or the like in between). In various instances, operatively coupled refers to permanent, semi-permanent, detachable, removable, separable, inseparable, or other types of couplings.

As used herein, the term "proximate" is intended to refer to a relationship wherein two or more devices, systems, components, apparatuses, body parts and/or the like are disposed, interposed, placed, situated, connected, attached, coupled, operably coupled in a relatively close relationship. Proximate may refer to physical contact, substantially physical contact, or nearby. "Proximate an edge" is intended to refer to adjacent an edge, substantially adjacent an edge, near an edge, on an edge or the like. "Proximate a portion" is intended to refer to adjacent a portion, substantially adjacent a portion, near a portion, on a portion or the like.

In various embodiments described herein, a force applicator may be or include a cable, belt, line, elastic band, inelastic band, chain, wire, ribbon, some combination of the foregoing, and/or the like. In various embodiments, a force application mechanism may refer to any mechanism that applies a force, such as, but not limited to any of the force application mechanisms described herein, harmonic drive mechanisms, pneumatic drive mechanisms, planetary gear mechanisms, rotary mechanisms (e.g., continuous, non-incremental, incremental and/or the like), inflatable members, manual (e.g., user-generated) force application, winches, springs, and/or the like While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. A device for manipulating an arm of a user, thereby providing extension or flexion assistance to the arm about an elbow, the device comprising:
    an arm engagement system comprising:
        an upper arm member comprising an upper arm frame and an upper arm attachment member configured to engage an upper arm of the user;
        a forearm member comprising a forearm frame directly connected to the upper arm frame and a forearm attachment member configured to engage a forearm of the user; and
        a pivoting connection formed in the connection between the upper arm frame and the forearm frame, wherein the upper arm member and the forearm member are configured to pivot about the pivoting connection on an axis defined by the elbow as the arm of the user extends or flexes about the elbow; and
    a force application system comprising:
        a first elongate member connected at or near its proximal end (i) to the upper arm frame at a position between all of one or more upper arm attachment members and the pivoting connection or (ii) to the forearm frame at a position between all of one or more forearm attachment members and the pivoting connection, wherein a distal end of the first elongate member extends outward from the upper arm frame and the upper arm attachment member in a single direction substantially outward from a longitudinal axis of the upper arm when the device is worn on the arm of the user;
        a second elongate member connected at or near its proximal end (i) to the upper arm frame at a position between all of one or more upper arm attachment members and the pivoting connection or (ii) to the forearm frame at a position between all of one or more forearm attachment members and the pivoting connection, wherein a distal end of the second elongate member extends outward from the forearm frame and the forearm attachment member in a single direction substantially outward from a longitudinal axis of the forearm when the device is worn on the arm of the user;
        a force application mechanism comprising a rotary mechanism; and
        a force applicator comprising an elongated line extending a length from the force application mechanism and a distal end connected (i) at or near the distal end of the first elongate member or (ii) at or near the distal end of the second elongate member,
    wherein, when the first elongate member is connected at or near its proximate end to the forearm frame and the second elongate member is connected at or near its proximate end to the upper arm frame, the force application mechanism is connected at or near the distal end of the first elongate member, and the distal end of the force applicator is connected at or near the distal end of the second elongate member, and wherein the force application mechanism is configured to alter the length between the force applicator and the force application mechanism such that a force is applied to the force applicator, thereby providing extension assistance to the arm about the elbow;
    wherein, when the first elongate member is connected at or near its proximate end to the upper arm frame and the second elongate member is connected at or near its proximate end to the forearm frame, the force application mechanism is connected at or near the distal end of the second elongate member, and the distal end of the force applicator is connected at or near the distal end of the first elongate member, and wherein the force application mechanism is configured to alter the length between the force applicator and the force application mechanism such that a force is applied to the force applicator, thereby providing flexion assistance to the arm about the elbow.

2. The device of claim 1, wherein, when the first elongate member is connected at or near its proximate end to the forearm frame and the second elongate member is connected at or near its proximate end to the upper arm frame, as the force is applied by the force application mechanism, a distance between the distal portion of the first elongate member and the distal portion of the second elongate member decreases, thereby creating a first torque about the pivoting connection and about the joint the first torque urging the upper arm member and the forearm member away from one another to provide extension assistance to the arm about the elbow.

3. The device of claim 2,
    wherein, when providing extension assistance, the first elongate member forms a first acute angle with the upper arm frame, wherein the first acute angle is intermediate the first elongate member and the pivoting connection; and wherein the second elongate member forms a second acute angle with the forearm frame member, wherein the second acute angle is intermediate the second elongate member and the pivoting connection.

4. The device of claim 3, wherein the first and second elongate members cross at a position between their respective proximal and distal ends.

5. The device of claim 1, wherein, when the first elongate member is connected at or near its proximate end to the upper arm frame and the second elongate member is connected at or near its proximate end to the forearm frame, the force application mechanism, when the force is applied, urges the upper arm member and the forearm member from a first position relative to one another to a second position relative to one another, thereby providing extension or flexion assistance to the arm of the user.

6. The device of claim 1, wherein the rotary mechanism is configured to cause a non-incremental or continuous force to be applied to the force applicator when the rotary mechanism is activated by the user.

7. The device of claim 1,
wherein a first proximal distance between the proximal ends of the first and second elongate members is larger or the same as a first distal distance between the distal ends of the first and second elongate members when the device is providing extension assistance; and
wherein a second proximal distance between the proximal ends of the first and second elongate members is smaller than a second distal distance between the distal ends of the first and second elongate members when the device is providing flexion assistance.

8. The device of claim 1,
wherein, when providing flexion assistance, the first elongate member forms a first acute angle with the upper arm frame, wherein the first acute angle is intermediate the first elongate member and the upper arm attachment member; and
wherein the second elongate member forms a second acute angle with the forearm frame member, wherein the second acute angle is intermediate the second elongate member and the forearm attachment member.

9. The device of claim 1, wherein the first and second elongate members are substantially straight.

10. A device for manipulating an arm of a user, thereby providing extension or flexion assistance to the arm about an elbow, the device comprising:
an arm engagement system comprising:
an upper arm member configured to engage an upper arm of the user; and
a forearm member directly connected to the upper arm member and configured to engage a forearm of the user, the forearm member operatively coupled to the upper arm member at a pivoting connection, wherein the upper arm member and forearm member are configured to pivot about the pivoting connection formed in the connection between the upper arm member and the forearm member on an axis defined by a joint of the arm; and
a force application system comprising:
a first elongate member having a first end and a second end, wherein the first elongate member is selectively couplable between a first configuration and a second configuration;
a second elongate member having a first end and a second end, wherein the second elongate member is selectively couplable between the first configuration and the second configuration;
a force application mechanism comprising a rotary mechanism, the force application mechanism selectively couplable to either the first elongate member or the second elongate member; and
a force applicator comprising an elongated cable, the force applicator extending a length between a first end coupled to the force application mechanism and a second end coupled to either the first elongate member when the force application mechanism is coupled to the second elongate member or to the second elongate member when the force application mechanism is coupled to the first elongate member
wherein, when the first elongate member and the second elongate member are in the first configuration, the first elongate member and the second elongate member intersect and when the force application mechanism is activated, the rotary mechanism rotates in a non-incremental or continuous manner to shorten the length of the force applicator between the force application mechanism and the second end of the force applicator that is operatively coupled to at least one of the first elongate member and the second elongate member, thereby causing extension of the arm engagement system and the arm of the user, wherein the rotary mechanism is configured to secure the length of the force applicator between the force application mechanism and the second end of the force applicator in a non-incremental manner, and
wherein, when the first elongate member and the second elongate member are in the second configuration, the first elongate member and the second elongate member extend outwardly from the arm engagement system in a divergent manner and when the force application mechanism is activated, the rotary mechanism rotates in a non-incremental or continuous manner to shorten the length of the force applicator between the force application mechanism and the second end of the force applicator that is operatively coupled to at least one of the first elongate member and the second elongate member, thereby causing flexion of the arm engagement system and the arm of the user, wherein the rotary mechanism is configured to secure the length of the force applicator; and
wherein, when the force application mechanism is not activated, the rotary mechanism does not rotate and does not shorten or lengthen the length of the force applicator between the force application mechanism and the second end of the force applicator, thereby not causing extension or flexion of the arm engagement system and the arm of the user.

11. The device of claim 10, wherein when the force application mechanism is activated, the upper arm member and the forearm member form a first position relative to one another to a second position relative to one another, thereby providing extension or flexion assistance to the arm of the user.

12. A device for manipulating body parts of a user, thereby providing extension or flexion assistance to the body parts of the user about a joint of the user, the device comprising:
a body part engagement system comprising:

an upper body part member configured to engage an upper body part of the user; and a lower body part member directly connected to the upper body part member and configured to engage a lower body part of the user, the connection between the lower body part member and the upper body part member forming a pivoting connection, wherein the upper body part member and the lower body part member are configured to pivot about the pivoting connection on an axis defined by the joint of the user; and a force application system comprising:

a first elongate member connected at or near its first end to the upper body part member at a position between all of one or more upper arm attachment members and the pivoting connection;

a second elongate member connected at or near its first end to the lower body part member at a position between all of one or more forearm attachment members and the pivoting connection;

wherein a second end of the first elongate member extends outward from the upper body part member in at least one of a convergent direction and a divergent direction with respect to the second elongate member, and wherein a second end of the second elongate member extends outward from the lower body part member in at least one of a convergent direction and a divergent direction with respect to the first elongate member, wherein the first and second elongate members extend substantially outward from a longitudinal axis of the lower body part when the device is worn by the user;

a force application mechanism comprising a rotary mechanism; and a force applicator comprising an elongated belt having a first end extending a length from the force application mechanism to a second end connected (i) at or near the second end of the first elongate member or (ii) at or near the second end of the second elongate member, wherein the force application mechanism is operatively coupled at or near the second end of the first elongate member when the second end of the force applicator is connected at or near the second end of the second elongate member, or (ii) at or near the second end of the second elongate member when the second end of the force applicator is connected at or near the second end of the first elongate member, wherein, when the force application mechanism is activated, the rotary mechanism rotates in a non-incremental or continuous manner to shorten the length of the force applicator between the force application mechanism and the second end of the force applicator, thereby causing extension of the body engagement system and the body of the user when the first and second elongate members extend outwardly in a convergent manner or flexion of the body part engagement system and the body parts of the user when the first and second elongate members extend outwardly in a divergent manner, wherein the rotary mechanism is configured to secure the length of the force applicator between the force application mechanism and the second end of the force applicator in a non-incremental manner, and wherein, when the force application mechanism is not activated, the rotary mechanism does not rotate and does not shorten or lengthen the length of the force applicator between the force application mechanism and the second end of the force applicator, thereby not causing extension or flexion of the body part engagement system and the body parts of the user.

13. A method for manipulating body parts of a user, thereby providing extension or flexion assistance to the body parts of the user about a joint of the user, the method comprising:

engaging an upper body part of the user with an upper body part member of a body part engagement system;

engaging a lower body part of the user with a lower body part member of the body part engagement system, wherein the lower body part member is directly connected to the upper body part member forming a pivoting connection, and wherein the upper body part member and the lower body part member are configured to pivot about the pivoting connection on an axis defined by the joint of the user; and activating a force application mechanism comprising a rotary mechanism, the force application mechanism applying a continuous or non-incremental force to a first end of a force applicator comprising an elongated band, wherein a second end of the force applicator is operatively coupled either: (i) at or near a second end of a first elongate member, the first elongate member connected at or near its proximal end to the upper body part member between all of one or more upper body part attachments and the pivoting connection, the first elongate member extending in a first direction and a second direction outward from a longitudinal axis of the upper body part; or (ii) at or near a second end of a second elongate member connected at or near its proximal end to the lower body part member between all of one or more lower body part attachments and the pivoting connection, the second elongate member extending in a first direction and a second direction outward from a longitudinal axis of the lower body part, wherein when the second end of the force applicator is operatively coupled at or near the second end of the first elongate member, the first and second elongate members intersect each other and when the second end of the force applicator is operatively coupled at or near the second end of the second elongate member, the first and second elongate members diverge from each other, and wherein the applied continuous or non-incremental force causes a length between the first end of the force applicator and the distal end of the force applicator to shorten, thereby causing the body part engagement system and the body parts of the user to extend when the first and second elongate members intersect or flex when the first and second elongate members diverge, and deactivating the force application mechanism to cause the force application mechanism to secure the length of the force applicator between the force application mechanism and the second end of the force applicator in a non-incremental manner, thereby not shortening or lengthening the force applicator between the first end of the force applicator and the second end of the force applicator, and thereby not causing extension or flexion of the body part engagement system and the body parts of the user.

14. The method of claim 13, wherein prior to activating the force application mechanism to apply the continuous or non-incremental force, the upper body part member and the lower body part member are configured in a first position relative to one another, and wherein after the force application mechanism has been activated to apply the continuous or non-incremental force to the first end of the force applicator, the upper body part member and the lower body part member are in a second position relative to one another.

15. The method of claim 14, further comprising restricting movement of the upper body part member or the lower body part member from the second position toward the first position.

16. A device for manipulating an arm of a user, thereby providing extension assistance to the arm about an elbow, the device comprising:
   an arm engagement system comprising:
      an upper arm member comprising an upper arm frame and one or more upper arm attachment members configured to engage an upper arm of the user;
      a forearm member comprising a forearm frame directly connected to the upper arm frame and one or more forearm attachment members configured to engage a forearm of the user; and
      a pivoting connection formed in the connection between the upper arm frame and the forearm frame, wherein the upper arm member and the forearm member are configured to pivot about the pivoting connection on an axis defined by the elbow as the arm of the user extends about the elbow; and
   a force application system comprising:
      a first elongate member connected at or near its proximal end to the upper arm frame of the arm engagement system at a position intermediate the upper arm attachment members and the pivoting connection, wherein a distal end of the first elongate member extends in a first direction outward from the upper arm frame and the upper arm attachment member, the outward extension configured to be in a direction substantially outward from a longitudinal axis of the upper arm and at a substantially further distance from the upper arm than the proximal end of the first elongate member when the device is worn on the arm of the user;
      a second elongate member connected at or near its proximal end to the forearm frame at a position intermediate the forearm attachment members and the pivoting connection, wherein a distal end of the second elongate member extends in a second, intersecting direction with respect to the first elongate member and outward from a longitudinal axis of the forearm frame and the forearm attachment member, the outward extension configured to be in a direction substantially outward from the forearm;
      a force application mechanism; and
      a force applicator comprising an elongated belt extending a length from the force application mechanism and a distal end connected (i) at or near the distal end of the first elongate member or (ii) at or near the distal end of the second elongate member, wherein the force application mechanism is (i) connected at or near the distal end of the first elongate member when the distal end of the force applicator is connected at or near the distal end of the second elongate member, or (ii) connected at or near the distal end of the second elongate member when the distal end of the force applicator is connected at or near the distal end of the first elongate member, wherein the force application mechanism is configured to alter the length of the force applicator extending from the force application mechanism such that a force is applied to the force applicator, thereby providing extension assistance to the arm about the elbow.

17. A device for manipulating an arm of a user, thereby providing flexion assistance to the arm about an elbow, the device comprising:
   an arm engagement system comprising:
      an upper arm member comprising an upper arm frame and one or more upper arm attachment members configured to engage an upper arm of the user;
      a forearm member comprising a forearm frame directly connected to the upper arm frame and one or more forearm attachment members configured to engage a forearm of the user; and
      a pivoting connection formed in the connection between the upper arm frame and the forearm frame, wherein the upper arm member and the forearm member are configured to pivot about the pivoting connection on an axis defined by the elbow as the arm of the user flexes about the elbow; and
   a force application system comprising:
      a first elongate member connected at or near its proximal end to the upper arm frame of the arm engagement system at a position intermediate the upper arm attachment members and the pivoting connection, wherein a distal end of the first elongate member extends in a first direction outward from the upper arm frame and away from the forearm frame, the outward extension configured to be in a direction substantially outward from a longitudinal axis of the upper arm and at a substantially further distance from the upper arm than the proximal end of the first elongate member when the device is worn on the arm of the user;
      a second elongate member connected at or near its proximal end to the forearm frame at a position intermediate the forearm attachment members and the pivoting connection, wherein a distal end of the second elongate member extends in a second, divergent direction with respect to the first elongate member and outward from a longitudinal axis of the forearm frame and away from the upper arm frame, the outward extension configured to be in a direction substantially outward from the forearm;
      a force application mechanism; and
      a force applicator comprising an elongated line extending a length from the force application mechanism and a distal end connected (i) at or near the distal end of the first elongate member or (ii) at or near the distal end of the second elongate member, wherein the force application mechanism is (i) connected at or near the distal end of the first elongate member when the distal end of the force applicator is connected at or near the distal end of the second elongate member, or (ii) connected at or near the distal end of the second elongate member when the distal end of the force applicator is connected at or near the distal end of the first elongate member, wherein the force application mechanism is configured to alter the length of the force applicator extending from the force application mechanism such that a force is applied to the force applicator, thereby providing flexion assistance to the arm about the elbow.

* * * * *